(12) United States Patent
Pinto

(10) Patent No.: US 6,191,159 B1
(45) Date of Patent: Feb. 20, 2001

(54) DISUBSTITUTED PYRAZOLINES AND TRIAZOLINES AS FACTOR XA INHIBITORS

(75) Inventor: Donald J. P. Pinto, Newark, DE (US)

(73) Assignee: Dupont Pharmaceuticals Company, Wilmington, DE (US)

(*) Notice: Under 35 U.S.C. 154(b), the term of this patent shall be extended for 0 days.

(21) Appl. No.: 09/276,960

(22) Filed: Mar. 26, 1999

Related U.S. Application Data

(60) Provisional application No. 60/079,725, filed on Mar. 27, 1998.

(51) Int. Cl.[7] ............................ A61K 31/415; A61P 7/02; C07D 231/06; C07D 231/08
(52) U.S. Cl. ..................... 514/406; 514/407; 514/247; 514/252; 514/255; 514/256; 514/269; 514/315; 514/326; 514/336; 514/341; 514/360; 514/362; 514/363; 514/364; 514/365; 514/372; 514/374; 514/378; 514/383; 514/385; 514/396; 514/402; 514/406; 514/422; 514/427; 514/444; 514/461; 544/140; 544/238; 544/242; 544/333; 544/336; 544/371; 546/211
(58) Field of Search .................................. 514/406, 359, 514/383; 548/255, 262.2, 266.2, 268.2, 379.1

(56) References Cited

U.S. PATENT DOCUMENTS

| 5,424,334 | 6/1995 | Abood et al. | 514/562 |
|---|---|---|---|
| 5,463,071 | 10/1995 | Himmelsbach et al. | 548/251 |
| 5,550,147 | 8/1996 | Matsuo et al. | 514/406 |

FOREIGN PATENT DOCUMENTS

| 9514682 | 6/1995 | (WO) . |
|---|---|---|
| 9514683 | 6/1995 | (WO) . |
| 9518111 | 7/1995 | (WO) . |
| 9723212 | 7/1997 | (WO) . |
| 9730971 | 8/1997 | (WO) . |
| 9747299 | 12/1997 | (WO) . |
| 9828269 | 7/1998 | (WO) . |
| 9857934 | 12/1998 | (WO) . |
| 9857937 | 12/1998 | (WO) . |
| 9857951 | 12/1998 | (WO) . |

*Primary Examiner*—Cecilia Tsang
*Assistant Examiner*—Jane C. Osweeki
(74) *Attorney, Agent, or Firm*—David Vance

(57) ABSTRACT

The present application describes disubstituted pyrazolines and triazolines of formulae I and II:

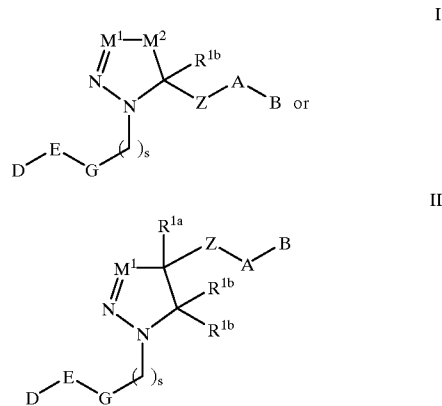

or pharmaceutically acceptable salt forms thereof, wherein one of $M^1$ and $M^2$ maybe N and D may be a variety of N-containing groups, which are useful as inhibitors of factor Xa.

45 Claims, No Drawings

DISUBSTITUTED PYRAZOLINES AND TRIAZOLINES AS FACTOR XA INHIBITORS

This application claims the benefit of U.S. Provisional Application No. 60/079,725, filed Mar. 27, 1998.

FIELD OF THE INVENTION

This invention relates generally to disubstituted pyrazolines and triazolines which are inhibitors of trypsin-like serine protease enzymes, especially factor Xa, pharmaceutical compositions containing the same, and methods of using the same as anticoagulant agents for treatment and prevention of thromboembolic disorders.

BACKGROUND OF THE INVENTION

WO 95/18111 addresses fibrinogen receptor antagonists, containing basic and acidic termini, of the formula:

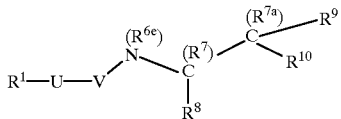

wherein $R^1$ represents the basic termini, U is an alkylene or heteroatom linker, V may be a heterocycle, and the right hand portion of the molecule represents the acidic termini. The presently claimed compounds do not contain the acidic termini of WO 95/18111.

In U.S. Pat. No. 5,463,071, Himmelsbach et al depict cell aggregation inhibitors which are 5-membered heterocycles of the formula:

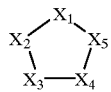

wherein the heterocycle may be aromatic and groups A—B—C— and F—E—D— are attached to the ring system. A—B—C— can be a wide variety of substituents including a basic group attached to an aromatic ring. The F—E—D— group, however, would appear to be an acidic functionality which differs from the present invention. Furthermore, use of these compounds as inhibitors of factor Xa is not discussed.

WO 97/47299 describes amidino and guanidino heterocyclic protease inhibitors of the formula:

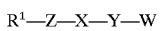

wherein W contains an amidino, guanidino, or imino group attached to a variety of moieties including phenyl and piperidinyl, Y is a O, N, S, or C linker or is absent, X is a heterocycle, Z is a two atom linker containing at least one heteroatom, and $R^1$ is a variety of groups including cycloalkyl, aryl, heteroaryl, and araalkyl all of which are optionally substituted. A variety of proteases are described as possible targets for these compounds including Factor Xa. The presently claimed compounds differ in that they do not contain the combination $R^1$—Z or Y—W.

WO 97/23212 describes isoxazolines, isothiazolines, and pyrazolines of the formula:

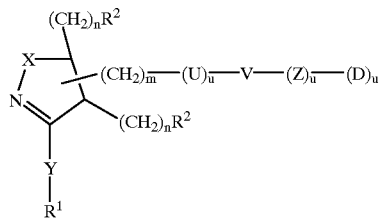

wherein X is O, S or $NR^{15}$. Though the pyrazolines of WO 97/23212 are indicated to be factor Xa inhibitors, they are not considered part of the present invention.

Activated factor Xa, whose major practical role is the generation of thrombin by the limited proteolysis of prothrombin, holds a central position that links the intrinsic and extrinsic activation mechanisms in the final common pathway of blood coagulation. The generation of thrombin, the final serine protease in the pathway to generate a fibrin clot, from its precursor is amplified by formation of prothrombinase complex (factor Xa, factor V, $Ca^{2+}$ and phospholipid). Since it is calculated that one molecule of factor Xa can generate 138 molecules of thrombin (Elodi, S., Varadi, K.: *Optimization of conditions for the catalytic effect of the factor IXa-factor VIII Complex: Probable role of the complex in the amplification of blood coagulation. Thromb. Res.* 1979, 15, 617–629), inhibition of factor Xa may be more efficient than inactivation of thrombin in interrupting the blood coagulation system.

Therefore, efficacious and specific inhibitors of factor Xa are needed as potentially valuable therapeutic agents for the treatment of thromboembolic disorders. It is thus desirable to discover new factor Xa inhibitors.

SUMMARY OF THE INVENTION

Accordingly, one object of the present invention is to provide novel disubstituted pyrazolines and triazolines which are useful as factor Xa inhibitors or pharmaceutically acceptable salts or prodrugs thereof.

It is another object of the present invention to provide pharmaceutical compositions comprising a pharmaceutically acceptable carrier and a therapeutically effective amount of at least one of the compounds of the present invention or a pharmaceutically acceptable salt or prodrug form thereof.

It is another object of the present invention to provide a method for treating thromboembolic disorders comprising administering to a host in need of such treatment a therapeutically effective amount of at least one of the compounds of the present invention or a pharmaceutically acceptable salt or prodrug form thereof.

These and other objects, which will become apparent during the following detailed description, have been achieved by the inventors' discovery that compounds of formulae I and II:

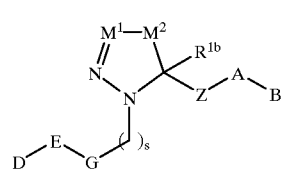

I

-continued

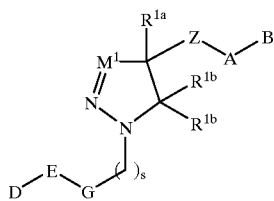

II or pharmaceutically acceptable salt or prodrug forms thereof, wherein A, B, D, E, G, M, Z, $R^{1a}$, $R^{1b}$, and s are defined below, are effective factor Xa inhibitors.

DETAILED DESCRIPTION OF PREFERRED EMBODIMENTS

[1] Thus, in a first embodiment, the present invention provides novel compounds of formulae I or II:

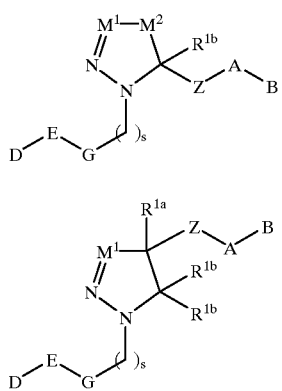

or a stereoisomer or pharmaceutically acceptable salt thereof, wherein;

$M^1$ is N or $CR^{1c}$;

$M^2$ is $NR^{1a}$ or $CR^{1a}R^{1a}$, provided that only one of $M^1$ and $M^2$ is a N atom;

D is selected from $C(=NR^8)NR^7R^9$, $NHC(=NR^8)NR^7R^9$, $NR^8CH(=NR^7)$, $C(O)NR^7R^8$, and $CR^8R^9NR^7R^8$;

E is selected from phenyl, pyridyl, pyrimidyl, pyrazinyl, pyridazinyl, and piperidinyl substituted with 1 R;

alternatively, D—E—G together represent pyridyl substituted with 1 R;

R is selected from H, Cl, F, Br, I, $(CH_2)_rOR^3$, $C_{1-4}$ alkyl, $OCF_3$, $CF_3$, $C(O)NR^7R^8$, and $(CR^8R^9)_rNR^7R^8$;

G is selected from $NHCH_2$, $OCH_2$, and $SCH_2$, provided that when s is 0, then G is absent;

Z is selected from a $C_{1-4}$ alkylene, $(CH_2)_rO(CH_2)_r$, $(CH_2)_r NR^3(CH_2)_r$, $(CH_2)_rC(O)(CH_2)_r$, $(CH_2)_rC(O)O(CH_2)_r$, $(CH_2)_rOC(O)(CH_2)_r$, $(CH_2)_rC(O)NR^3(CH_2)_r$, $(CH_2)_r NR^3C(O)(CH_2)_r$, $(CH_2)_rOC(O)O(CH_2)_r$, $(CH_2)_r OC(O)NR^3(CH_2)_r$, $(CH_2)_rNR^3C(O)O(CH_2)_r$, $(CH_2)_r NR^3C(O)NR^3(CH_2)_r$, $(CH_2)_rS(O)_p(CH_2)_r$, $(CH_2)_r SO_2NR^3(CH_2)_r$, $(CH_2)_rNR^3SO_2(CH_2)_r$, and $(CH_2)_r NR^3SO_2NR^3(CH_2)_r$, provided that Z does not form a N—N, N—O, N—S, $NCH_2N$, $NCH_2O$, or $NCH_2S$ bond with group A;

$R^{1a}$ and $R^{1b}$ are, at each occurrence, independently selected from H, $(CH_2)_r$—$R^{1'}$, $NCH_2R^{1''}$, $OCH_2R^{1''}$, $SCH_2R^{1''}$, $N(CH_2)_2(CH_2)_rR^{1'}$, $O(CH_2)_2(CH_2)_rR^{1'}$, and $S(CH_2)_2(CH_2)_rR^{1'}$;

$R^{1c}$ is selected from H, —$(CH_2)_q$—$R^{1'}$, $C_{1-3}$ alkyl, $C(O)R^{2c}$, $(CF_2)_rCO_2R^{2c}$, $C(O)NR^2R^{2a}$, $C_{3-6}$ carbocyclic residue substituted with 0–2 $R^4$, and 5–10 membered heterocyclic system containing from 1–4 heteroatoms selected from the group consisting of N, O, and S substituted with 0–2 $R^4$;

$R^{1'}$ is selected from H, $C_{1-3}$ alkyl, halo, $(CF_2)_rCF_3$, $OR^2$, $NR^2R^{2a}$, $C(O)R^{2c}$, $OC(O)R^2$, $(CF_2)_rCO_2R^{2c}$, $S(O)_p^{2b}$, $NR^2(CH_2)_rOR^2$, $NR^2C(O)R^{2b}$, $NR^2C(O)NHR^{2b}$, $NR^2C(O)_2R^{2a}$, $OC(O)NR^{2b}$, $C(O)NR^2R^{2a}$, $SO_2NR^2R^{2a}$, $NR^2SO_2R^{2b}$, $C_{3-6}$ carbocyclic residue substituted with 0–2 $R^4$, and 5–10 membered heterocyclic system containing from 1–4 heteroatoms selected from the group consisting of N, O, and S substituted with 0–2 $R^4$;

$R^{1''}$ is selected from H, $C(O)R^{2b}$, $C(O)NR^2R^{2a}$, $S(O)R^{2b}$, $S(O)_2R^{2b}$, and $SO_2NR^2R^{2a}$;

$R^2$, at each occurrence, is selected from H, $CF_3$, $C_{1-6}$ alkyl, benzyl, $C_{3-6}$ carbocyclic residue substituted with 0–2 $R^{4b}$, and 5–6 membered heterocyclic system containing from 1–4 heteroatoms selected from the group consisting of N, O, and S substituted with 0–2 $R^{4b}$;

$R^{2a}$, at each occurrence, is selected from H, $CF_3$, $C_{1-6}$ alkyl, benzyl, $C_{3-6}$ carbocyclic residue substituted with 0–2 $R^{4b}$, and 5–6 membered heterocyclic system containing from 1–4 heteroatoms selected from the group consisting of N, O, and S substituted with 0–2 $R^{4b}$;

$R^{2b}$, at each occurrence, is selected from $CF_3$, $C_{1-4}$ alkoxy, $C_{1-6}$ alkyl, benzyl, $C_{3-6}$ carbocyclic residue substituted with 0–2 $R^{4b}$, and 5–6 membered heterocyclic system containing from 1–4 heteroatoms selected from the group consisting of N, O, and S substituted with 0–2 $R^{4b}$;

$R^{2c}$, at each occurrence, is selected from $CF_3$, OH, $C_{1-4}$ alkoxy, $C_{1-6}$ alkyl, benzyl, $C_{3-6}$ carbocyclic residue substituted with 0–2 $R^{4b}$, and 5–6 membered heterocyclic system containing from 1–4 heteroatoms selected from the group consisting of N, O, and S substituted with 0–2 $R^{4b}$;

alternatively, $R^2$ and $R^{2a}$ combine to form a 5 or 6 membered saturated, partially saturated or unsaturated ring substituted with 0–2 $R^{4b}$ which contains from 0–1 additional heteroatoms selected from the group consisting of N, O, and S;

$R^3$, at each occurrence, is selected from H, $C_{1-4}$ alkyl, and phenyl;

$R^{3a}$, at each occurrence, is selected from H, $C_{1-4}$ alkyl, and phenyl;

A is selected from:
$C_{3-10}$ carbocyclic residue substituted with 0–2 $R^4$, and
5–10 membered heterocyclic system containing from 1–4 heteroatoms selected from the group consisting of N, O, and S substituted with 0–2 $R^4$;

B is selected from:
X—Y, $NR^2R^{2a}$, $C(=NR^2)NR^2R^{2a}$, $NR^2C(=NR^2)NR^2R^{2a}$,
$C_{3-10}$ carbocyclic residue substituted with 0–2 $R^{4a}$, and
5–10 membered heterocyclic system containing from 1–4 heteroatoms selected from the group consisting of N, O, and S substituted with 0–2 $R^{4a}$;

X is selected from $C_{1-4}$ alkylene, —$CR^2(CR^2R^{2b})(CH_2)_t$—, —$C(O)$—, —$C(=NR)$—, —$CR^2(NR^{1''}R^2)$—, —$CR^2(OR^2)$—, —$CR^2(SR^2)$—, —$C(O)CR^2R^{2a}$—, —$CR^2R^{2a}C(O)$, —$S(O)_p$—, —$S(O)_pCR^2R^{2a}$—, —$CR^2R^{2a}S(O)_p$—, —$S(O)_2NR^2$—, —$NR^2S(O)_2$—, —$NR^2S(O)_2CR^2R^{2a}$—, —$CR^2R^{2a}S(O)_2NR^2$—, —$NR^2S(O)_2NR^2$—, —$C(O)NR^2$—, —$NR^2C(O)$—, —$C(O)NR^2CR^2R^{2a}$—, —$NR^2C(O)CR^2R^{2a}$—, —$CR^2R^{2a}C(O)NR^2$—, —$CR^2R^{2a}NR^2C(O)$—, —$NR^2C(O)O$—, —$OC(O)NR^2$—, —$NR^2C(O)NR^2$—, —$NR^2$—, —$NR^2CR^2R^{2a}$—, —$CR^2R^{2a}NR^2$—, O, —$CR^2R^{2a}O$—, and —$OCR^2R^{2a}$—;

Y is selected from:
  $(CH_2)_rNR^2R^{2a}$, provided that X—Y do not form a N—N, O—N, or S—N bond,
  $C_{3-10}$ carbocyclic residue substituted with 0–2 $R^{4a}$, and 5–10 membered heterocyclic system containing from 1–4 heteroatoms selected from the group consisting of N, O, and S substituted with 0–2 $R^{4a}$;

$R^4$, at each occurrence, is selected from =O, $(CH_2)_rOR^2$, halo, $C_{1-4}$ alkyl, —CN, $NO_2$, $(CH_2)_rNR^2R^{2a}$, $(CH_2)_rC(O)R^{2b}$, $NR^2C(O)R^{2b}$, $C(O)NR^2R^{2a}$, $NR^2C(O)NR^2R^{2a}$, $CH(=NR^2)NR^2R^{2a}$, $NHC(=NR^2)NR^2R^{2a}$, $SO_2NR^2R^{2a}$, $NR^2SO_2NR^2R^{2a}$, $NR^2SO_2$—$C_{1-4}$ alkyl, $NR^2SO_2R^5$, $S(O)_pR^5$, $(CF_2)_rCF_3$, $NCH_2R^{1''}$, $OCH_2R^{1''}$, $SCH_2R^{1''}$, $N(CH_2)_2(CH_2)_rR^{1'}$, $O(CH_2)_2(CH_2)_rR^{1'}$, and $S(CH_2)_2(CH_2)_rR^{1'}$,
alternatively, one $R^4$ is a 5–6 membered aromatic heterocycle containing from 1–4 heteroatoms selected from the group consisting of N, O, and S;

$R^{4a}$, at each occurrence, is selected from =O, $(CH_2)_rOR^2$, halo, $C_{1-4}$ alkyl, —CN, $NO_2$, $(CH_2)_rNR^2R^{2a}$, $(CH_2)_rC(O)R^{2b}$, $NR^2C(O)R^{2b}$, $C(O)NR^2R^{2a}$, $NR^2C(O)NR^2R^{2a}$, $CH(=NR^2)NR^2R^{2a}$, $NHC(=NR^2)NR^2R^{2a}$, $SO_2NR^2R^{2a}$, $NR^2SO_2NR^2R^{2a}$, $NR^2SO_2$—$C_{1-4}$ alkyl, $NR^2SO_2R^5$, $S(O)_pR^5$, and $(CF_2)_rCF_3$;
alternatively, one $R^{4a}$ is a 5–6 membered aromatic heterocycle containing from 1–4 heteroatoms selected from the group consisting of N, O, and S substituted with 0–1 $R^5$;

$R^{4b}$, at each occurrence, is selected from =O, $(CH_2)_rOR^3$, halo, $C_{1-4}$ alkyl, —CN, $NO_2$, $(CH_2)_rNR^3R^{3a}$, $(CH_2)_rC(O)R^3$, $NR^3C(O)R^{3a}$, $C(O)NR^3R^{3a}$, $NR^3C(O)NR^3R^{3a}$, $CH(=NR^3)NR^3R^{3a}$, $NH^3C(=NR^3)NR^3R^{3a}$, $SO_2NR^3R^{3a}$, $NR^3SO_2NR^3R^{3a}$, $NR^3SO_2$—$C_{1-4}$ alkyl, $NR^3SO_2CF_3$, $NR^3SO_2$-phenyl, $S(O)_pCF_3$, $S(O)_p$—$C_{1-4}$ alkyl, $S(O)_p$-phenyl, and $(CF_2)_rCF_3$;

$R^5$, at each occurrence, is selected from $CF_3$, $C_{1-6}$ alkyl, phenyl substituted with 0–2 $R^6$, and benzyl substituted with 0–2 $R^6$;

$R^6$, at each occurrence, is selected from H, OH, $(CH_2)_rOR^2$, halo, $C_{1-4}$ alkyl, CN, $NO_2$, $(CH_2)_rNR^2R^{2a}$, $(CH_2)_rC(O)R^{2b}$, $NR^2C(O)R^{2b}$, $NR^2C(O)NR^2R^{2a}$, $CH(=NH)NH_2$, $NHC(=NH)NH_2$, $SO_2NR^2R^{2a}$, $NR^2SO_2NR^2R^{2a}$, and $NR^2SO_2C_{1-4}$ alkyl;

$R^7$, at each occurrence, is selected from H, OH, $C_{1-6}$ alkyl, $C_{1-6}$ alkylcarbonyl, $C_{1-6}$ alkoxy, $C_{1-4}$ alkoxycarbonyl, $(CH_2)_n$-phenyl, $C_{6-10}$ aryloxy, $C_{6-10}$ aryloxycarbonyl, $C_{6-10}$ arylmethylcarbonyl, $C_{1-4}$ alkylcarbonyloxy $C_{1-4}$ alkoxycarbonyl, $C_{6-10}$ arylcarbonyloxy $C_{1-4}$ alkoxycarbonyl, $C_{1-6}$ alkylaminocarbonyl, phenylaminocarbonyl, and phenyl $C_{1-4}$ alkoxycarbonyl;

$R^8$, at each occurrence, is selected from H, $C_{1-6}$ alkyl and $(CH_2)_n$-phenyl;

alternatively, $R^7$ and $R^8$ combine to form a 5 or 6 membered saturated, ring which contains from 0–1 additional heteroatoms selected from the group consisting of N, O, and S;

$R^9$, at each occurrence, is selected from H, $C_{1-6}$ alkyl and $(CH_2)_n$-phenyl;

n, at each occurrence, is selected from 0, 1, 2, and 3;
m, at each occurrence, is selected from 0, 1, and 2;
p, at each occurrence, is selected from 0, 1, and 2;
q, at each occurrence is selected from 1 and 2;
r, at each occurrence, is selected from 0, 1, 2, and 3;
s, at each occurrence, is selected from 0, 1, and 2; and,
t, at each occurrence, is selected from 0 and 1.

[2] In a preferred embodiment, the present invention provides novel compounds of formulae Ia–Ib:

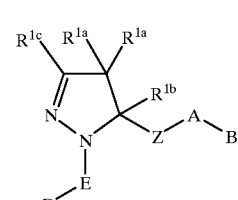

Ia

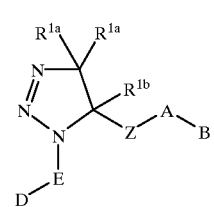

Ib wherein;
  Z is selected from a $CH_2O$, $OCH_2$, $CH_2NH$, $NHCH_2$, $C(O)$, $CH_2C(O)$, $C(O)CH_2$, $NHC(O)$, $C(O)NH$, $CH_2S(O)_2$, $S(O)_2(CH_2)$), $SO_2NH$, and $NHSO_2$, provided that Z does not form a N—N, N—O, $NCH_2N$, or $NCH_2O$ bond with group A;
  A is selected from one of the following carbocyclic and heterocyclic systems which are substituted with 0–2 $R^4$;
    phenyl, piperidinyl, piperazinyl, pyridyl, pyrimidyl, furanyl, morpholinyl, thiophenyl, pyrrolyl, pyrrolidinyl, oxazolyl, isoxazolyl, thiazolyl, isothiazolyl, pyrazolyl, imidazolyl, oxadiazolyl, thiadiazolyl, triazolyl, 1,2,3-oxadiazolyl, 1,2,4-oxadiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, 1,2,3-triazolyl, 1,2,4-triazolyl, 1,2,5-triazolyl, 1,3,4-triazolyl, benzofuranyl, benzothiofuranyl, indolyl, benzimidazolyl, benzoxazolyl, benzthiazolyl, indazolyl, benzisoxazolyl, benzisothiazolyl, and isoindazolyl;
  B is selected from: Y, X—Y, $NR^2R^{2a}$, $C(=NR^2)NR^2R^{2a}$, and $NR^2C(=NR^2)NR^2R^{2a}$;
  X is selected from $C_{1-4}$ alkylene, —$C(O)$—, —$C(=NR)$—, —$CR^2(NR^2R^{2a})$—, —$C(O)CR^2R^{2a}$—, —$CR^2R^{2a}C(O)$, —$C(O)NR^2$—, —$NR^2C(O)$—, —$C(O)NR^2CR^2R^{2a}$—, —$NR^2C(O)CR^2R^{2a}$—, —$CR^2R^{2a}C(O)NR^2$—, —$CR^2R^{2a}NR^2C(O)$—, —$NR^2C(O)NR^2$—, —$NR^2$—, —$NR^2CR^2R^{2a}$—, —$CR^2R^{2a}NR^2$—, O, —$CR^2R^{2a}O$—, and —$OCR^2R^{2a}$—;
  Y is $NR^2R^{2a}$, provided that X—Y do not form a N—N or O—N bond;
  alternatively, Y is selected from one of the following carbocyclic and heterocyclic systems which are substituted with 0–2 $R^{4a}$;

cylcopropyl, cyclopentyl, cyclohexyl, phenyl, piperidinyl, piperazinyl, pyridyl, pyrimidyl, furanyl, morpholinyl, thiophenyl, pyrrolyl, pyrrolidinyl, oxazolyl, isoxazolyl, isoxazolinyl, thiazolyl, isothiazolyl, pyrazolyl, imidazolyl, oxadiazolyl, thiadiazolyl, triazolyl, 1,2,3-oxadiazolyl, 1,2,4-oxadiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, 1,2,3-triazolyl, 1,2,4-triazolyl, 1,2,5-triazolyl, 1,3,4-triazolyl, benzofuranyl, benzothiofuranyl, indolyl, benzimidazolyl, benzoxazolyl, benzthiazolyl, indazolyl, benzisoxazolyl, benzisothiazolyl, and isoindazolyl;

alternatively, Y is selected from the following bicyclic heteroaryl ring systems:

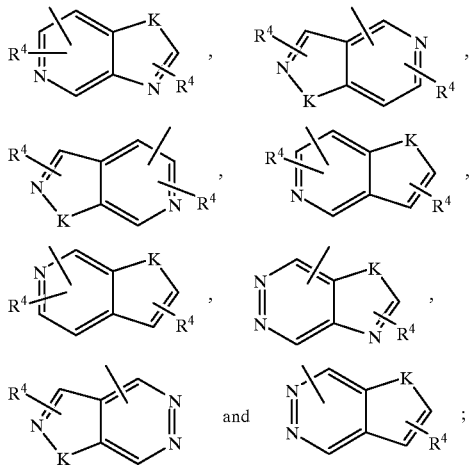

K is selected from O, S, NH, and N.

[3] In a more preferred embodiment, the present invention provides novel compounds of formulae Ia–Ib, wherein;

Z is selected from a C(O), $CH_2C(O)$, $C(O)CH_2$, NHC(O), C(O)NH, $C(O)N(CH_3)$, $CH_2S(O)_2$, $S(O)_2(CH_2)$, $SO_2NH$, and $NHSO_2$, provided that Z does not form a N—N or $NCH_2N$ bond with group A.

[4] In an even more preferred embodiment, the present invention provides novel compounds of formulae Ia–Ib, wherein;

E is phenyl substituted with R or 2-pyridyl substituted with R;

D is selected from $C(O)NH_2$, $C(=NH)NH_2$, $CH_2NH_2$, $CH_2NHCH_3$, $CH(CH_3)NH_2$, and $C(CH_3)_2NH_2$; and, R is selected from H, $OCH_3$, Cl, and F.

[5] In a further preferred embodiment, the present invention provides novel compounds of formulae Ia–Ib, wherein;

D—E is selected from 3-amidinophenyl, 3-aminomethylphenyl, 3-aminocarbonylphenyl, 3-(methylaminomethyl)phenyl, 3-(1-aminoethyl)phenyl, 3-(2-amino-2-propyl)phenyl, 4-chloro-3-amidinophenyl, 4-chloro-3-aminomethylphenyl, 4-chloro-3-(methylaminomethyl)phenyl, 4-fluoro-3-amidinophenyl, 4-fluoro-3-aminomethylphenyl, 4-fluoro-3-(methylaminomethyl)phenyl, 6-amidinopyrid-2-yl, 6-aminomethylpyrid-2-yl, 6-aminocarbonylpyrid-2-yl, 6-(methylaminomethyl)pyrid-2-yl, 6-(1-aminoethyl)pyrid-2-yl, and 6-(2-amino-2-propyl)pyrid-2-yl.

[6] In another even more preferred embodiment, the present invention provides novel compounds of formulae Ia–Ib, wherein;

Z is $C(O)CH_2$ and CONH, provided that Z does not form a N—N bond with group A;

A is selected from phenyl, pyridyl, and pyrimidyl, and is substituted with 0–2 $R^4$; and, B is selected from X—Y, phenyl, pyrrolidino, morpholino, 1,2,3-triazolyl, and imidazolyl, and is substituted with 0–1 $R^{4a}$;

$R^4$, at each occurrence, is selected from OH, $(CH_2)_rOR^2$, halo, $C_{1-4}$ alkyl, $(CH_2)_rNR^2R^{2a}$, and $(CF_2)_rCF_3$;

$R^{4a}$ is selected from $C_{1-4}$ alkyl, $CF_3$, $S(O)_pR^5$, $SO_2NR^2R^{2a}$, and 1-$CF_3$-tetrazol-2-yl;

$R^5$, at each occurrence, is selected from $CF_3$, $C_{1-6}$ alkyl, phenyl, and benzyl;

X is $CH_2$ or C(O); and,

Y is selected from pyrrolidino and morpholino.

[7] In another further preferred embodiment, the present invention provides novel compounds of formulae Ia–Ib, wherein;

A is selected from the group: phenyl, 2-pyridyl, 3-pyridyl, 2-pyrimidyl, 2-Cl-phenyl, 3-Cl-phenyl, 2-F-phenyl, 3-F-phenyl, 2-methylphenyl, 2-aminophenyl, and 2-methoxyphenyl; and, B is selected from the group: 2-$CF_3$-phenyl, 2-(aminosulfonyl)phenyl, 2-(methylaminosulfonyl) phenyl, 2-(dimethylaminosulfonyl)phenyl, 1-pyrrolidinocarbonyl, 2-(methylsulfonyl)phenyl, 4-morpholino, 2-(1'-$CF_3$-tetrazol-2-yl)phenyl, 4-morpholinocarbonyl, 2-methyl-1-imidazolyl, 5-methyl-1-imidazolyl, 2-methylsulfonyl-1-imidazolyl and, 5-methyl-1,2,3-triazolyl.

[8] In another even more preferred embodiment, the present invention provides novel compounds of formulae Ia–Ib, wherein;

E is phenyl substituted with R or 2-pyridyl substituted with R;

D is selected from $C(O)NH_2$, $C(=NH)NH_2$, $CH_2NH_2$, $CH_2NHCH_3$, $CH(CH_3)NH_2$, and $C(CH_3)_2NH_2$; and, R is selected from H, $OCH_3$, Cl, and F;

Z is $C(O)CH_2$ and CONH, provided that Z does not form a N—N bond with group A;

A is selected from phenyl, pyridyl, and pyrimidyl, and is substituted with 0–2 $R^4$; and, B is selected from X—Y, phenyl, pyrrolidino, morpholino, 1,2,3-triazolyl, and imidazolyl, and is substituted with 0–1 $R^{4a}$;

$R^4$, at each occurrence, is selected from OH, $(CH_2)_rOR^2$, halo, $C_{1-4}$ alkyl, $(CH_2)_rNR^2R^{2a}$, and $(CF_2)_rCF_3$;

$R^{4a}$ is selected from $C_{1-4}$ alkyl, $CF_3$, $S(O)_pR^5$, $SO_2NR^2R^{2a}$, and 1-$CF_3$-tetrazol-2-yl;

$R^5$, at each occurrence, is selected from $CF_3$, $C_{1-6}$ alkyl, phenyl, and benzyl;

X is $CH_2$ or C(O); and,

Y is selected from pyrrolidino and morpholino.

[9] In another further preferred embodiment, the present invention provides novel compounds of formulae Ia–Ib, wherein;

D—E is selected from 3-amidinophenyl, 3-aminomethylphenyl, 3-aminocarbonylphenyl, 3-(methylaminomethyl)phenyl, 3-(1-aminoethyl)

phenyl, 3-(2-amino-2-propyl)phenyl, 4-chloro-3-amidinophenyl, 4-chloro-3-aminomethylphenyl, 4-chloro-3-(methylaminomethyl)phenyl, 4-fluoro-3-amidinophenyl, 4-fluoro-3-aminomethylphenyl, 4-fluoro-3-(methylaminomethyl)phenyl, 6-amidinopyrid-2-yl, 6-aminomethylpyrid-2-yl, 6-aminocarbonylpyrid-2-yl, 6-(methylaminomethyl)pyrid-2-yl, 6-(1-aminoethyl)pyrid-2-yl, 6-(2-amino-2-propyl)pyrid-2-yl;

A is selected from the group: phenyl, 2-pyridyl, 3-pyridyl, 2-pyrimidyl, 2-Cl-phenyl, 3-Cl-phenyl, 2-F-phenyl, 3-F-phenyl, 2-methylphenyl, 2-aminophenyl, and 2-methoxyphenyl; and, B is selected from the group: 2-$CF_3$-phenyl, 2-(aminosulfonyl)phenyl, 2-(methylaminosulfonyl)phenyl, 2-(dimethylaminosulfonyl)phenyl, 1-pyrrolidinocarbonyl, 2-(methylsulfonyl)phenyl, 4-morpholino, 2-(1'-$CF_3$-tetrazol- 2-yl)phenyl, 4-morpholinocarbonyl, 2-methyl-1-imidazolyl, 5-methyl-1-imidazolyl, 2-methylsulfonyl-1-imidazolyl and, 5-methyl-1,2,3-triazolyl.

[10] In a still further preferred embodiment, the present invention provides a novel compound of formula Ia.

[11] In another still further preferred embodiment, the present invention provides a novel compound of formula Ib.

[12] In another even more preferred embodiment, the present invention provides novel compounds of formulae Ia–Ib, wherein;

D is selected from $C(=NR^8)NR^7R^9$, $C(O)NR^7R^8$, $NR^7R^8$, and $CH_2NR^7R^8$;

E is phenyl substituted with R or pyridyl substituted with R;

R is selected from H, Cl, F, $OR^3$, $CH_3$, $CH_2CH_3$, $OCF_3$, and $CF_3$;

Z is selected from C(O), $CH_2C(O)$, $C(O)CH_2$, NHC(O), and C(O)NH, provided that Z does not form a N—N bond with group A;

$R^{1a}$ and $R^{1b}$ are, at each occurrence, independently selected from H, —$(CH_2)_r$—$R^{1'}$, $NCH_2R^{1''}$, $OCH_2R^{1''}$, $SCH_2R^{1''}$, $N(CH_2)_2(CH_2)_rR^{1'}$, $O(CH_2)_2(CH_2)_rR^{1'}$, and $S(CH_2)_2(CH_2)_rR^{1'}$;

$R^{1c}$ is selected from H, —$(CH_2)_q$—$R^{1'}$, $C_{1-3}$ alkyl, $C(O)R^{2c}$, $(CF_2)_rCO_2R^{2c}$, and $C(O)NR^2R^{2a}$;

$R^{1'}$, at each occurrence, is selected from H, $C_{1-3}$ alkyl, halo, $(CF_2)_rCF_3$, $OR^2$, $NR^2R^{2a}$, $C(O)R^{2c}$, $(CF_2)_rCO_2R^{2c}$, $S(O)_pR^{2b}$, $NR^2(CH_2)_rOR^2$, $NR^2C(O)R^{2b}$, $NR^2C(O)_2R^{2b}$, $C(O)NR^2R^{2a}$, $SO_2NR^2R^{2a}$, and $NR^2SO_2R^{2b}$;

A is selected from one of the following carbocyclic and heterocyclic systems which are substituted with 0–2 $R^4$;
 phenyl, piperidinyl, piperazinyl, pyridyl, pyrimidyl, furanyl, morpholinyl, thiophenyl, pyrrolyl, pyrrolidinyl, oxazolyl, isoxazolyl, thiazolyl, isothiazolyl, pyrazolyl, and imidazolyl;

B is selected from: Y, X—Y, $NR^2R^{2a}$, $C(=NR^2)NR^2R^{2a}$, and $NR^2C(=NR^2)NR^2R^{2a}$;

X is selected from $CH_2$, —$CR^2(CR^2R^{2b})(CH_2)_t$—, —C(O)—, —C(=NR)—, —CH($NR^2R^{2a}$)—, —C(O)$NR^2$—, —$NR^2C(O)$—, —$NR^2C(O)NR^2$—, —$NR^2$—, and O;

Y is $NR^2R^{2a}$, provided that X—Y do not form a N—N or O—N bond;

alternatively, Y is selected from one of the following carbocyclic and heterocyclic systems which are substituted with 0–2 $R^{4a}$;

phenyl, piperidinyl, piperazinyl, pyridyl, pyrimidyl, furanyl, morpholinyl, thiophenyl, pyrrolyl, pyrrolidinyl, oxazolyl, isoxazolyl, isoxazolinyl, thiazolyl, isothiazolyl, pyrazolyl, imidazolyl, oxadiazolyl, thiadiazolyl, triazolyl, 1,2,3-oxadiazolyl, 1,2,4-oxadiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, 1,2,3-triazolyl, 1,2,4-triazolyl, 1,2,5-triazolyl, and 1,3,4-triazolyl;

$R^4$, at each occurrence, is selected from =O, OH, Cl, F, $C_{1-4}$ alkyl, $(CH_2)_rNR^2R^{2a}$, $(CH_2)_rC(O)R^{2b}$, $NR^2C(O)R^{2b}$, $C(O)NR^2R^{2a}$, $CH(=NH)NH_2$, $NHC(=NH)NH_2$, $SO_2NR^2R^{2a}$, $NR^2SO_2$-$C_{1-4}$ alkyl, $NR^2SO_2R^5$, $S(O)_pR^5$, and $(CF_2)_rCF_3$;

$R^{4a}$, at each occurrence, is selected from =O, OH, Cl, F, $C_{1-4}$ alkyl, $(CH_2)_rNR^2R^{2a}$, $(CH_2)_rC(O)R^{2b}$, $NR^2C(O)R^{2b}$, $C(O)NR^2R^{2a}$, $CH(=NH)NH_2$, $NHC(=NH)NH_2$, $SO_2NR^2R^{2a}$, $NR^2SO_2$-$C_{1-4}$ alkyl, $NR^2SO_2R^5$, $S(O)_pR^5$, $(CF_2)_rCF_3$, and 1-$CF_3$-tetrazol-2-yl;

$R^5$, at each occurrence, is selected from $CF_3$, $C_{1-6}$ alkyl, phenyl substituted with 0–2 $R^6$, and benzyl substituted with 0–2 $R^6$;

$R^6$, at each occurrence, is selected from H, =O, OH, $OR^2$, Cl, F, $CH_3$, CN, $NO_2$, $(CH_2)_rNR^2R^{2a}$, $(CH_2)_rC(O)R^{2b}$, $NR^2C(O)R^{2b}$, $CH(=NH)NH_2$, $NHC(=NH)NH_2$, and $SO_2NR^2R^{2a}$;

$R^7$, at each occurrence, is selected from H, OH, $C_{1-6}$ alkyl, $C_{1-6}$ alkylcarbonyl, $C_{1-6}$ alkoxy, $C_{1-4}$ alkoxycarbonyl, benzyl, $C_{6-10}$ aryloxy, $C_{6-10}$ aryloxycarbonyl, $C_{6-10}$ arylmethylcarbonyl, $C_{1-4}$ alkylcarbonyloxy $C_{1-4}$ alkoxycarbonyl, $C_{6-10}$ arylcarbonyloxy $C_{1-4}$ alkoxycarbonyl, $C_{1-6}$ alkylaminocarbonyl, phenylaminocarbonyl, and phenyl $C_{1-4}$ alkoxycarbonyl;

$R^8$, at each occurrence, is selected from H, $C_{1-6}$ alkyl and benzyl; and alternatively, $R^7$ and $R^8$ combine to form a morpholino group; and, $R^9$, at each occurrence, is selected from H, $C_{1-6}$ alkyl and benzyl.

[13] In a another further preferred embodiment, the present invention provides novel compounds of formulae Ia–Ib, wherein;

E is phenyl substituted with R or 2-pyridyl substituted with R;

R is selected from H, Cl, F, $OCH_3$, $CH_3$, $OCF_3$, and $CF_3$;

Z is selected from a $C(O)CH_2$ and C(O)NH, provided that Z does not form a N—N bond with group A;

$R^{1a}$, at each occurrence, is selected from H, $CH_3$, $CH_2CH_3$, Cl, F, $CF_3$, $OCH_3$, $NR^2R^{2a}$, $S(O)_pR^{2b}$, $CH_2S(O)_pR^{2b}$, $CH_2NR^2S(O)_pR^{2b}$, $C(O)R^{2c}$, $CH_2C(O)R^{2c}$, $C(O)NR^2R^{2a}$, and $SO_2NR^2R^{2a}$;

$R^{1b}$ is selected from H, $CH_3$, $CH_2CH_3$, Cl, F, $CF_3$, $OCH_3$, $NR^2R^{2a}$, $S(O)_pR^{2b}$, $CH_2S(O)_pR^{2b}$, $CH_2NR^2S(O)_pR^{2b}$, $C(O)R^{2c}$, $CH_2C(O)R^{2c}$, $C(O)NR^2R^{2a}$, and $SO_2NR^2R^{2a}$;

$R^{1c}$ is selected from H, $CH_3$, $CH_2CH_3$, $CF_3$, $CH_2S(O)_p^{2b}$, $CH_2NR^2S(O)_pR^{2b}$, $C(O)R^{2c}$, $CH_2C(O)R^{2c}$, and $C(O)NR^2R^{2a}$;

A is selected from one of the following carbocyclic and heterocyclic systems which are substituted 0–2 $R^4$;
 phenyl, pyridyl, pyrimidyl, furanyl, thiophenyl, pyrrolyl, oxazolyl, isoxazolyl, thiazolyl, isothiazolyl, pyrazolyl, and imidazolyl;

B is selected from: Y and X—Y;

X is selected from $CH_2$, $—CR^2(CR^2R^{2b})—$, $—C(O)—$, $—C(=NR)—$, $—CH(NR^2R^{2a})—$, $—C(O)NR^2—$, $—NR^2C(O)—$, $—NR^2C(O)NR^2—$, $—NR^2—$, and O;

Y is $NR^2R^{2a}$, provided that X—Y do not form a N—N or O—N bond;

alternatively, Y is selected from one of the following carbocyclic and heterocyclic systems which are substituted with 0–2 $R^{4a}$;
phenyl, piperidinyl, piperazinyl, pyridyl, pyrimidyl, furanyl, morpholinyl, thiophenyl, pyrrolyl, pyrrolidinyl, oxazolyl, isoxazolyl, isoxazolinyl, thiazolyl, isothiazolyl, pyrazolyl, imidazolyl, oxadiazolyl, thiadiazolyl, triazolyl, 1,2,3-oxadiazolyl, 1,2,4-oxadiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, 1,2,3-triazolyl, 1,2,4-triazolyl, 1,2,5-triazolyl, and 1,3,4-triazolyl;

$R^2$, at each occurrence, is selected from H, $CF_3$, $CH_3$, benzyl, and phenyl;

$R^{2a}$, at each occurrence, is selected from H, $CF_3$, $CH_3$, benzyl, and phenyl;

$R^{2b}$, at each occurrence, is selected from $CF_3$, $OCH_3$, $CH_3$, benzyl, and phenyl;

$R^{2c}$, at each occurrence, is selected from $CF_3$, OH, $OCH_3$, $CH_3$, benzyl, and phenyl;

alternatively, $R^2$ and $R^{2a}$ combine to form a 5 or 6 membered saturated, partially unsaturated, or unsaturated ring which contains from 0–1 additional heteroatoms selected from the group consisting of N, O, and S;

$R^3$, at each occurrence, is selected from H, $CH_3$, $CH_2CH_3$, and phenyl;

$R^{3a}$, at each occurrence, is selected from H, $CH_3$, $CH_2CH_3$, and phenyl;

$R^4$, at each occurrence, is selected from OH, Cl, F, $CH_3$, $CH_2CH_3$, $NR^2R^{2a}$, $CH_2NR^2R^{2a}$, $C(O)R^{2b}$, $NR^2C(O)R^{2b}$, $C(O)NR^2R^{2a}$, and $CF_3$;

$R^{4a}$, at each occurrence, is selected from OH, Cl, F, $CH_3$, $CH_2CH_3$, $NR^2R^{2a}$, $CH_2NR^2R^{2a}$, $C(O)R^{2b}$, $C(O)NR^2R^{2a}$, $SO_2NR^2R^{2a}$, $S(O)_pR^5$, $CF_3$, and 1-$CF_3$-tetrazol-2-yl;

$R^5$, at each occurrence, is selected from $CF_3$, $C_{1-6}$ alkyl, phenyl substituted 0–2 $R^6$, and benzyl substituted with 1 $R^6$;

$R^6$, at each occurrence, is selected from H, OH, $OCH_3$, Cl, F, $CH_3$, CN, $NO_2$, $NR^2R^{2a}$, $CH_2NR^2R^{2a}$, and $SO_2NR^2R^{2a}$;

$R^7$, at each occurrence, is selected from H, OH, $C_{1-3}$ alkyl, $C_{1-3}$ alkylcarbonyl, $C_{1-3}$ alkoxy, $C_{1-4}$ alkoxycarbonyl, benzyl, phenoxy, phenoxycarbonyl, benzylcarbonyl, $C_{1-4}$ alkylcarbonyloxy $C_{1-4}$ alkoxycarbonyl, phenylcarbonyloxy $C_{1-4}$ alkoxycarbonyl, $C_{1-6}$ alkylaminocarbonyl, phenylaminocarbonyl, and phenyl $C_{1-4}$ alkoxycarbonyl;

$R^8$, at each occurrence, is selected from H, $CH_3$, and benzyl; and, alternatively, $R^7$ and $R^8$ combine to form a morpholino group;

$R^9$, at each occurrence, is selected from H, $CH_3$, and benzyl.

[14] In a another still further preferred embodiment, the present invention provides novel compounds of formulae Ia–Ib, wherein;

$R^{1a}$, at each occurrence, is selected from H, $CH_3$, $CH_2CH_3$, Cl, F, $CF_3$, $OCH_3$, $NR^2R^{2a}$, $S(O)_pR^{2b}$, $C(O)NR^2R^{2a}$, $CH_2S(O)_pR^{2b}$, $CH_2NR^2S(O)_pR^{2b}$, $C(O)R^{2c}$, $CH_2C(O)R^{2c}$, and $SO_2NR^2R^{2a}$;

$R^{1b}$ is selected from H, $CH_3$, $CH_2CH_3$, Cl, F, $CF_3$, $OCH_3$, $NR^2R^{2a}$, $S(O)_pR^{2b}$, $C(O)NR^2R^{2a}$, $CH_2S(O)_pR^{2b}$, $CH_2NR^2S(O)_pR^{2b}$, $C(O)R^{2b}$, $CH_2C(O)R^{2b}$, and $SO_2NR^2R^{2a}$;

$R^{1c}$ is selected from H, $CH_3$, $CH_2CH_3$, $CF_3$, $C(O)NR^2R^{2a}$, $CH_2S(O)_pR^{2b}$, $CH_2NR^2S(O)_pR^{2b}$, $C(O)R^{2b}$, and $CH_2C(O)R^{2b}$;

A is selected from one of the following carbocyclic and heterocyclic systems which are substituted 0–2 $R^4$;
phenyl, pyridyl, and pyrimidyl;

B is selected from: Y and X—Y;

X is selected from —C(O)— and O;

Y is $NR^2R^{2a}$, provided that X—Y do not form a O—N bond;

alternatively, Y is selected from one of the following carbocyclic and heterocyclic systems which are substituted with 0–2 $R^{4a}$;
phenyl, piperazinyl, pyridyl, pyrimidyl, morpholinyl, pyrrolidinyl, imidazolyl, and 1,2,3-triazolyl;

$R^2$, at each occurrence, is selected from H, $CF_3$, $CH_3$, benzyl, and phenyl;

$R^{2a}$, at each occurrence, is selected from H, $CF_3$, $CH_3$, benzyl, and phenyl;

$R^{2b}$, at each occurrence, is selected from $CF_3$, $OCH_3$, $CH_3$, benzyl, and phenyl;

$R^{2c}$, at each occurrence, is selected from $CF_3$, OH, $OCH_3$, $CH_3$, benzyl, and phenyl;

alternatively, $R^2$ and $R^{2a}$ combine to form a ring system selected from pyrrolidinyl, piperazinyl and morpholino;

$R^4$, at each occurrence, is selected from Cl, F, $CH_3$, $NR^2R^{2a}$, and $CF_3$;

$R^{4a}$, at each occurrence, is selected from Cl, F, $CH_3$, $SO_2NR^2R^{2a}$, $S(O)_pR^5$, and $CF_3$; and, $R^5$, at each occurrence, is selected from $CF_3$ and $CH_3$.

[15] Specifically preferred compounds of the present invention are selected from the group:

1-(3-amidinophenyl)-5-[[(2'-methylsulfonyl-[1,1']-biphen-4-yl)-aminocarbonyl]-3-trifluoromethyl-pyrazoline; and, 1-(3-aminomethylphenyl)-5-[[(2'-methylsulfonyl-[1,1']-biphen-4-yl)-aminocarbonyl]-3-trifluoromethyl-pyrazoline;

and pharmaceutically acceptable salts thereof.

In a second embodiment, the present invention provides novel pharmaceutical compositions, comprising: a pharmaceutically acceptable carrier and a therapeutically effective amount of a compound of formula (I) or a pharmaceutically acceptable salt form thereof.

In a third embodiment, the present invention provides a novel method for treating or preventing a thromboembolic disorder, comprising: administering to a patient in need thereof a therapeutically effective amount of a compound of formula (I) or a pharmaceutically acceptable salt form thereof.

DEFINITIONS

The compounds herein described may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated.

The term "substituted," as used herein, means that any one or more hydrogens on the designated atom is replaced with a selection from the indicated group, provided that the designated atom's normal valency is not exceeded, and that the substitution results in a stable compound. When a substitent is keto (i.e., =O), then 2 hydrogens on the atom are replaced.

When any variable (e.g., $R^6$) occurs more than one time in any constituent or formula for a compound, its definition at each occurrence is independent of its definition at every other occurrence. Thus, for example, if a group is shown to be substituted 0–2 $R^6$, then said group may optionally be substituted with up to two $R^6$ groups and $R^6$ at each occurrence is selected independently from the definition of $R^6$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

As used herein, "$C_{1-6}$ alkyl" is intended to include both branched and straight-chain saturated aliphatic hydrocarbon groups having the specified number of carbon atoms, examples of which include, but are not limited to, methyl, ethyl, n-propyl, i-propyl, n-butyl, i-butyl, sec-butyl, t-butyl, pentyl, and hexyl; "Alkenyl" is intended to include hydrocarbon chains of either a straight or branched configuration and one or more unsaturated carbon—carbon bonds which may occur in any stable point along the chain, such as ethenyl, propenyl, and the like.

"Halo" or "halogen" as used herein refers to fluoro, chloro, bromo, and iodo; and "counterion" is used to represent a small, negatively charged species such as chloride, bromide, hydroxide, acetate, sulfate, and the like.

As used herein, "carbocycle" or "carbocyclic residue" is intended to mean any stable 3- to 7-membered monocyclic or bicyclic or 7- to 13-membered bicyclic or tricyclic, any of which may be saturated, partially unsaturated, or aromatic. Examples of such carbocycles include, but are not limited to, cyclopropyl, cyclobutyl, cyclopentyl, cyclohexyl, cycloheptyl, adamantyl, cyclooctyl, [3.3.0]bicyclooctane, [4.3.0]bicyclononane, [4.4.0]bicyclodecane (decalin), [2.2.2]bicyclooctane, fluorenyl, phenyl, naphthyl, indanyl, adamantyl, or tetrahydronaphthyl (tetralin).

As used herein, the term "heterocycle" or "heterocyclic system" is intended to mean a stable 5- to 7-membered monocyclic or bicyclic or 7- to 10-membered bicyclic heterocyclic ring which is saturated partially unsaturated or unsaturated (aromatic), and which consists of carbon atoms and from 1 to 4 heteroatoms independently selected from the group consisting of N, O and S and including any bicyclic group in which any of the above-defined heterocyclic rings is fused to a benzene ring. The nitrogen and sulfur heteroatoms may optionally be oxidized. The heterocyclic ring may be attached to its pendant group at any heteroatom or carbon atom which results in a stable structure. The heterocyclic rings described herein may be substituted on carbon or on a nitrogen atom if the resulting compound is stable. If specifically noted, a nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. As used herein, the term "aromatic heterocyclic system" is intended to mean a stable 5- to 7-membered monocyclic or bicyclic or 7- to 10-membered bicyclic heterocyclic aromatic ring which consists of carbon atoms and from 1 to 4 heterotams independently selected from the group consisting of N, O and S. It is preferred that the total number of S and O atoms in the aromatic heterocycle is not more than 1.

Examples of heterocycles include, but are not limited to, 1H-indazole, 2-pyrrolidonyl, 2H,6H-1,5,2-dithiazinyl, 2H-pyrrolyl, 3H-indolyl, 4-piperidonyl, 4aH-carbazole, 4H-quinolizinyl, 6H-1,2,5-thiadiazinyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazalonyl, carbazolyl, 4aH-carbazolyl, β-carbolinyl, chromanyl, chromenyl, cinnolinyl, decahydroquinolinyl, 2H,6H-1,5,2-dithiazinyl, dihydrofuro [2,3-b]tetrahydrofuran, furanyl, furazanyl, imidazolidinyl, imidazolinyl, imidazolyl, 1H-indazolyl, indolenyl, indolinyl, indolizinyl, indolyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinylperimidinyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, piperidonyl, 4-piperidonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, 4H-quinolizinyl, quinoxalinyl, quinuclidinyl, carbolinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, xanthenyl. Preferred heterocycles include, but are not limited to, pyridinyl, furanyl, thienyl, pyrrolyl, pyrazolyl, imidazolyl, indolyl, benzimidazolyl, 1H-indazolyl, oxazolidinyl, benzotriazolyl, benzisoxazolyl, oxindolyl, benzoxazolinyl, or isatinoyl. Also included are fused ring and spiro compounds containing, for example, the above heterocycles.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 17th ed., Mack Publishing Company, Easton, Pa., 1985, p. 1418, the disclosure of which is hereby incorporated by reference.

"Prodrugs" are intended to include any covalently bonded carriers which release the active parent drug according to formula (I) in vivo when such prodrug is administered to a mammalian subject. Prodrugs of a compound of formula (I) are prepared by modifying functional groups present in the compound in such a way that the modifications are cleaved, either in routine manipulation or in vivo, to the parent compound. Prodrugs include compounds of formula (I) wherein a hydroxy, amino, or sulfhydryl group is bonded to any group that, when the prodrug or compound of formula (I) is administered to a mammalian subject, cleaves to form a free hydroxyl, free amino, or free sulfhydryl group, respectively. Examples of prodrugs include, but are not limited to, acetate, formate and benzoate derivatives of alcohol and amine functional groups in the compounds of formula (I), and the like. Preferred prodrugs are amidine prodrugs wherein D is $C(=NR^7)NH_2$ or its tautomer $C(=NH)NHR^7$ and $R^7$ is selected from OH, $C_{1-4}$ alkoxy, $C_{6-10}$ aryloxy, $C_{1-4}$ alkoxycarbonyl, $C_{6-10}$ aryloxycarbonyl, $C_{6-10}$ arylmethylcarbonyl, $C_{1-4}$ alkylcarbonyloxy $C_{1-4}$ alkoxycarbonyl, and $C_{6-10}$ arylcarbonyloxy $C_{1-4}$ alkoxycarbonyl. More preferred prodrugs are where $R^7$ is OH, methoxy, ethoxy, benzyloxycarbonyl, methoxycarbonyl, and methylcarbonyloxymethoxycarbonyl.

"Stable compound" and "stable structure" are meant to indicate a compound that is sufficiently robust to survive isolation to a useful degree of purity from a reaction mixture, and formulation into an efficacious therapeutic agent.

SYNTHESIS

The compounds of the present invention can be prepared in a number of ways known to one skilled in the art of organic synthesis. The compounds of the present invention can be synthesized using the methods described below, together with synthetic methods known in the art of synthetic organic chemistry, or by variations thereon as appreciated by those skilled in the art. Preferred methods include, but are not limited to, those described below. The reactions are performed in a solvent appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention. It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene and Wuts (*Protective Groups In Organic Synthesis*, Wiley and Sons, 1991). All references cited herein are hereby incorporated in their entirety herein by reference.

Pyrazolines of this invention can be easily prepared via [3+2] cycloaddition of bromo or chloro hydrazone with an appropriate acrylate according to the methodology described by Tewari R. S. and Parihar *Tetrahedron* 1983, 39, 129–136, or Krayushkin, M. M. et. al *Izv. Akad. Nauk, Ser. Khim.* 1994, 1, 114–117.

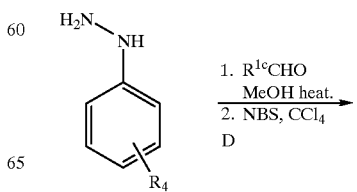

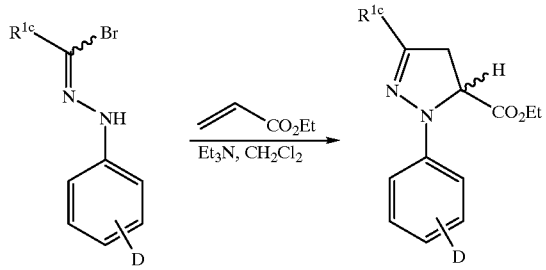

Pyrazoline 5-esters can also be prepared by the treatment of an appropriately substituted hydrazone with lead tetraacetate and an appropriate acrylate in a THF/benzene solvent system according to the procedure of Sasaki T, et. al. *Bull. Chem Soc. Jpn.* 1970, 43, 1254.

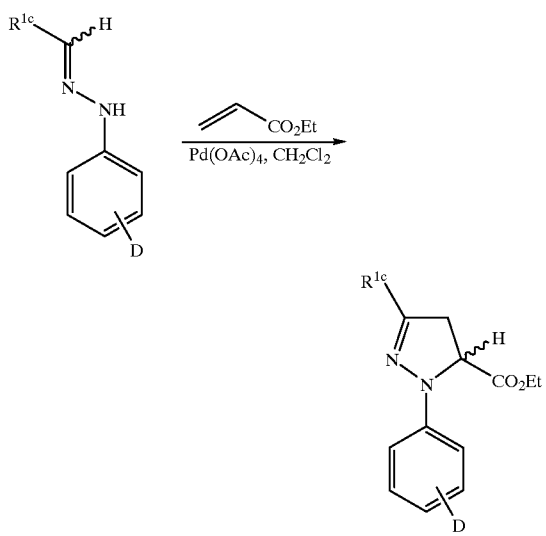

Another method of obtaining pyrazoline 5-esters is the condensation of an appropriate phenyl or heteroaryl hydrazine with an approptiate 2-oxoglutaconate according to Blitzke, T. et. al. *J. Prakt. Chem.* 1993, 335(8), 683.

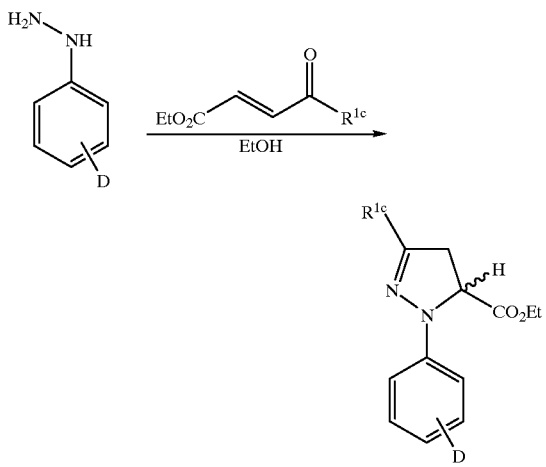

Alternatively the pyrazoline ester can be prepared by treatment of a diazo-trifluoromethyl derivative with excess acrylate or acrolein in the presence of excess pyridine (Doyle, M. O. et. al. *J. Heterocyclic Chem.* 1983, 20, 943).

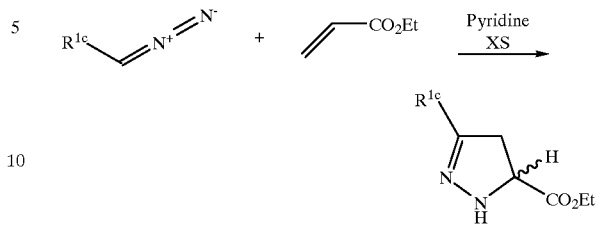

Cycloadditions as described above but with di-substituted olefins should result in the formation of regio-adducts which can be easily separated by standard chromatographic techniques.

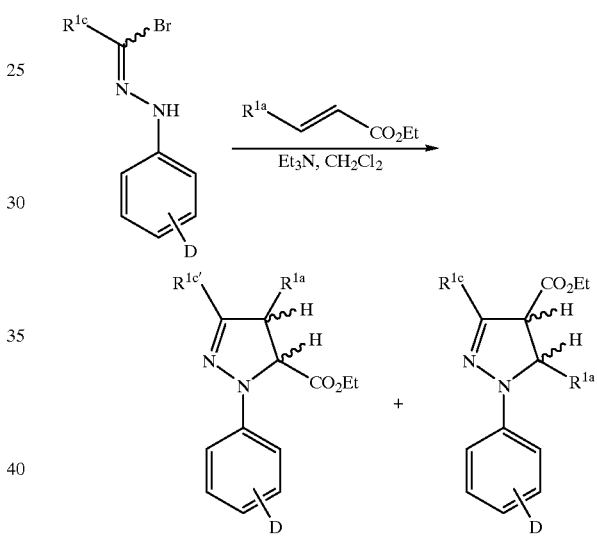

It is understood by those in the art of organic synthesis that such cycloadditions can also be carried out with a wide variety of electron withdrawing olefins with functionalities such as nitro, sulfonyl, sulfonamido, nitrile, phosphate etc. These in turn can be derivatized to appropriate compounds of the present invention.

The pyrazoline carboxyesters obtained via any of the above mentioned methodologies can be converted to the amide derivatives via the acid, acid chloride coupling methodlogies or a direct Weinreb (trimethylaluminum, aniline in dichloromethane) coupling technique known to those in the art of organic synthesis. A variety of anilines or amines can be coupled via these methodologies to afford the desired compounds.

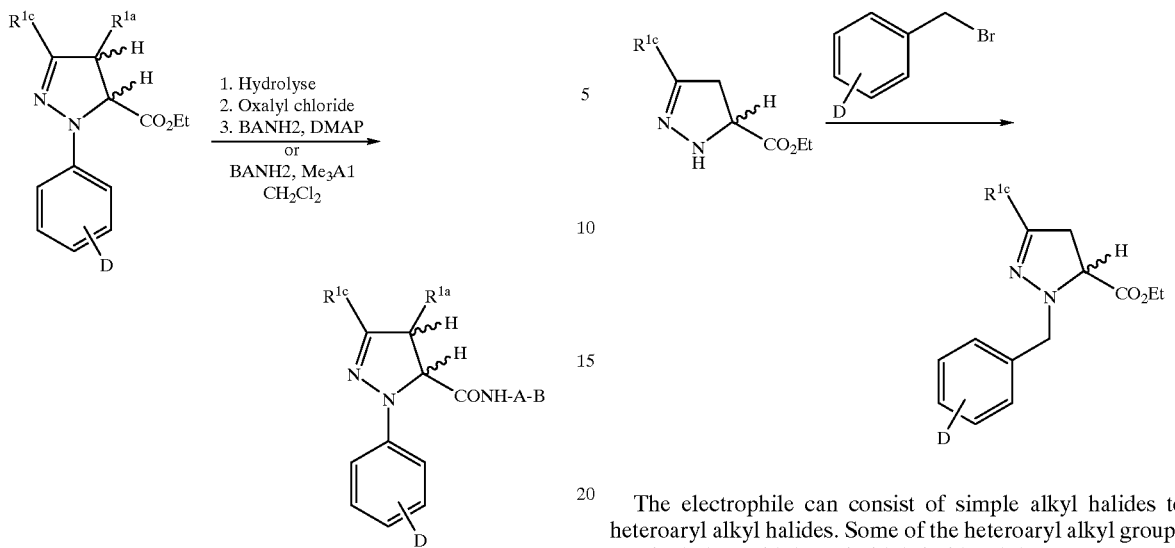

Alternatively the ester can be hydrolysed and converted to an amino functionality via the Curtius rearrangement. This in turn can be derivatised to obtain an amido, sulfonamido or urea derivative.

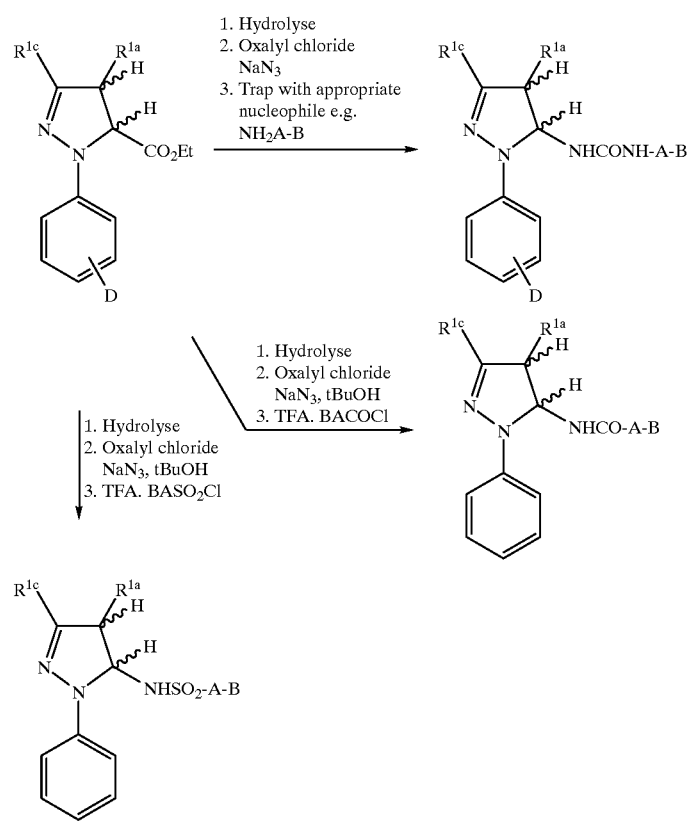

Pyrazolines wherein s is other than 0 can be prepared by alkylation of an appropriate pyrazoline.

The electrophile can consist of simple alkyl halides to heteroaryl alkyl halides. Some of the heteroaryl alkyl groups can include pyridyl, pyrimidyl, imidazolyl etc.

In cases wherein D is a nitrile can be further converted to an amidine functionality via the standard Pinner-amidine reaction sequence known to those in the art or can be converted to the benzylamine via reduction in an acidic media or can be converted to the secondary and tertiary amine via the DIBAH/MeMgCl or MeMgBr/CeCl$_3$ methodologies outlined below.

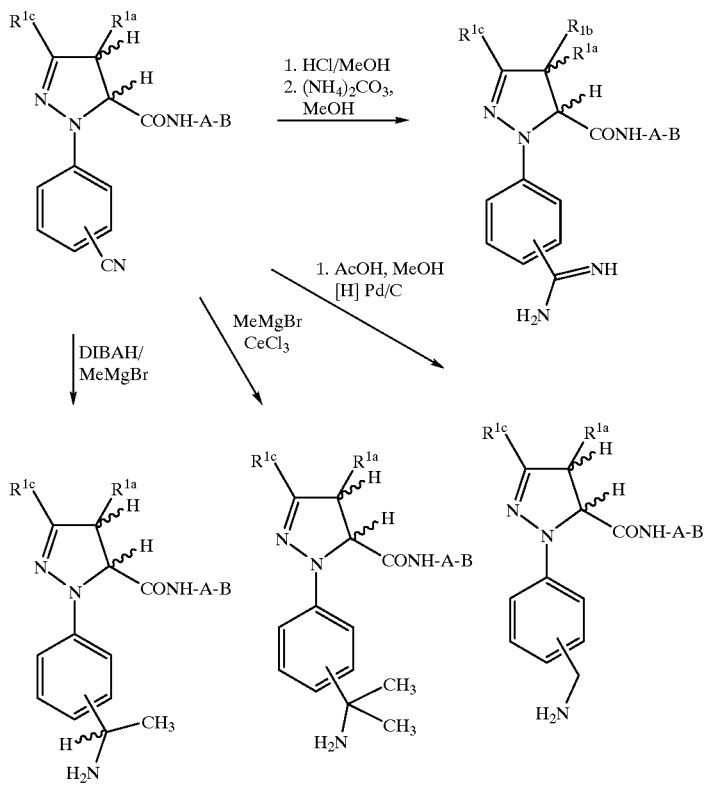

Compounds wherein D is a nitro can be reduced under catalytic Pd/C/MeOH techniques or $SnCl_2$/EtOAc or Zn/AcOH conditions to afford the desired amino derivatives.

Enantiomers of the pyrazolines can be easily obtained either via lipase hydrolysis of its esters or resolution with common chiral bases known to those in the art.

1,2,3-Triazolines can be synthesized via the cycloaddition methodology however in this case the dipole is an aryl azide and the dipolarophile is a variety of olefins bearing an electron withdrawing group such as an ester, amide or sulfonamide.

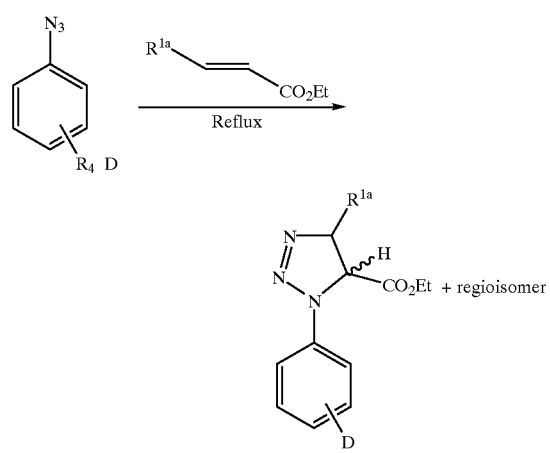

1,2,4-Triazolines can be prepared via the methods of Sandhy J. S. et. al. *Heterocycles* 1985, 23(5), 1143, and *Heterocycles* 1985, 23(5), 1123, by the method described in the scheme below.

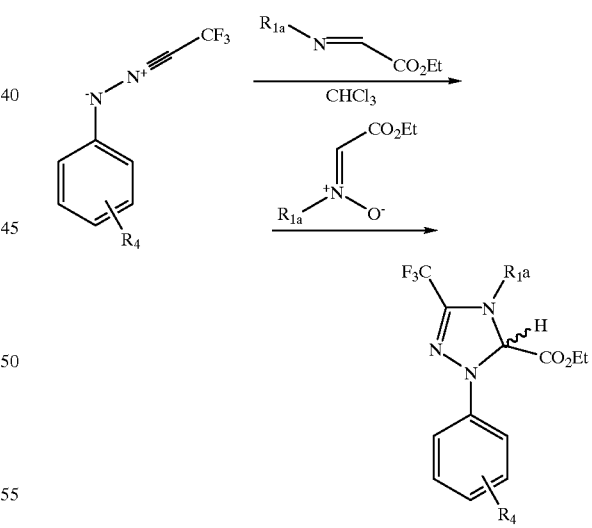

The triazoline esters can then subjected to the standard coupling procedures discussed above to afford the desired amide analogs. These can then further modified to the prepare compounds of the present invention.

Compounds of the present invention wherein AB is a biphenylamine or similar amine may be prepared as shown in the following scheme. 4-Bromoaniline can be protected as Boc-derivative and coupled to a phenylboronic acid under Suzuki conditions (*Bioorg. Med. Chem. Lett.* 1994, 189).

Deprotection with TFA provides the aminobiphenyl compound. Other similar amines wherein A and/or B are heterocycles can be prepared by the same method using appropiately substituted boronic acids and arylbromide. The bromoaniline can also be linked to the core ring structures first as described above, and then undergo a Suzuki reaction to give the desired product.

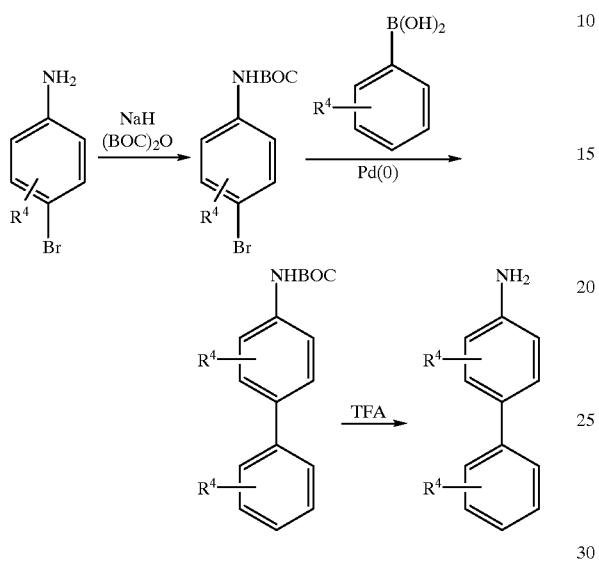

Compounds of the present invention wherein A—B is A—X—Y can be prepared like the piperazine derivative :3shown below.

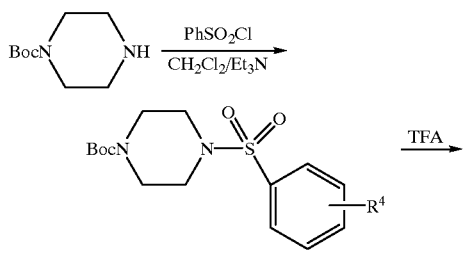

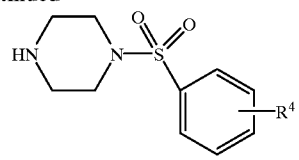

The following scheme shows how one can couple cyclic groups wherein X=NH, O, or S.

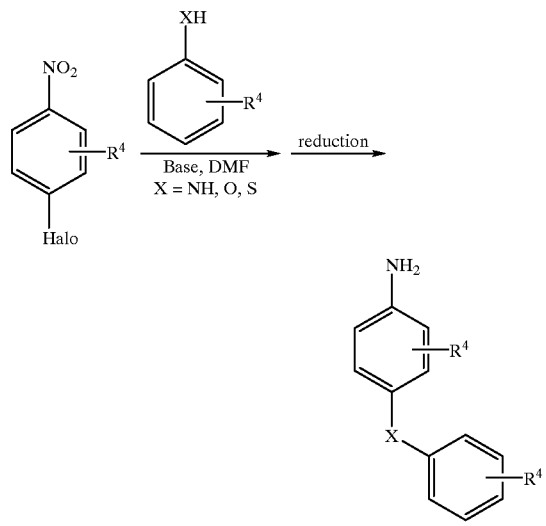

When B is defined as X—Y, the following description applies. Groups A and B are available either through commercial sources, known in the literature or readily synthesized by the adaptation of standard procedures known to practioners skilled in the art of organic synthesis. The required reactive functional groups appended to analogs of A and B are also available either through commercial sources, known in the literature or readily synthesized by the adaptation of standard procedures known to practioners skilled in the art of organic synthesis. In the tables that follow the chemistry required to effect the coupling of A to B is outlined.

TABLE A

Preparation of Amide, Ester, Urea, Sulfonamide and Sulfamide linkages between A and B.

| Rxn. No. | if A contains: | then the reactive substituent of Y is: | to give the following product A—X—Y: |
|---|---|---|---|
| 1 | A—$NHR^2$ as a substituent | ClC(O)—Y | A—$NR^2$—C(O)—Y |
| 2 | a secondary NH as part of a ring or chain | ClC(O)—Y | A—C(O)—Y |
| 3 | A—OH as a substituent | ClC(O)—Y | A—O—C(O)—Y |
| 4 | A—$NHR^2$ as a substituent | ClC(O)—$CR^2R^{2a}$—Y | A—$NR^2$—C(O)—$CR^2R^{2a}$—Y |
| 5 | a secondary NH as part of a ring or chain | ClC(O)—$CR^2R^{2a}$—Y | A—C(O)—$CR^2R^{2a}$—Y |

TABLE A-continued

Preparation of Amide, Ester, Urea,
Sulfonamide and Sulfamide linkages between A and B.

| Rxn. No. | if A contains: | then the reactive substituent of Y is: | to give the following product A—X—Y: |
|---|---|---|---|
| 6 | A—OH as a substituent | ClC(O)—CR$^2$R$^{2a}$—Y | A—O—C(O)CR$^2$R$^{2a}$—Y |
| 7 | A—NHR$^3$ as a substituent | ClC(O)NR$^2$—Y | A—NR$^2$—C(O)NR$^2$—Y |
| 8 | a secondary NH as part of a ring or chain | ClC(O)NR$^2$—Y | A—C(O)NR$^2$—Y |
| 9 | A—OH as a substituent | ClC(O)NR$^2$—Y | A—O—C(O)NR$^2$—Y |
| 10 | A—NHR$^2$ as a substituent | ClSO$_2$—Y | A—NR$^2$—SO$_2$—Y |
| 11 | a secondary NH as part of a ring or chain | ClSO$_2$—Y | A—SO$_2$—Y |
| 12 | A—NHR$^2$ as a substituent | ClSO$_2$—CR$^2$R$^{2a}$—Y | A—NR$^2$—SO$_2$—CR$^2$R$^{2a}$—Y |
| 13 | a secondary NH as part of a ring or chain | ClSO$_2$—CR$^2$R$^{2a}$—Y | A—SO$_2$—CR$^2$R$^{2a}$—Y |
| 14 | A—NHR$^2$ as a substituent | ClSO$_2$—NR$^2$—Y | A—NR$^2$—SO$_2$—NR$^2$—Y |
| 15 | a secondary NH as part of a ring or chain | ClSO$_2$—NR$^2$—Y | A—SO$_2$—NR$^2$—Y |
| 16 | A—C(O)Cl | HO—Y as a substituent | A—C(O)—O—Y |
| 17 | A—C(O)Cl | NHR$^2$—Y as a substituent | A—C(O)—NR$^2$—Y |
| 18 | A—C(O)Cl | a secondary NH as part of a ring or chain | A—C(O)—Y |
| 19 | A—CR$^2$R$^{2a}$C(O)Cl | HO—Y as a substituent | A—CR$^2$R$^{2a}$C(O)—O—Y |
| 20 | A—CR$^2$R$^{2a}$C(O)Cl | NHR$^2$—Y as a substituent | A—CR$^2$R$^{2a}$C(O)—NR$^2$—Y |
| 21 | A—CR$^2$R$^{2a}$C(O)Cl | a secondary NH as part of a ring or chain | A—CR$^2$R$^{2a}$C(O)—Y |
| 22 | A—SO$_2$Cl | NHR$^2$—Y as a substituent | A—SO$_2$—NR$^2$—Y |
| 23 | A—SO$_2$Cl | a secondary NH as part of a ring or chain | A—SO$_2$—Y |
| 24 | A—CR$^2$R$^{2a}$SO$_2$Cl | NHR$^2$—Y as a substituent | A—CR$^2$R$^{2a}$SO$_2$—NR$^2$—Y |
| 25 | A—CR$^2$R$^{2a}$SO$_2$Cl | a secondary NH as part of a ring or chain | A—CR$^2$R$^{2a}$SO$_2$—Y |

The chemistry of Table A can be carried out in aprotic solvents such as a chlorocarbon, pyridine, benzene or toluene, at temperatures ranging from −20° C. to the reflux point of the solvent and with or without a trialkylamine base.

TABLE B

Preparation of ketone linkages between A and B.

| Rxn. No. | if A contains: | then the reactive substituent of Y is: | to give the following product A—X—Y: |
|---|---|---|---|
| 1 | A—C(O)Cl | BrMg—Y | A—C(O)—Y |
| 2 | A—CR$^2$R$^{2a}$C(O)Cl | BrMg—Y | A—CR$^2$R$^{2a}$C(O)—Y |
| 3 | A—C(O)Cl | BrMgCR$^2$R$^{2a}$—Y | A—C(O)CR$^2$R$^{2a}$—Y |
| 4 | A—CR$^2$R$^{2a}$C(O)Cl | BrMgCR$^2$R$^{2a}$—Y | A—CR$^2$R$^{2a}$C(O)CR$^2$R$^{2a}$—Y |

The coupling chemistry of Table B can be (carried out by a variety of methods. The Grignard reagent required for Y is prepared from a halogen analog of Y in dry ether, dimethoxyethane or tetrahydrofuran at 0° C. to the reflux point of the solvent. This Grignard reagent can be reacted directly under very controlled conditions, that is low temeprature (−20° C. or lower) and with a large excess of acid chloride or with catalytic or stoichiometric copper bromide.dimethyl sulfide complex in dimethyl sulfide as a solvent or with a variant thereof. Other methods available include transforming the Grignard reagent to the cadmium reagent and coupling according to the procedure of Carson and Prout (Org. Syn. Col. Vol. 3 (1955) 601) or a coupling mediated by Fe(acac)$_3$ according to Fiandanese et al. (Tetrahedron Lett., (1984) 4805), or a coupling mediated by manganese (II) catalysis (Cahiez and Laboue, Tetrahedron Lett., 33(31), (1992) 4437).

TABLE C

Preparation of ether and thioether linkages between A and B

| Rxn. No. | if A contains: | then the reactive substituent of Y is: | to give the following product A—X—Y: |
|---|---|---|---|
| 1 | A—OH | Br—Y | A—O—Y |
| 2 | A—CR$^2$R$^{2a}$—OH | Br—Y | A—CR$^2$R$^{2a}$—Y |
| 3 | A—OH | Br—CR$^2$R$^{2a}$—Y | A—OCR$^2$R$^{2a}$—Y |
| 4 | A—SH | Br—Y | A—S—Y |
| 5 | A—CR$^2$R$^{2a}$—SH | Br—Y | A—CR$^2$R$^{2a}$S—Y |
| 6 | A—SH | Br—CR$^2$R$^{2a}$—Y | A—SCR$^2$R$^{2a}$—Y |

The ether and thioether linkages of Table C can be prepared by reacting the two components in a polar aprotic solvent such as acetone, dimethylformamide or dimethylsulfoxide in the presence of a base such as potassium carbonate, sodium hydride or potassium t-butoxide at temperature ranging from ambient temperature to the reflux point of the solvent used.

TABLE D

Preparation of —SO— and —SO$_2$— linkages from thioethers of Table 3.

| Rxn. No. | if the starting material is: | and it is oxidized with Alumina (wet)/ Oxone (Greenhalgh, Synlett, (1992) 235) the product is: | and it is oxidized with m-chloroperbenzoic acid (Satoh et al., Chem. Lett. (1992) 381), the product is: |
|---|---|---|---|
| 1 | A—S—Y | A—S(O)—Y | A—SO$_2$—Y |
| 2 | A—CR$^2$R$^{2a}$S—Y | A—CR$^2$R$^{2a}$S(O)—Y | A—CR$^2$R$^{2a}$SO$_2$—Y |
| 3 | A—SCR$^2$R$^{2a}$—Y | A—S(O)CR$^2$R$^{2a}$—Y | A—SO$_2$CR$^2$R$^{2a}$—Y |

The thioethers of Table C serve as a convenient starting material for the preparation of the sulfoxide and sulfone analogs of Table D. A combination of wet alumina and oxone can provide a reliable reagent for the oxidation of the thioether to the sulfoxide while m-chloroperbenzoic acid oxidation will give the sulfone.

TABLE E

Methods of Preparing Group E

| Rxn | Q | D is to be | then a transformation that may be used is: |
|---|---|---|---|
| 1 | —CN | —C(=NH)NH2 | E—C≡N i) HCl MeOH ii) NH$_3$OAc, MeOH → E—C(NH$_2$)=NH |
| 2 | —CN | —CH2NH2 | E—C≡N LiAlH$_4$/Et$_2$O → E—CH$_2$NH$_2$ |
| 3 | —CO2H | —CH2NH2 | E—C(=O)OH i) iBuOC(O)Cl NMM, THF then NaBH$_4$, H$_2$O/THF ii) MsCl, Et$_3$N, CH$_2$Cl$_2$ iii) NaN$_3$, DMF iv) SnCl$_2$, MeOH → E—CH$_2$NH$_2$ |
| 4 | —CO2H | —NH2 | E—C(=O)OH i) iBuOC(O)Cl NMM, THF then NaN$_3$ and heat ii) tBuOH, reflux iii) HCl, Et$_2$O → E—NH$_2$ |

In Table E several methods of transforming a functional group Q into group D of Formula 1 are shown. While not all possible functional groups for Q and D are listed and the synthetic methods suggested are not comprehensive, Table E is meant to illustrate strategies and transformations available to a practitioner skilled in the art of organic synthesis for preparing compounds of Formula 1. In reaction 1 of Table E the transformation of a nitrile into an amidine by the Pinner methodology is shown; in reaction 2 the direct reduction of a nitrile by a hydride reducing agent to a methylene amine is illustrated. In reaction 3, the utility of a carboxylic acid, which may be readily derived from its ester or a nitrile if necessary, in the preparation of a methylene amine is shown. This synthetic route is exceptionally flexible because of the several stable intermediates prepared en route to the final product. As outlined, formation of an activated analog, such as the mixed anhydride, allows for the mild reduction of the acid to the methylene alcohol, this may in turn be transformed into a leaving group by sulfonylation or halogenation or protected with a suitable protecting group to be transformed later in the synthesis as the chemistry demands. Once the methylene alcohol is so activated, displacement by an efficient nitrogen nucleophile, such as azide anion, can again provide another suitably stable analog,—the methylene azide—which may be used as a protected form of the methylene amine or transformed directly into the methylene amine group by reduction. Reaction 4 addresses the problem of appending the amine functionality directly through a bond to group E of Formula 1. Once again, the carboxylic acid provides a convenient entre into this selection for group D. The well-know Curtius rearrangement is illustrated here; an activated acid analog can be used to form an acyl azide which upon thermal decomposition is rearranged to the corresponding isocyanate. The isocyanate intermediate may then be captured as a stable carbamate by the addition of a suitable alcohol and further heating. This carbamate can be used as a stable protecting group for the amine or cleaved directly to the desired D. Alternatively, it may be convenient to quench the isocyanate intermediate with water to give the amine directly.

One diastereomer of a compound of Formula I may display superior activity compared with the others. Thus, the following stereochemistries are considered to be a part of the present invention.

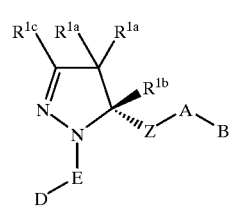

Ia$_1$

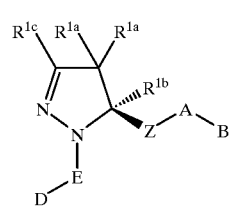

Ia$_2$

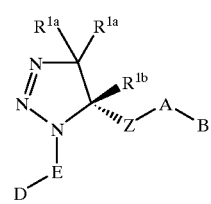

Ib$_1$

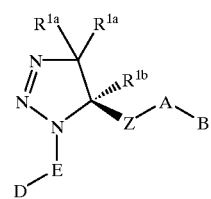

Ib$_2$

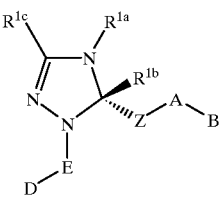

Ic$_1$

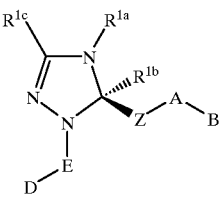

Ic$_2$

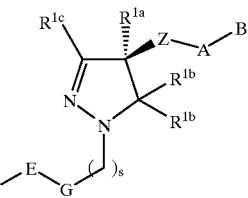

IIa$_1$

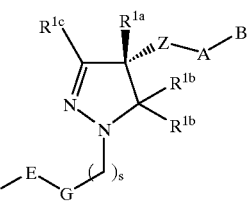

IIa$_2$

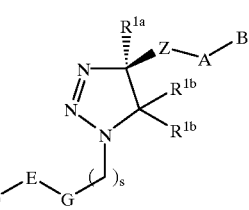

IIb$_1$

-continued

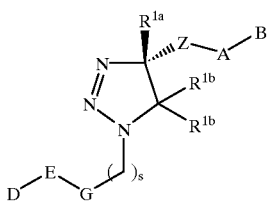

IIb₂

When required, separation of the racemic material can be achieved by HPLC using a chiral column or by a resolution using a resolving agent such as camphonic chloride as in Steven D. Young, et al, *Antimicrobial Agents and Chemotheraphy*, 1995, 2602–2605. A chiral compound of Formula I may also be directly synthesized using a chiral catalyst or a chiral ligand, e.g., Andrew S. Thompson, et al, *Tet. lett.* 1995, 36, 8937–8940).

Other features of the invention will become apparent in the course of the following descriptions of exemplary embodiments which are given for illustration of the invention and are not intended to be limiting thereof.

EXAMPLES

Examples 1 and 2

1-(3-Amidinophenyl)-5-[[(2'-methylsulfonyl-[1,1']-biphen-4-yl)-aminocarbonyl]-3-trifluoromethyl-pyrazoline and 1-(3-aminomethylphenyl)-5-[[(2'-methylsulfonyl-[1,1']-biphen-4-yl)-aminocarbonyl]-3-trifluoromethyl-pyrazoline Part A: To a methanolic solution containing meta-cyanophenyl-hydrazine (2 g, 15.03 mmol) was added trifluoromethylacetaldehyde hydrate (1.74 g, 15.03 mmol). The reaction mixture was heated to gentle reflux overnight. Methanol was stripped off to afford yellow crystals of pure hydrazone (2.99 g, 93%). ¹HNMR (CDCl₃) δ: 10.10 (bs, 1H), 7.33 (m, 2H), 7.10 (m, 2H) ppm; ESI (−ve) mass spectrum analysis m/z (relative intensity) 212 (M−H, 100).

Part B: NCS (1.02 g, 7.69 mmol) was added to a DMF (25 mL) solution of the compound prepared in part A (1.64 g, 7.69 mmol). The reaction mixture was stirred at room temperature over night, quenched with water (500 mL) and organics extracted with ethyl acetate (2×100 mL) dried (MgSO₄) and evaporated to a reddish brown oil. The oil was redissolved in chloroform (25 mL) and to this solution was addled ethyl acrylate (10 mL) followed by slow addition of triethylamine (0.81 mL, 5.75 mmoL). The reaction mixture was refluxed for 18 h cooled and quenched with dil. hydrochloric acid (1N, 20 mL). The organic layer was separated and evaporated to an oil. Chromatography on silica gel (7:3, Hexane:ethylacetate) afforded a colorless oil which solidified on standing (1.5 g, 62%). ¹HNMR(CDCl₃) δ: 7.40–7.22 (m, 4H), 4.89 (dd, J=6.2 and 13.4 Hz, 1H), 4.24 (q, 2H), 3.63–3.50 (dd, J=1.9 and 13.2 Hz, 1H), 3.38 (dd, J=1.9 and 14 Hz, 1H), 1.23 (t, 3H) ppm; ESI mass spectrum analysis m/z (relative intensity) 312 (M+H, 100).

Part C: The product from part B was treated with 2'-methylsulfonyl-4-amino-[1,1']biphenyl under Weinreb conditions (trimethylaluminum in dichloromethane) to afford pure coupled product (oil) after silica gel column chromatography (hexane:ethyl acetate 7:3). ¹HNMR (CDCl₃) δ: 8.40 (bs, 1H), 8.17 (dd, J=1.1 and 7.8 Hz, 1H), 7.65–7.25 (m, 1H), 4.90 (m, 1H), 3.78 (m, 1H), 3.38 (dd, J=1.5 and 8.1 Hz, 1H), 2.69 s, 3H); ESI (−ve) mass spectrum analysis m/z (rel. intensity) 511 (M−H, 100).

Part D: The product from part C was subjected to the Pinner amidine reaction sequence (HCl/MeOH followed by ammonium carbonate in methanol), purified via standard HPLC purification, lyophilization to afford (40% yield) of Example 1 as colorless crystals. ¹HNMR(DMSO₆) δ: 9.36 (bs, 1.5H), 9.00 (bs, 1.5 Hz), 8.06 (d, J=7.7 Hz, 1H), 7.53–7.78 (m, 6H), 7.35 (d, J=8.1 Hz, 3H), 7.27 (d, J=8.0 Hz, 1H), 7.17 (d, J=8.5 Hz, 1H), 5.33 (dd, J=6.2 and 13.2 Hz, 1H), 3.76 (t, 1H), 3.40 (d, J=3.1 Hz, 1H), 2.84(s, 3H) ppm; ESI (+ve) mass spectum analysis m/z (relative intensity) 530 (M+H, 100).

Additionally, the compound form Part C was subjected to reduction using 10% Pd/C in an acidic medium (methanol/acetic acid). Purification via standard HPLC techniques and lyophilization afforded the benzylamine (10% yield). ¹HNMR(DMSO₆) δ: 8.07 (bs, 2H), 8.01 (d, J=8 Hz, 1H), 7.70 (m, 1H), 7.59 (m, 3H), 7.28 (m, 4H), 6.95 (d, J=8 Hz, 1H), 6.83 (dd, J=1/5 and 8 Hz, 1H), 6.40 (bs, 2H), 5.22 (dd, J=6.5 and 13 Hz, 1H), 4.00 (m, 1H), 3.71 (m, 1H), 3.34 (dd, J=1.5 and 8 Hz, 1H), 2.84 (s, 3H) ppm; ESI mass spectrum analysis m/z (relative intensity) 517 (M+H, 100).

The following tables contain representative examples of the present invention. Each entry in each table is intended to be paired with each formulae at the start of the table. For example, in Table 1, example 1 is intended to be paired with each of formulae a–ttt and in Table 2, example 1 is intended to be paired with each of formulae a–ss.

The following groups are intended for group A in the following tables.

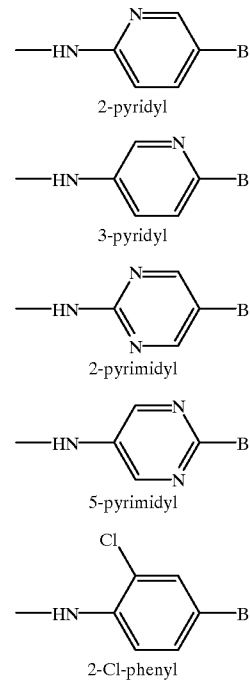

-continued
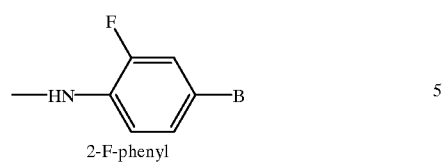
2-F-phenyl    5
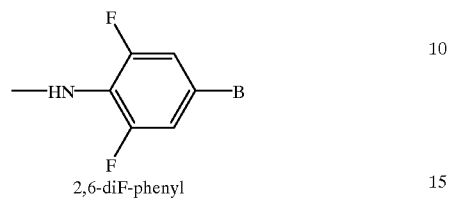
2,6-diF-phenyl    10
TABLE 1
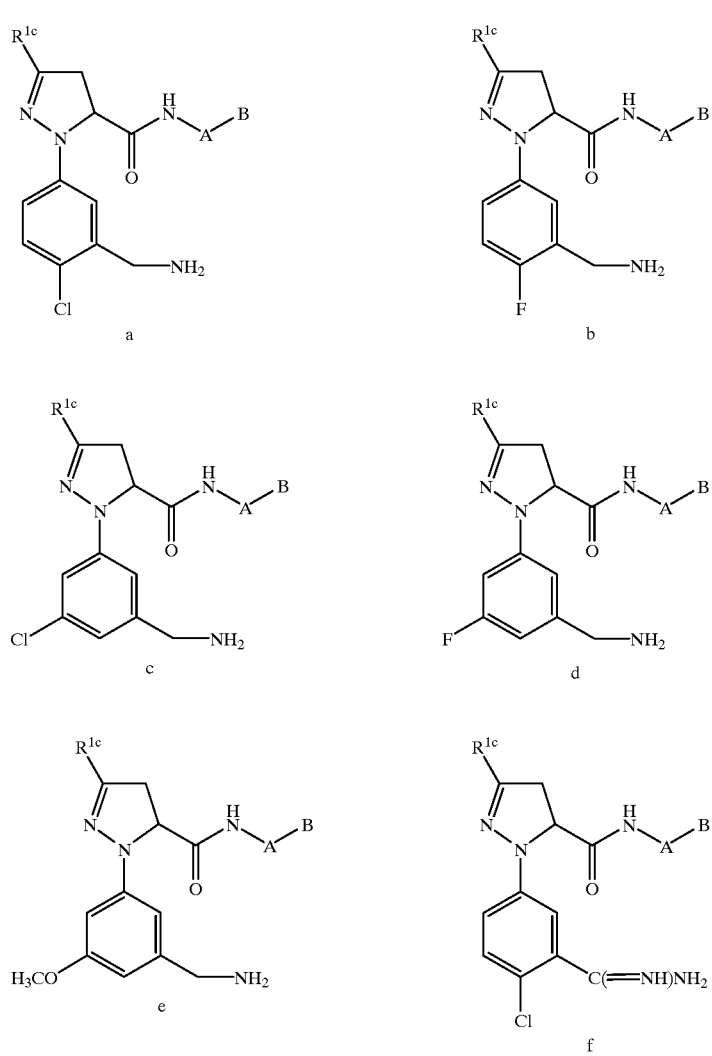

TABLE 1-continued
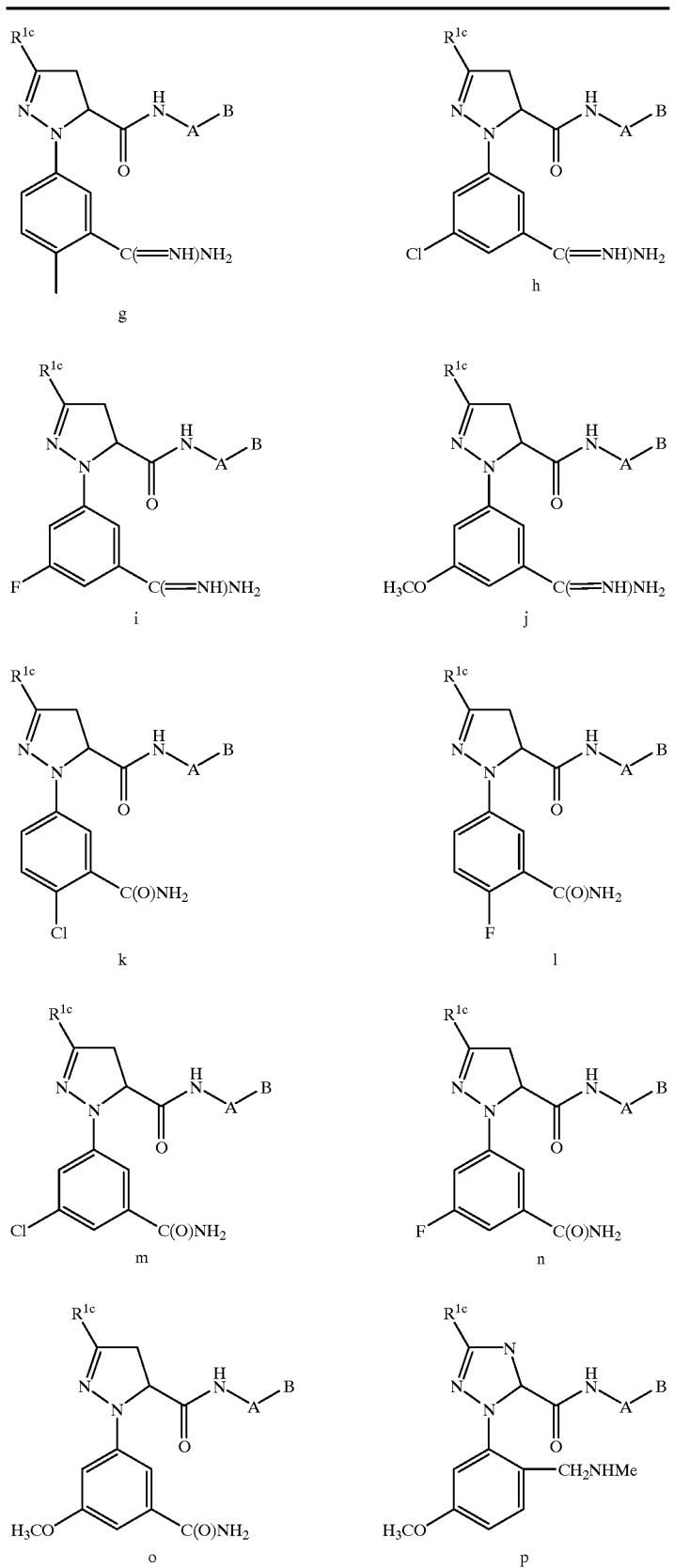

TABLE 1-continued
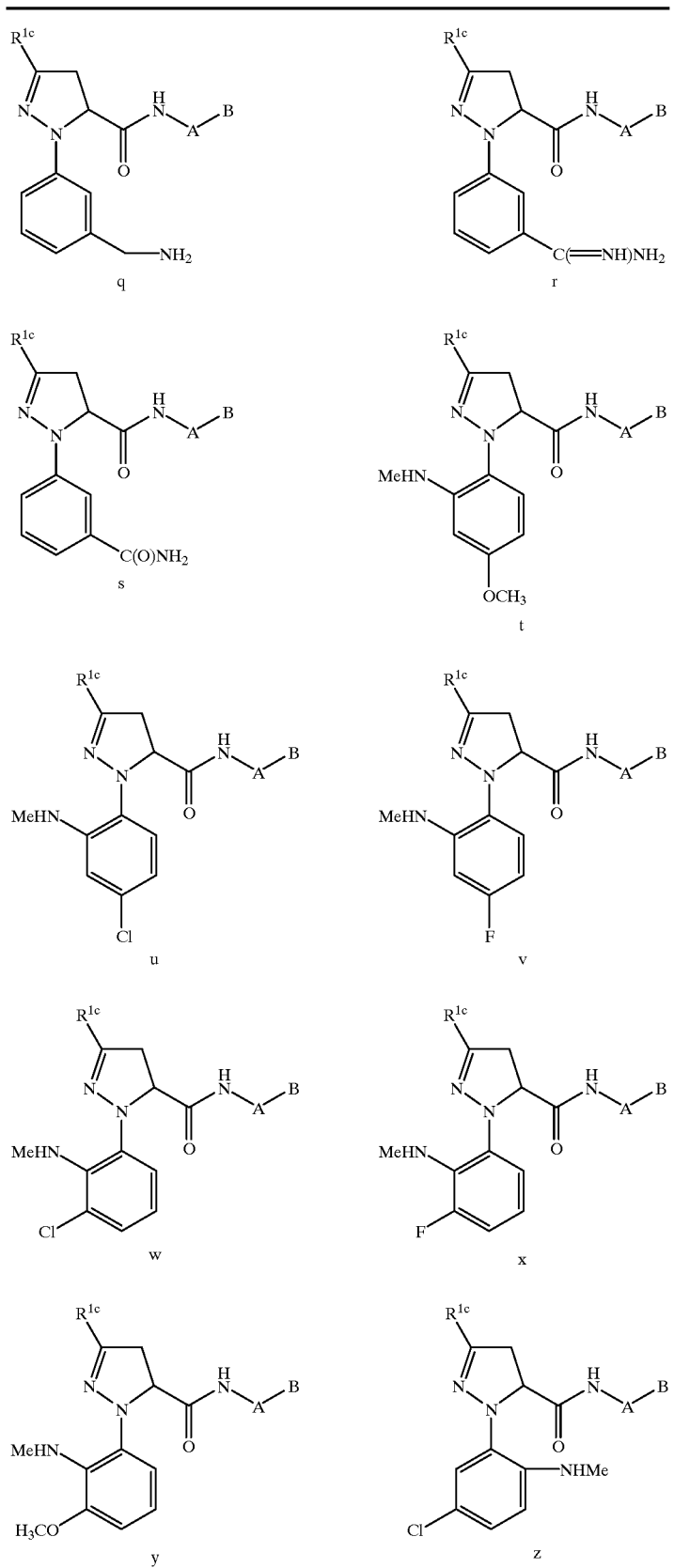

TABLE 1-continued
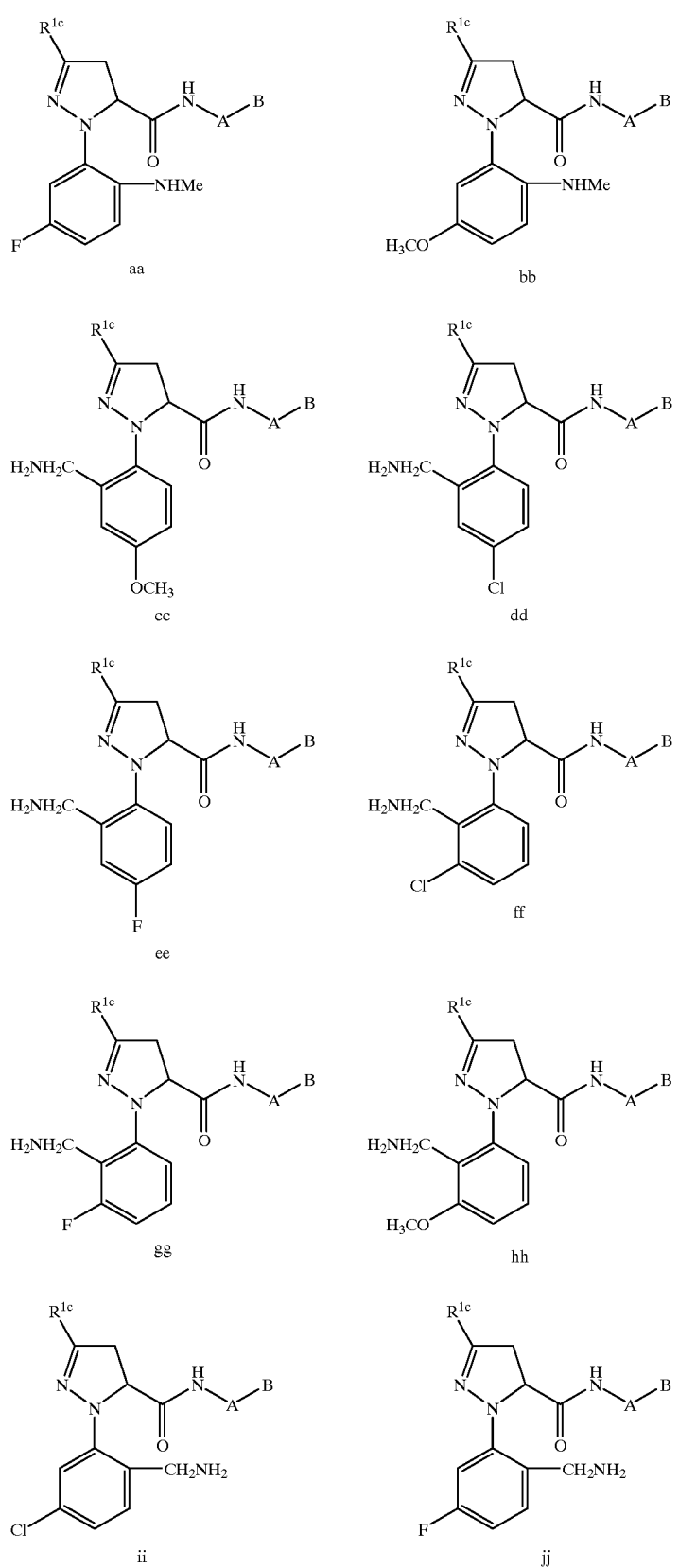

TABLE 1-continued
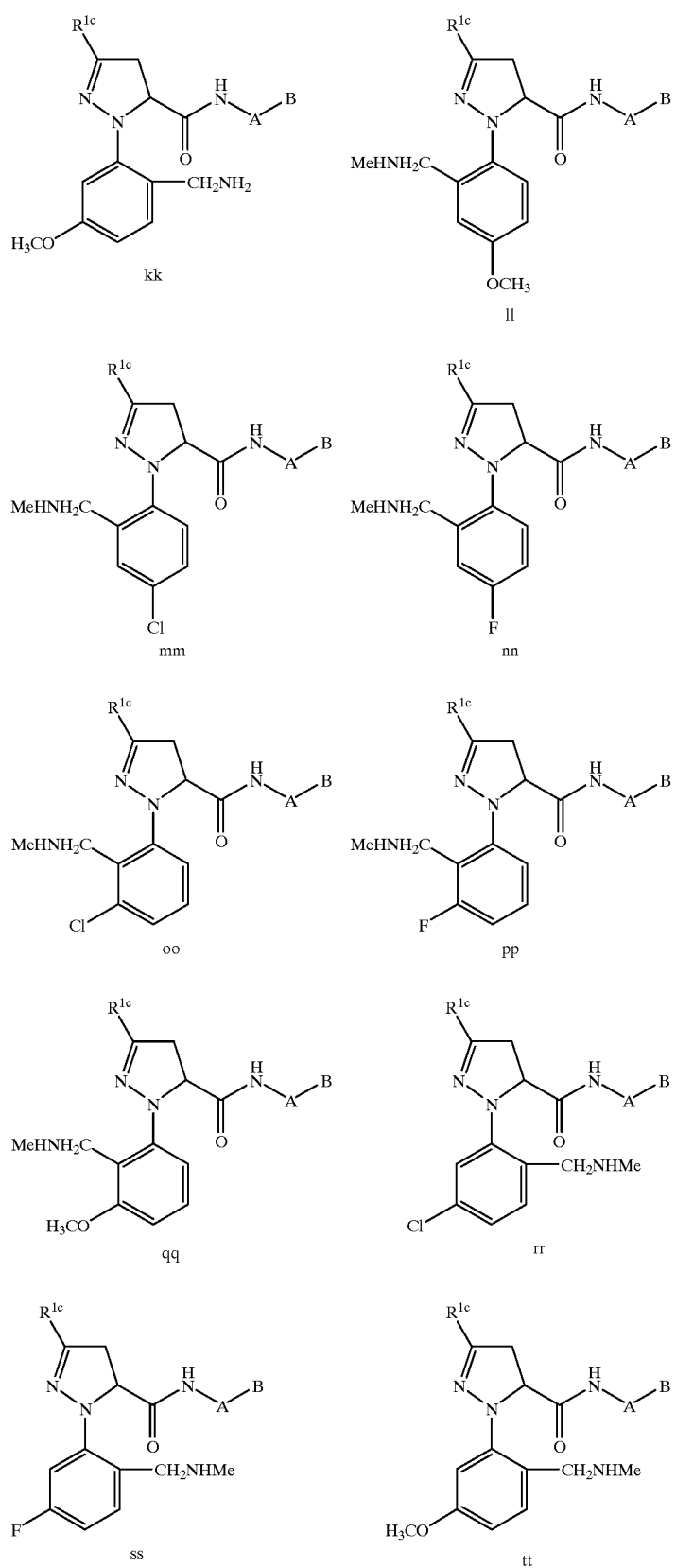

TABLE 1-continued
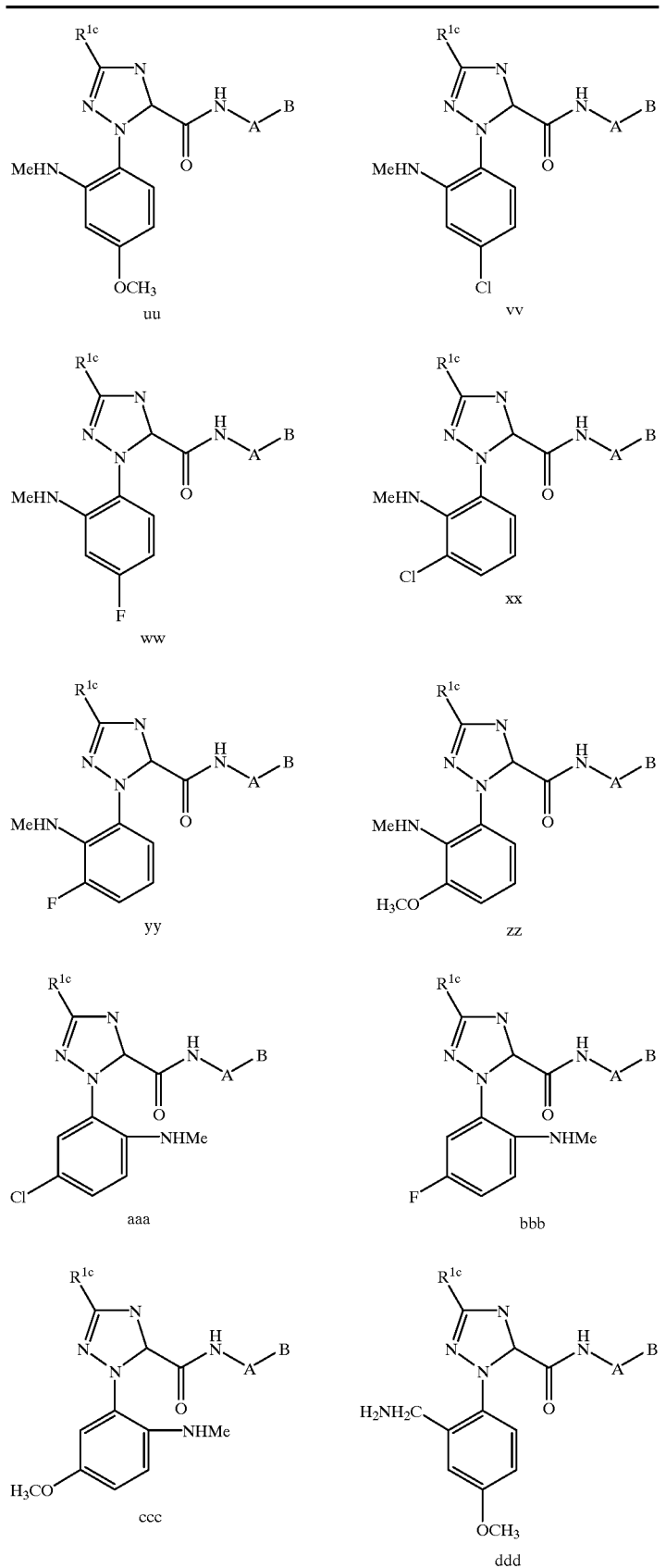

TABLE 1-continued
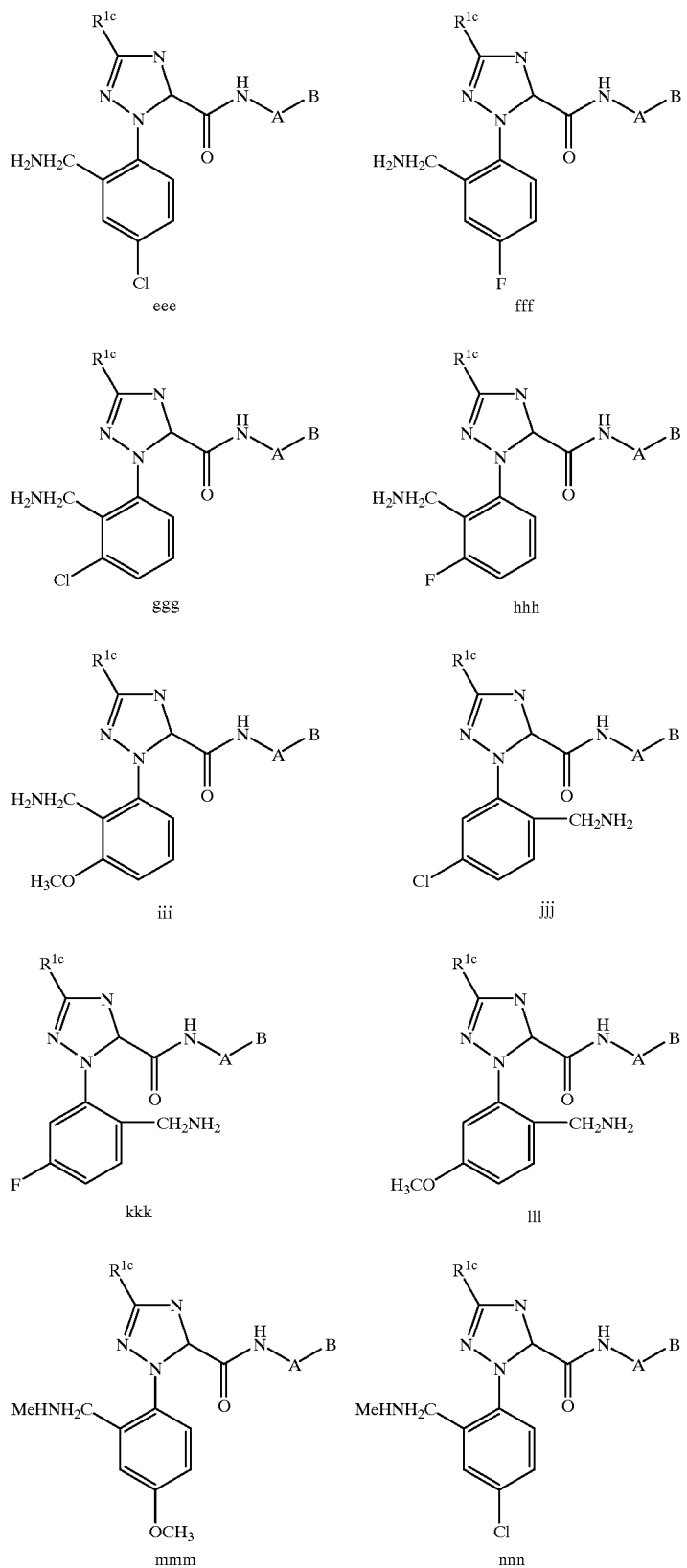

TABLE 1-continued ooo, ppp, qqq, rrr, sss, ttt (structures)

| Ex # | R$^{1c}$ | A | B |
|---|---|---|---|
| 1 | CH$_3$ | phenyl | 2-(aminosulfonyl)phenyl |
| 2 | CH$_3$ | phenyl | 2-(methylaminosulfonyl)phenyl |
| 3 | CH$_3$ | phenyl | 1-pyrrolidinocarbonyl |
| 4 | CH$_3$ | phenyl | 2-(methylsulfonyl)phenyl |
| 5 | CH$_3$ | phenyl | 4-morpholino |
| 6 | CH$_3$ | phenyl | 2-(1'-CF$_3$-tetrazol-2-yl)phenyl |
| 7 | CH$_3$ | phenyl | 4-morpholinocarbonyl |
| 8 | CH$_3$ | phenyl | 2-methyl-1-imidazolyl |
| 9 | CH$_3$ | phenyl | 5-methyl-1-imidazolyl |
| 10 | CH$_3$ | phenyl | 2-methylsulfonyl-1-imidazolyl |
| 11 | CH$_3$ | 2-pyridyl | 2-(aminosulfonyl)phenyl |
| 12 | CH$_3$ | 2-pyridyl | 2-(methylaminosulfonyl)phenyl |
| 13 | CH$_3$ | 2-pyridyl | 1-pyrrolidinocarbonyl |
| 14 | CH$_3$ | 2-pyridyl | 2-(methylsulfonyl)phenyl |
| 15 | CH$_3$ | 2-pyridyl | 4-morpholino |
| 16 | CH$_3$ | 2-pyridyl | 2-(1'-CF$_3$-tetrazol-2-yl)phenyl |
| 17 | CH$_3$ | 2-pyridyl | 4-morpholinocarbonyl |
| 18 | CH$_3$ | 2-pyridyl | 2-methyl-1-imidazolyl |
| 19 | CH$_3$ | 2-pyridyl | 5-methyl-1-imidazolyl |
| 20 | CH$_3$ | 2-pyridyl | 2-methylsulfonyl-1-imidazolyl |
| 21 | CH$_3$ | 3-pyridyl | 2-(aminosulfonyl)phenyl |
| 22 | CH$_3$ | 3-pyridyl | 2-(methylaminosulfonyl)phenyl |
| 23 | CH$_3$ | 3-pyridyl | 1-pyrrolidinocarbonyl |
| 24 | CH$_3$ | 3-pyridyl | 2-(methylsulfonyl)phenyl |
| 25 | CH$_3$ | 3-pyridyl | 4-morpholino |
| 26 | CH$_3$ | 3-pyridyl | 2-(1'-CF$_3$-tetrazol-2-yl)phenyl |
| 27 | CH$_3$ | 3-pyridyl | 4-morpholinocarbonyl |
| 28 | CH$_3$ | 3-pyridyl | 2-methyl-1-imidazolyl |
| 29 | CH$_3$ | 3-pyridyl | 5-methyl-1-imidazolyl |
| 30 | CH$_3$ | 3-pyridyl | 2-methylsulfonyl-1-imidazolyl |
| 31 | CH$_3$ | 2-pyrimidyl | 2-(aminosulfonyl)phenyl |
| 32 | CH$_3$ | 2-pyrimidyl | 2-(methylaminosulfonyl)phenyl |

TABLE 1-continued

| | | | |
|---|---|---|---|
| 33 | $CH_3$ | 2-pyrimidyl | 1-pyrrolidinocarbonyl |
| 34 | $CH_3$ | 2-pyrimidyl | 2-(methylsulfonyl)phenyl |
| 35 | $CH_3$ | 2-pyrimidyl | 4-morpholino |
| 36 | $CH_3$ | 2-pyrimidyl | 2-(1'-$CF_3$-tetrazol-2-yl)phenyl |
| 37 | $CH_3$ | 2-pyrimidyl | 4-morpholinocarbonyl |
| 38 | $CH_3$ | 2-pyrimidyl | 2-methyl-1-imidazolyl |
| 39 | $CH_3$ | 2-pyrimidyl | 5-methyl-1-imidazolyl |
| 40 | $CH_3$ | 2-pyrimidyl | 2-methylsulfonyl-1-imidazolyl |
| 41 | $CH_3$ | 5-pyrimidyl | 2-(aminosulfonyl)phenyl |
| 42 | $CH_3$ | 5-pyrimidyl | 2-(methylaminosulfonyl)phenyl |
| 43 | $CH_3$ | 5-pyrimidyl | 1-pyrrolidinocarbonyl |
| 44 | $CH_3$ | 5-pyrimidyl | 2-(methylsulfonyl)phenyl |
| 45 | $CH_3$ | 5-pyrimidyl | 4-morpholino |
| 46 | $CH_3$ | 5-pyrimidyl | 2-(1'-$CF_3$-tetrazol-2-yl)phenyl |
| 47 | $CH_3$ | 5-pyrimidyl | 4-morpholinocarbonyl |
| 48 | $CH_3$ | 5-pyrimidyl | 2-methyl-1-imidazolyl |
| 49 | $CH_3$ | 5-pyrimidyl | 5-methyl-1-imidazolyl |
| 50 | $CH_3$ | 5-pyrimidyl | 2-methylsulfonyl-1-imidazolyl |
| 51 | $CH_3$ | 2-Cl-phenyl | 2-(aminosulfonyl)phenyl |
| 52 | $CH_3$ | 2-Cl-phenyl | 2-(methylaminosulfonyl)phenyl |
| 53 | $CH_3$ | 2-Cl-phenyl | 1-pyrrolidinocarbonyl |
| 54 | $CH_3$ | 2-Cl-phenyl | 2-(methylsulfonyl)phenyl |
| 55 | $CH_3$ | 2-Cl-phenyl | 4-morpholino |
| 56 | $CH_3$ | 2-Cl-phenyl | 2-(1'-$CF_3$-tetrazol-2-yl)phenyl |
| 57 | $CH_3$ | 2-Cl-phenyl | 4-morpholinocarbonyl |
| 58 | $CH_3$ | 2-Cl-phenyl | 2-methyl-1-imidazolyl |
| 59 | $CH_3$ | 2-Cl-phenyl | 5-methyl-1-imidazolyl |
| 60 | $CH_3$ | 2-Cl-phenyl | 2-methylsulfonyl-1-imidazolyl |
| 61 | $CH_3$ | 2-F-phenyl | 2-(aminosulfonyl)phenyl |
| 62 | $CH_3$ | 2-F-phenyl | 2-(methylaminosulfonyl)phenyl |
| 63 | $CH_3$ | 2-F-phenyl | 1-pyrrolidinocarbonyl |
| 64 | $CH_3$ | 2-F-phenyl | 2-(methylsulfonyl)phenyl |
| 65 | $CH_3$ | 2-F-phenyl | 4-morpholino |
| 66 | $CH_3$ | 2-F-phenyl | 2-(1'-$CF_3$-tetrazol-2-yl)phenyl |
| 67 | $CH_3$ | 2-F-phenyl | 4-morpholinocarbonyl |
| 68 | $CH_3$ | 2-F-phenyl | 2-methyl-1-imidazolyl |
| 69 | $CH_3$ | 2-F-phenyl | 5-methyl-1-imidazolyl |
| 70 | $CH_3$ | 2-F-phenyl | 2-methylsulfonyl-1-imidazolyl |
| 71 | $CH_3$ | 2,6-diF-phenyl | 2-(aminosulfonyl)phenyl |
| 72 | $CH_3$ | 2,6-diF-phenyl | 2-(methylaminosulfonyl)phenyl |
| 73 | $CH_3$ | 2,6-diF-phenyl | 1-pyrrolidinocarbonyl |
| 74 | $CH_3$ | 2,6-diF-phenyl | 2-(methylsulfonyl)phenyl |
| 75 | $CH_3$ | 2,6-diF-phenyl | 4-morpholino |
| 76 | $CH_3$ | 2,6-diF-phenyl | 2-(1'-$CF_3$-tetrazol-2-yl)phenyl |
| 77 | $CH_3$ | 2,6-diF-phenyl | 4-morpholinocarbonyl |
| 78 | $CH_3$ | 2,6-diF-phenyl | 2-methyl-1-imidazolyl |
| 79 | $CH_3$ | 2,6-diF-phenyl | 5-methyl-1-imidazolyl |
| 80 | $CH_3$ | 2,6-diF-phenyl | 2-methylsulfonyl-1-imidazolyl |
| 81 | $CH_2CH_3$ | phenyl | 2-(aminosulfonyl)phenyl |
| 82 | $CH_2CH_3$ | phenyl | 2-(methylaminosulfonyl)phenyl |
| 83 | $CH_2CH_3$ | phenyl | 1-pyrrolidinocarbonyl |
| 84 | $CH_2CH_3$ | phenyl | 2-(methylsulfonyl)phenyl |
| 85 | $CH_2CH_3$ | phenyl | 4-morpholino |
| 86 | $CH_2CH_3$ | phenyl | 2-(1'-$CF_3$-tetrazol-2-yl)phenyl |
| 87 | $CH_2CH_3$ | phenyl | 4-morpholinocarbonyl |
| 88 | $CH_2CH_3$ | phenyl | 2-methyl-1-imidazolyl |
| 89 | $CH_2CH_3$ | phenyl | 5-methyl-1-imidazolyl |
| 90 | $CH_2CH_3$ | phenyl | 2-methylsulfonyl-1-imidazolyl |
| 91 | $CH_2CH_3$ | 2-pyridyl | 2-(aminosulfonyl)phenyl |
| 92 | $CH_2CH_3$ | 2-pyridyl | 2-(methylaminosulfonyl)phenyl |
| 93 | $CH_2CH_3$ | 2-pyridyl | 1-pyrrolidinocarbonyl |
| 94 | $CH_2CH_3$ | 2-pyridyl | 2-(methylsulfonyl)phenyl |
| 95 | $CH_2CH_3$ | 2-pyridyl | 4-morpholino |
| 96 | $CH_2CH_3$ | 2-pyridyl | 2-(1'-$CF_3$-tetrazol-2-yl)phenyl |
| 97 | $CH_2CH_3$ | 2-pyridyl | 4-morpholinocarbonyl |
| 98 | $CH_2CH_3$ | 2-pyridyl | 2-methyl-1-imidazolyl |
| 99 | $CH_2CH_3$ | 2-pyridyl | 5-methyl-1-imidazolyl |
| 100 | $CH_2CH_3$ | 2-pyridyl | 2-methylsulfonyl-1-imidazolyl |
| 101 | $CH_2CH_3$ | 3-pyridyl | 2-(aminosulfonyl)phenyl |
| 102 | $CH_2CH_3$ | 3-pyridyl | 2-(methylaminosulfonyl)phenyl |
| 103 | $CH_2CH_3$ | 3-pyridyl | 1-pyrrolidinocarbonyl |
| 104 | $CH_2CH_3$ | 3-pyridyl | 2-(methylsulfonyl)phenyl |
| 105 | $CH_2CH_3$ | 3-pyridyl | 4-morpholino |
| 106 | $CH_2CH_3$ | 3-pyridyl | 2-(1'-$CF_3$-tetrazol-2-yl)phenyl |
| 107 | $CH_2CH_3$ | 3-pyridyl | 4-morpholinocarbonyl |
| 108 | $CH_2CH_3$ | 3-pyridyl | 2-methyl-1-imidazolyl |
| 109 | $CH_2CH_3$ | 3-pyridyl | 5-methyl-1-imidazolyl |
| 110 | $CH_2CH_3$ | 3-pyridyl | 2-methylsulfonyl-1-imidazolyl |
| 111 | $CH_2CH_3$ | 2-pyrimidyl | 2-(aminosulfonyl)phenyl |

TABLE 1-continued

| | | | |
|---|---|---|---|
| 112 | $CH_2CH_3$ | 2-pyrimidyl | 2-(methylaminosulfonyl)phenyl |
| 113 | $CH_2CH_3$ | 2-pyrimidyl | 1-pyrrolidinocarbonyl |
| 114 | $CH_2CH_3$ | 2-pyrimidyl | 2-(methylsulfonyl)phenyl |
| 115 | $CH_2CH_3$ | 2-pyrimidyl | 4-morpholino |
| 116 | $CH_2CH_3$ | 2-pyrimidyl | 2-(1'-$CF_3$-tetrazol-2-yl)phenyl |
| 117 | $CH_2CH_3$ | 2-pyrimidyl | 4-morpholinocarbonyl |
| 118 | $CH_2CH_3$ | 2-pyrimidyl | 2-methyl-1-imidazolyl |
| 119 | $CH_2CH_3$ | 2-pyrimidyl | 5-methyl-1-imidazolyl |
| 120 | $CH_2CH_3$ | 2-pyrimidyl | 2-methylsulfonyl-1-imidazolyl |
| 121 | $CH_2CH_3$ | 5-pyrimidyl | 2-(aminosulfonyl)phenyl |
| 122 | $CH_2CH_3$ | 5-pyrimidyl | 2-(methylaminosulfonyl)phenyl |
| 123 | $CH_2CH_3$ | 5-pyrimidyl | 1-pyrrolidinocarbonyl |
| 124 | $CH_2CH_3$ | 5-pyrimidyl | 2-(methylsulfonyl)phenyl |
| 125 | $CH_2CH_3$ | 5-pyrimidyl | 4-morpholino |
| 126 | $CH_2CH_3$ | 5-pyrimidyl | 2-(1'-$CF_3$-tetrazol-2-yl)phenyl |
| 127 | $CH_2CH_3$ | 5-pyrimidyl | 4-morpholinocarbonyl |
| 128 | $CH_2CH_3$ | 5-pyrimidyl | 2-methyl-1-imidazolyl |
| 129 | $CH_2CH_3$ | 5-pyrimidyl | 5-methyl-1-imidazolyl |
| 130 | $CH_2CH_3$ | 5-pyrimidyl | 2-methylsulfonyl-1-imidazolyl |
| 131 | $CH_2CH_3$ | 2-Cl-phenyl | 2-(aminosulfonyl)phenyl |
| 132 | $CH_2CH_3$ | 2-Cl-phenyl | 2-(methylaminosulfonyl)phenyl |
| 133 | $CH_2CH_3$ | 2-Cl-phenyl | 1-pyrrolidinocarbonyl |
| 134 | $CH_2CH_3$ | 2-Cl-phenyl | 2-(methylsulfonyl)phenyl |
| 135 | $CH_2CH_3$ | 2-Cl-phenyl | 4-morpholino |
| 136 | $CH_2CH_3$ | 2-Cl-phenyl | 2-(1'-$CF_3$-tetrazol-2-yl)phenyl |
| 137 | $CH_2CH_3$ | 2-Cl-phenyl | 4-morpholinocarbonyl |
| 138 | $CH_2CH_3$ | 2-Cl-phenyl | 2-methyl-1-imidazolyl |
| 139 | $CH_2CH_3$ | 2-Cl-phenyl | 5-methyl-1-imidazolyl |
| 140 | $CH_2CH_3$ | 2-Cl-phenyl | 2-methylsulfonyl-1-imidazolyl |
| 141 | $CH_2CH_3$ | 2-F-phenyl | 2-(aminosulfonyl)phenyl |
| 142 | $CH_2CH_3$ | 2-F-phenyl | 2-(methylaminosulfonyl)phenyl |
| 143 | $CH_2CH_3$ | 2-F-phenyl | 1-pyrrolidinocarbonyl |
| 144 | $CH_2CH_3$ | 2-F-phenyl | 2-(methylsulfonyl)phenyl |
| 145 | $CH_2CH_3$ | 2-F-phenyl | 4-morpholino |
| 146 | $CH_2CH_3$ | 2-F-phenyl | 2-(1'-$CF_3$-tetrazol-2-yl)phenyl |
| 147 | $CH_2CH_3$ | 2-F-phenyl | 4-morpholinocarbonyl |
| 148 | $CH_2CH_3$ | 2-F-phenyl | 2-methyl-1-imidazolyl |
| 149 | $CH_2CH_3$ | 2-F-phenyl | 5-methyl-1-imidazolyl |
| 150 | $CH_2CH_3$ | 2-F-phenyl | 2-methylsulfonyl-1-imidazolyl |
| 151 | $CH_2CH_3$ | 2,6-diF-phenyl | 2-(aminosulfonyl)phenyl |
| 152 | $CH_2CH_3$ | 2,6-diF-phenyl | 2-(methylaminosulfonyl)phenyl |
| 153 | $CH_2CH_3$ | 2,6-diF-phenyl | 1-pyrrolidinocarbonyl |
| 154 | $CH_2CH_3$ | 2,6-diF-phenyl | 2-(methylsulfonyl)phenyl |
| 155 | $CH_2CH_3$ | 2,6-diF-phenyl | 4-morpholino |
| 156 | $CH_2CH_3$ | 2,6-diF-phenyl | 2-(1'-$CF_3$-tetrazol-2-yl)phenyl |
| 157 | $CH_2CH_3$ | 2,6-diF-phenyl | 4-morpholinocarbonyl |
| 158 | $CH_2CH_3$ | 2,6-diF-phenyl | 2-methyl-1-imidazolyl |
| 159 | $CH_2CH_3$ | 2,6-diF-phenyl | 5-methyl-1-imidazolyl |
| 160 | $CH_2CH_3$ | 2,6-diF-phenyl | 2-methylsulfonyl-1-imidazolyl |
| 161 | $CF_3$ | phenyl | 2-(aminosulfonyl)phenyl |
| 162 | $CF_3$ | phenyl | 2-(methylaminosulfonyl)phenyl |
| 163 | $CF_3$ | phenyl | 1-pyrrolidinocarbonyl |
| 164 | $CF_3$ | phenyl | 2-(methylsulfonyl)phenyl |
| 165 | $CF_3$ | phenyl | 4-morpholino |
| 166 | $CF_3$ | phenyl | 2-(1'-$CF_3$-tetrazol-2-yl)phenyl |
| 167 | $CF_3$ | phenyl | 4-morpholinocarbonyl |
| 168 | $CF_3$ | phenyl | 2-methyl-1-imidazolyl |
| 169 | $CF_3$ | phenyl | 5-methyl-1-imidazolyl |
| 170 | $CF_3$ | phenyl | 2-methylsulfonyl-1-imidazolyl |
| 171 | $CF_3$ | 2-pyridyl | 2-(aminosulfonyl)phenyl |
| 172 | $CF_3$ | 2-pyridyl | 2-(methylaminosulfonyl)phenyl |
| 173 | $CF_3$ | 2-pyridyl | 1-pyrrolidinocarbonyl |
| 174 | $CF_3$ | 2-pyridyl | 2-(methylsulfonyl)phenyl |
| 175 | $CF_3$ | 2-pyridyl | 4-morpholino |
| 176 | $CF_3$ | 2-pyridyl | 2-(1'-$CF_3$-tetrazol-2-yl)phenyl |
| 177 | $CF_3$ | 2-pyridyl | 4-morpholinocarbonyl |
| 178 | $CF_3$ | 2-pyridyl | 2-methyl-1-imidazolyl |
| 179 | $CF_3$ | 2-pyridyl | 5-methyl-1-imidazolyl |
| 180 | $CF_3$ | 2-pyridyl | 2-methylsulfonyl-1-imidazolyl |
| 181 | $CF_3$ | 3-pyridyl | 2-(aminosulfonyl)phenyl |
| 182 | $CF_3$ | 3-pyridyl | 2-(methylaminosulfonyl)phenyl |
| 183 | $CF_3$ | 3-pyridyl | 1-pyrrolidinocarbonyl |
| 184 | $CF_3$ | 3-pyridyl | 2-(methylsulfonyl)phenyl |
| 185 | $CF_3$ | 3-pyridyl | 4-morpholino |
| 186 | $CF_3$ | 3-pyridyl | 2-(1'-$CF_3$-tetrazol-2-yl)phenyl |
| 187 | $CF_3$ | 3-pyridyl | 4-morpholinocarbonyl |
| 188 | $CF_3$ | 3-pyridyl | 2-methyl-1-imidazolyl |
| 189 | $CF_3$ | 3-pyridyl | 5-methyl-1-imidazolyl |
| 190 | $CF_3$ | 3-pyridyl | 2-methylsulfonyl-1-imidazolyl |

TABLE 1-continued

| | | | |
|---|---|---|---|
| 191 | $CF_3$ | 2-pyrimidyl | 2-(aminosulfonyl)phenyl |
| 192 | $CF_3$ | 2-pyrimidyl | 2-(methylaminosulfonyl)phenyl |
| 193 | $CF_3$ | 2-pyrimidyl | 1-pyrrolidinocarbonyl |
| 194 | $CF_3$ | 2-pyrimidyl | 2-(methylsulfonyl)phenyl |
| 195 | $CF_3$ | 2-pyrimidyl | 4-morpholino |
| 196 | $CF_3$ | 2-pyrimidyl | 2-(1'-$CF_3$-tetrazol-2-yl)phenyl |
| 197 | $CF_3$ | 2-pyrimidyl | 4-morpholinocarbonyl |
| 198 | $CF_3$ | 2-pyrimidyl | 2-methyl-1-imidazolyl |
| 199 | $CF_3$ | 2-pyrimidyl | 5-methyl-1-imidazolyl |
| 200 | $CF_3$ | 2-pyrimidyl | 2-methylsulfonyl-1-imidazolyl |
| 201 | $CF_3$ | 5-pyrimidyl | 2-(aminosulfonyl)phenyl |
| 202 | $CF_3$ | 5-pyrimidyl | 2-(methylaminosulfonyl)phenyl |
| 203 | $CF_3$ | 5-pyrimidyl | 1-pyrrolidinocarbonyl |
| 204 | $CF_3$ | 5-pyrimidyl | 2-(methylsulfonyl)phenyl |
| 205 | $CF_3$ | 5-pyrimidyl | 4-morpholino |
| 206 | $CF_3$ | 5-pyrimidyl | 2-(1'-$CF_3$-tetrazol-2-yl)phenyl |
| 207 | $CF_3$ | 5-pyrimidyl | 4-morpholinocarbonyl |
| 208 | $CF_3$ | 5-pyrimidyl | 2-methyl-1-imidazolyl |
| 209 | $CF_3$ | 5-pyrimidyl | 5-methyl-1-imidazolyl |
| 210 | $CF_3$ | 5-pyrimidyl | 2-methylsulfonyl-1-imidazolyl |
| 211 | $CF_3$ | 2-Cl-phenyl | 2-(aminosulfonyl)phenyl |
| 212 | $CF_3$ | 2-Cl-phenyl | 2-(methylaminosulfonyl)phenyl |
| 213 | $CF_3$ | 2-Cl-phenyl | 1-pyrrolidinocarbonyl |
| 214 | $CF_3$ | 2-Cl-phenyl | 2-(methylsulfonyl)phenyl |
| 215 | $CF_3$ | 2-Cl-phenyl | 4-morpholino |
| 216 | $CF_3$ | 2-Cl-phenyl | 2-(1'-$CF_3$-tetrazol-2-yl)phenyl |
| 217 | $CF_3$ | 2-Cl-phenyl | 4-morpholinocarbonyl |
| 218 | $CF_3$ | 2-Cl-phenyl | 2-methyl-1-imidazolyl |
| 219 | $CF_3$ | 2-Cl-phenyl | 5-methyl-1-imidazolyl |
| 220 | $CF_3$ | 2-Cl-phenyl | 2-methylsulfonyl-1-imidazolyl |
| 221 | $CF_3$ | 2-F-phenyl | 2-(aminosulfonyl)phenyl |
| 222 | $CF_3$ | 2-F-phenyl | 2-(methylaminosulfonyl)phenyl |
| 223 | $CF_3$ | 2-F-phenyl | 1-pyrrolidinocarbonyl |
| 224 | $CF_3$ | 2-F-phenyl | 2-(methylsulfonyl)phenyl |
| 225 | $CF_3$ | 2-F-phenyl | 4-morpholino |
| 226 | $CF_3$ | 2-F-phenyl | 2-(1'-$CF_3$-tetrazol-2-yl)phenyl |
| 227 | $CF_3$ | 2-F-phenyl | 4-morpholinocarbonyl |
| 228 | $CF_3$ | 2-F-phenyl | 2-methyl-1-imidazolyl |
| 229 | $CF_3$ | 2-F-phenyl | 5-methyl-1-imidazolyl |
| 230 | $CF_3$ | 2-F-phenyl | 2-methylsulfonyl-1-imidazolyl |
| 231 | $CF_3$ | 2,6-diF-phenyl | 2-(aminosulfonyl)phenyl |
| 232 | $CF_3$ | 2,6-diF-phenyl | 2-(methylaminosulfonyl)phenyl |
| 233 | $CF_3$ | 2,6-diF-phenyl | 1-pyrrolidinocarbonyl |
| 234 | $CF_3$ | 2,6-diF-phenyl | 2-(methylsulfonyl)phenyl |
| 235 | $CF_3$ | 2,6-diF-phenyl | 4-morpholino |
| 236 | $CF_3$ | 2,6-diF-phenyl | 2-(1'-$CF_3$-tetrazol-2-yl)phenyl |
| 237 | $CF_3$ | 2,6-diF-phenyl | 4-morpholinocarbonyl |
| 238 | $CF_3$ | 2,6-diF-phenyl | 2-methyl-1-imidazolyl |
| 239 | $CF_3$ | 2,6-diF-phenyl | 5-methyl-1-imidazolyl |
| 240 | $CF_3$ | 2,6-diF-phenyl | 2-methylsulfonyl-1-imidazolyl |
| 241 | $SCH_3$ | phenyl | 2-(aminosulfonyl)phenyl |
| 242 | $SCH_3$ | phenyl | 2-(methylaminosulfonyl)phenyl |
| 243 | $SCH_3$ | phenyl | 1-pyrrolidinocarbonyl |
| 244 | $SCH_3$ | phenyl | 2-(methylsulfonyl)phenyl |
| 245 | $SCH_3$ | phenyl | 4-morpholino |
| 246 | $SCH_3$ | phenyl | 2-(1'-$CF_3$-tetrazol-2-yl)phenyl |
| 247 | $SCH_3$ | phenyl | 4-morpholinocarbonyl |
| 248 | $SCH_3$ | phenyl | 2-methyl-1-imidazolyl |
| 249 | $SCH_3$ | phenyl | 5-methyl-1-imidazolyl |
| 250 | $SCH_3$ | phenyl | 2-methylsulfonyl-1-imidazolyl |
| 251 | $SCH_3$ | 2-pyridyl | 2-(aminosulfonyl)phenyl |
| 252 | $SCH_3$ | 2-pyridyl | 2-(methylaminosulfonyl)phenyl |
| 253 | $SCH_3$ | 2-pyridyl | 1-pyrrolidinocarbonyl |
| 254 | $SCH_3$ | 2-pyridyl | 2-(methylsulfonyl)phenyl |
| 255 | $SCH_3$ | 2-pyridyl | 4-morpholino |
| 256 | $SCH_3$ | 2-pyridyl | 2-(1'-$CF_3$-tetrazol-2-yl)phenyl |
| 257 | $SCH_3$ | 2-pyridyl | 4-morpholinocarbonyl |
| 258 | $SCH_3$ | 2-pyridyl | 2-methyl-1-imidazolyl |
| 259 | $SCH_3$ | 2-pyridyl | 5-methyl-1-imidazolyl |
| 260 | $SCH_3$ | 2-pyridyl | 2-methylsulfonyl-1-imidazolyl |
| 261 | $SCH_3$ | 3-pyridyl | 2-(aminosulfonyl)phenyl |
| 262 | $SCH_3$ | 3-pyridyl | 2-(methylaminosulfonyl)phenyl |
| 263 | $SCH_3$ | 3-pyridyl | 1-pyrrolidinocarbonyl |
| 264 | $SCH_3$ | 3-pyridyl | 2-(methylsulfonyl)phenyl |
| 265 | $SCH_3$ | 3-pyridyl | 4-morpholino |
| 266 | $SCH_3$ | 3-pyridyl | 2-(1'-$CF_3$-tetrazol-2-yl)phenyl |
| 267 | $SCH_3$ | 3-pyridyl | 4-morpholinocarbonyl |
| 268 | $SCH_3$ | 3-pyridyl | 2-methyl-1-imidazolyl |
| 269 | $SCH_3$ | 3-pyridyl | 5-methyl-1-imidazolyl |

TABLE 1-continued

| | | | |
|---|---|---|---|
| 270 | $SCH_3$ | 3-pyridyl | 2-methylsulfonyl-1-imidazolyl |
| 271 | $SCH_3$ | 2-pyrimidyl | 2-(aminosulfonyl)phenyl |
| 272 | $SCH_3$ | 2-pyrimidyl | 2-(methylaminosulfonyl)phenyl |
| 273 | $SCH_3$ | 2-pyrimidyl | 1-pyrrolidinocarbonyl |
| 274 | $SCH_3$ | 2-pyrimidyl | 2-(methylsulfonyl)phenyl |
| 275 | $SCH_3$ | 2-pyrimidyl | 4-morpholino |
| 276 | $SCH_3$ | 2-pyrimidyl | 2-(1'-$CF_3$-tetrazol-2-yl)phenyl |
| 277 | $SCH_3$ | 2-pyrimidyl | 4-morpholinocarbonyl |
| 278 | $SCH_3$ | 2-pyrimidyl | 2-methyl-1-imidazolyl |
| 279 | $SCH_3$ | 2-pyrimidyl | 5-methyl-1-imidazolyl |
| 280 | $SCH_3$ | 2-pyrimidyl | 2-methylsulfonyl-1-imidazolyl |
| 281 | $SCH_3$ | 5-pyrimidyl | 2-(aminosulfonyl)phenyl |
| 282 | $SCH_3$ | 5-pyrimidyl | 2-(methylaminosulfonyl)phenyl |
| 283 | $SCH_3$ | 5-pyrimidyl | 1-pyrrolidinocarbonyl |
| 284 | $SCH_3$ | 5-pyrimidyl | 2-(methylsulfonyl)phenyl |
| 285 | $SCH_3$ | 5-pyrimidyl | 4-morpholino |
| 286 | $SCH_3$ | 5-pyrimidyl | 2-(1'-$CF_3$-tetrazol-2-yl)phenyl |
| 287 | $SCH_3$ | 5-pyrimidyl | 4-morpholinocarbonyl |
| 288 | $SCH_3$ | 5-pyrimidyl | 2-methyl-1-imidazolyl |
| 289 | $SCH_3$ | 5-pyrimidyl | 5-methyl-1-imidazolyl |
| 290 | $SCH_3$ | 5-pyrimidyl | 2-methylsulfonyl-1-imidazolyl |
| 291 | $SCH_3$ | 2-Cl-phenyl | 2-(aminosulfonyl)phenyl |
| 292 | $SCH_3$ | 2-Cl-phenyl | 2-(methylaminosulfonyl)phenyl |
| 293 | $SCH_3$ | 2-Cl-phenyl | 1-pyrrolidinocarbonyl |
| 294 | $SCH_3$ | 2-Cl-phenyl | 2-(methylsulfonyl)phenyl |
| 295 | $SCH_3$ | 2-Cl-phenyl | 4-morpholino |
| 296 | $SCH_3$ | 2-Cl-phenyl | 2-(1'-$CF_3$-tetrazol-2-yl)phenyl |
| 297 | $SCH_3$ | 2-Cl-phenyl | 4-morpholinocarbonyl |
| 298 | $SCH_3$ | 2-Cl-phenyl | 2-methyl-1-imidazolyl |
| 299 | $SCH_3$ | 2-Cl-phenyl | 5-methyl-1-imidazolyl |
| 300 | $SCH_3$ | 2-Cl-phenyl | 2-methylsulfonyl-1-imidazolyl |
| 301 | $SCH_3$ | 2-F-phenyl | 2-(aminosulfonyl)phenyl |
| 302 | $SCH_3$ | 2-F-phenyl | 2-(methylaminosulfonyl)phenyl |
| 303 | $SCH_3$ | 2-F-phenyl | 1-pyrrolidinocarbonyl |
| 304 | $SCH_3$ | 2-F-phenyl | 2-(methylsulfonyl)phenyl |
| 305 | $SCH_3$ | 2-F-phenyl | 4-morpholino |
| 306 | $SCH_3$ | 2-F-phenyl | 2-(1'-$CF_3$-tetrazol-2-yl)phenyl |
| 307 | $SCH_3$ | 2-F-phenyl | 4-morpholinocarbonyl |
| 308 | $SCH_3$ | 2-F-phenyl | 2-methyl-1-imidazolyl |
| 309 | $SCH_3$ | 2-F-phenyl | 5-methyl-1-imidazolyl |
| 310 | $SCH_3$ | 2-F-phenyl | 2-methylsulfonyl-1-imidazolyl |
| 311 | $SCH_3$ | 2,6-diF-phenyl | 2-(aminosulfonyl)phenyl |
| 312 | $SCH_3$ | 2,6-diF-phenyl | 2-(methylaminosulfonyl)phenyl |
| 313 | $SCH_3$ | 2,6-diF-phenyl | 1-pyrrolidinocarbonyl |
| 314 | $SCH_3$ | 2,6-diF-phenyl | 2-(methylsulfonyl)phenyl |
| 315 | $SCH_3$ | 2,6-diF-phenyl | 4-morpholino |
| 316 | $SCH_3$ | 2,6-diF-phenyl | 2-(1'-$CF_3$-tetrazol-2-yl)phenyl |
| 317 | $SCH_3$ | 2,6-diF-phenyl | 4-morpholinocarbonyl |
| 318 | $SCH_3$ | 2,6-diF-phenyl | 2-methyl-1-imidazolyl |
| 319 | $SCH_3$ | 2,6-diF-phenyl | 5-methyl-1-imidazolyl |
| 320 | $SCH_3$ | 2,6-diF-phenyl | 2-methylsulfonyl-1-imidazolyl |
| 321 | $SOCH_3$ | phenyl | 2-(aminosulfonyl)phenyl |
| 322 | $SOCH_3$ | phenyl | 2-(methylaminosulfonyl)phenyl |
| 323 | $SOCH_3$ | phenyl | 1-pyrrolidinocarbonyl |
| 324 | $SOCH_3$ | phenyl | 2-(methylsulfonyl)phenyl |
| 325 | $SOCH_3$ | phenyl | 4-morpholino |
| 326 | $SOCH_3$ | phenyl | 2-(1'-$CF_3$-tetrazol-2-yl)phenyl |
| 327 | $SOCH_3$ | phenyl | 4-morpholinocarbonyl |
| 328 | $SOCH_3$ | phenyl | 2-methyl-1-imidazolyl |
| 329 | $SOCH_3$ | phenyl | 5-methyl-1-imidazolyl |
| 330 | $SOCH_3$ | phenyl | 2-methylsulfonyl-1-imidazolyl |
| 331 | $SOCH_3$ | 2-pyridyl | 2-(aminosulfonyl)phenyl |
| 332 | $SOCH_3$ | 2-pyridyl | 2-(methylaminosulfonyl)phenyl |
| 333 | $SOCH_3$ | 2-pyridyl | 1-pyrrolidinocarbonyl |
| 334 | $SOCH_3$ | 2-pyridyl | 2-(methylsulfonyl)phenyl |
| 335 | $SOCH_3$ | 2-pyridyl | 4-morpholino |
| 336 | $SOCH_3$ | 2-pyridyl | 2-(1'-$CF_3$-tetrazol-2-yl)phenyl |
| 337 | $SOCH_3$ | 2-pyridyl | 4-morpholinocarbonyl |
| 338 | $SOCH_3$ | 2-pyridyl | 2-methyl-1-imidazolyl |
| 339 | $SOCH_3$ | 2-pyridyl | 5-methyl-1-imidazolyl |
| 340 | $SOCH_3$ | 2-pyridyl | 2-methylsulfonyl-1-imidazolyl |
| 341 | $SOCH_3$ | 3-pyridyl | 2-(aminosulfonyl)phenyl |
| 342 | $SOCH_3$ | 3-pyridyl | 2-(methylaminosulfonyl)phenyl |
| 343 | $SOCH_3$ | 3-pyridyl | 1-pyrrolidinocarbonyl |
| 344 | $SOCH_3$ | 3-pyridyl | 2-(methylsulfonyl)phenyl |
| 345 | $SOCH_3$ | 3-pyridyl | 4-morpholino |
| 346 | $SOCH_3$ | 3-pyridyl | 2-(1'-$CF_3$-tetrazol-2-yl)phenyl |
| 347 | $SOCH_3$ | 3-pyridyl | 4-morpholinocarbonyl |
| 348 | $SOCH_3$ | 3-pyridyl | 2-methyl-1-imidazolyl |

TABLE 1-continued

| | | | |
|---|---|---|---|
| 349 | SOCH₃ | 3-pyridyl | 5-methyl-1-imidazolyl |
| 350 | SOCH₃ | 3-pyridyl | 2-methylsulfonyl-1-imidazolyl |
| 351 | SOCH₃ | 2-pyrimidyl | 2-(aminosulfonyl)phenyl |
| 352 | SOCH₃ | 2-pyrimidyl | 2-(methylaminosulfonyl)phenyl |
| 353 | SOCH₃ | 2-pyrimidyl | 1-pyrrolidinocarbonyl |
| 354 | SOCH₃ | 2-pyrimidyl | 2-(methylsulfonyl)phenyl |
| 355 | SOCH₃ | 2-pyrimidyl | 4-morpholino |
| 356 | SOCH₃ | 2-pyrimidyl | 2-(1'-CF₃-tetrazol-2-yl)phenyl |
| 357 | SOCH₃ | 2-pyrimidyl | 4-morpholinocarbonyl |
| 358 | SOCH₃ | 2-pyrimidyl | 2-methyl-1-imidazolyl |
| 359 | SOCH₃ | 2-pyrimidyl | 5-methyl-1-imidazolyl |
| 360 | SOCH₃ | 2-pyrimidyl | 2-methylsulfonyl-1-imidazolyl |
| 361 | SOCH₃ | 5-pyrimidyl | 2-(aminosulfonyl)phenyl |
| 362 | SOCH₃ | 5-pyrimidyl | 2-(methylaminosulfonyl)phenyl |
| 363 | SOCH₃ | 5-pyrimidyl | 1-pyrrolidinocarbonyl |
| 364 | SOCH₃ | 5-pyrimidyl | 2-(methylsulfonyl)phenyl |
| 365 | SOCH₃ | 5-pyrimidyl | 4-morpholino |
| 366 | SOCH₃ | 5-pyrimidyl | 2-(1'-CF₃-tetrazol-2-yl)phenyl |
| 367 | SOCH₃ | 5-pyrimidyl | 4-morpholinocarbonyl |
| 368 | SOCH₃ | 5-pyrimidyl | 2-methyl-1-imidazolyl |
| 369 | SOCH₃ | 5-pyrimidyl | 5-methyl-1-imidazolyl |
| 370 | SOCH₃ | 5-pyrimidyl | 2-methylsulfonyl-1-imidazolyl |
| 371 | SOCH₃ | 2-Cl-phenyl | 2-(aminosulfonyl)phenyl |
| 372 | SOCH₃ | 2-Cl-phenyl | 2-(methylaminosulfonyl)phenyl |
| 373 | SOCH₃ | 2-Cl-phenyl | 1-pyrrolidinocarbonyl |
| 374 | SOCH₃ | 2-Cl-phenyl | 2-(methylsulfonyl)phenyl |
| 375 | SOCH₃ | 2-Cl-phenyl | 4-morpholino |
| 376 | SOCH₃ | 2-Cl-phenyl | 2-(1'-CF₃-tetrazol-2-yl)phenyl |
| 377 | SOCH₃ | 2-Cl-phenyl | 4-morpholinocarbonyl |
| 378 | SOCH₃ | 2-Cl-phenyl | 2-methyl-1-imidazolyl |
| 379 | SOCH₃ | 2-Cl-phenyl | 5-methyl-1-imidazolyl |
| 380 | SOCH₃ | 2-Cl-phenyl | 2-methylsulfonyl-1-imidazolyl |
| 381 | SOCH₃ | 2-F-phenyl | 2-(aminosulfonyl)phenyl |
| 382 | SOCH₃ | 2-F-phenyl | 2-(methylaminosulfonyl)phenyl |
| 383 | SOCH₃ | 2-F-phenyl | 1-pyrrolidinocarbonyl |
| 384 | SOCH₃ | 2-F-phenyl | 2-(methylsulfonyl)phenyl |
| 385 | SOCH₃ | 2-F-phenyl | 4-morpholino |
| 386 | SOCH₃ | 2-F-phenyl | 2-(1'-CF₃-tetrazol-2-yl)phenyl |
| 387 | SOCH₃ | 2-F-phenyl | 4-morpholinocarbonyl |
| 388 | SOCH₃ | 2-F-phenyl | 2-methyl-1-imidazolyl |
| 389 | SOCH₃ | 2-F-phenyl | 5-methyl-1-imidazolyl |
| 390 | SOCH₃ | 2-F-phenyl | 2-methylsulfonyl-1-imidazolyl |
| 391 | SOCH₃ | 2,6-diF-phenyl | 2-(aminosulfonyl)phenyl |
| 392 | SOCH₃ | 2,6-diF-phenyl | 2-(methylaminosulfonyl)phenyl |
| 393 | SOCH₃ | 2,6-diF-phenyl | 1-pyrrolidinocarbonyl |
| 394 | SOCH₃ | 2,6-diF-phenyl | 2-(methylsulfonyl)phenyl |
| 395 | SOCH₃ | 2,6-diF-phenyl | 4-morpholino |
| 396 | SOCH₃ | 2,6-diF-phenyl | 2-(1'-CF₃-tetrazol-2-yl)phenyl |
| 397 | SOCH₃ | 2,6-diF-phenyl | 4-morpholinocarbonyl |
| 398 | SOCH₃ | 2,6-diF-phenyl | 2-methyl-1-imidazolyl |
| 399 | SOCH₃ | 2,6-diF-phenyl | 5-methyl-1-imidazolyl |
| 400 | SOCH₃ | 2,6-diF-phenyl | 2-methylsulfonyl-1-imidazolyl |
| 401 | SO₂CH₃ | phenyl | 2-(aminosulfonyl)phenyl |
| 402 | SO₂CH₃ | phenyl | 2-(methylaminosulfonyl)phenyl |
| 403 | SO₂CH₃ | phenyl | 1-pyrrolidinocarbonyl |
| 404 | SO₂CH₃ | phenyl | 2-(methylsulfonyl)phenyl |
| 405 | SO₂CH₃ | phenyl | 4-morpholino |
| 406 | SO₂CH₃ | phenyl | 2-(1'-CF₃-tetrazol-2-yl)phenyl |
| 407 | SO₂CH₃ | phenyl | 4-morpholinocarbonyl |
| 408 | SO₂CH₃ | phenyl | 2-methyl-1-imidazolyl |
| 409 | SO₂CH₃ | phenyl | 5-methyl-1-imidazolyl |
| 410 | SO₂CH₃ | phenyl | 2-methylsulfonyl-1-imidazolyl |
| 411 | SO₂CH₃ | 2-pyridyl | 2-(aminosulfonyl)phenyl |
| 412 | SO₂CH₃ | 2-pyridyl | 2-(methylaminosulfonyl)phenyl |
| 413 | SO₂CH₃ | 2-pyridyl | 1-pyrrolidinocarbonyl |
| 414 | SO₂CH₃ | 2-pyridyl | 2-(methylsulfonyl)phenyl |
| 415 | SO₂CH₃ | 2-pyridyl | 4-morpholino |
| 416 | SO₂CH₃ | 2-pyridyl | 2-(1'-CF₃-tetrazol-2-yl)phenyl |
| 417 | SO₂CH₃ | 2-pyridyl | 4-morpholinocarbonyl |
| 418 | SO₂CH₃ | 2-pyridyl | 2-methyl-1-imidazolyl |
| 419 | SO₂CH₃ | 2-pyridyl | 5-methyl-1-imidazolyl |
| 420 | SO₂CH₃ | 2-pyridyl | 2-methylsulfonyl-1-imidazolyl |
| 421 | SO₂CH₃ | 3-pyridyl | 2-(aminosulfonyl)phenyl |
| 422 | SO₂CH₃ | 3-pyridyl | 2-(methylaminosulfonyl)phenyl |
| 423 | SO₂CH₃ | 3-pyridyl | 1-pyrrolidinocarbonyl |
| 424 | SO₂CH₃ | 3-pyridyl | 2-(methylsulfonyl)phenyl |
| 425 | SO₂CH₃ | 3-pyridyl | 4-morpholino |
| 426 | SO₂CH₃ | 3-pyridyl | 2-(1'-CF₃-tetrazol-2-yl)phenyl |
| 427 | SO₂CH₃ | 3-pyridyl | 4-morpholinocarbonyl |

TABLE 1-continued

| | | | |
|---|---|---|---|
| 428 | SO$_2$CH$_3$ | 3-pyridyl | 2-methyl-1-imidazolyl |
| 429 | SO$_2$CH$_3$ | 3-pyridyl | 5-methyl-1-imidazolyl |
| 430 | SO$_2$CH$_3$ | 3-pyridyl | 2-methylsulfonyl-1-imidazolyl |
| 431 | SO$_2$CH$_3$ | 2-pyrimidyl | 2-(aminosulfonyl)phenyl |
| 432 | SO$_2$CH$_3$ | 2-pyrimidyl | 2-(methylaminosulfonyl)phenyl |
| 433 | SO$_2$CH$_3$ | 2-pyrimidyl | 1-pyrrolidinocarbonyl |
| 434 | SO$_2$CH$_3$ | 2-pyrimidyl | 2-(methylsulfonyl)phenyl |
| 435 | SO$_2$CH$_3$ | 2-pyrimidyl | 4-morpholino |
| 436 | SO$_2$CH$_3$ | 2-pyrimidyl | 2-(1'-CF$_3$-tetrazol-2-yl)phenyl |
| 437 | SO$_2$CH$_3$ | 2-pyrimidyl | 4-morpholinocarbonyl |
| 438 | SO$_2$CH$_3$ | 2-pyrimidyl | 2-methyl-1-imidazolyl |
| 439 | SO$_2$CH$_3$ | 2-pyrimidyl | 5-methyl-1-imidazolyl |
| 440 | SO$_2$CH$_3$ | 2-pyrimidyl | 2-methylsulfonyl-1-imidazolyl |
| 441 | SO$_2$CH$_3$ | 5-pyrimidyl | 2-(aminosulfonyl)phenyl |
| 442 | SO$_2$CH$_3$ | 5-pyrimidyl | 2-(methylaminosulfonyl)phenyl |
| 443 | SO$_2$CH$_3$ | 5-pyrimidyl | 1-pyrrolidinocarbonyl |
| 444 | SO$_2$CH$_3$ | 5-pyrimidyl | 2-(methylsulfonyl)phenyl |
| 445 | SO$_2$CH$_3$ | 5-pyrimidyl | 4-morpholino |
| 446 | SO$_2$CH$_3$ | 5-pyrimidyl | 2-(1'-CF$_3$-tetrazol-2-yl)phenyl |
| 447 | SO$_2$CH$_3$ | 5-pyrimidyl | 4-morpholinocarbonyl |
| 448 | SO$_2$CH$_3$ | 5-pyrimidyl | 2-methyl-1-imidazolyl |
| 449 | SO$_2$CH$_3$ | 5-pyrimidyl | 5-methyl-1-imidazolyl |
| 450 | SO$_2$CH$_3$ | 5-pyrimidyl | 2-methylsulfonyl-1-imidazolyl |
| 451 | SO$_2$CH$_3$ | 2-Cl-phenyl | 2-(aminosulfonyl)phenyl |
| 452 | SO$_2$CH$_3$ | 2-Cl-phenyl | 2-(methylaminosulfonyl)phenyl |
| 453 | SO$_2$CH$_3$ | 2-Cl-phenyl | 1-pyrrolidinocarbonyl |
| 454 | SO$_2$CH$_3$ | 2-Cl-phenyl | 2-(methylsulfonyl)phenyl |
| 455 | SO$_2$CH$_3$ | 2-Cl-phenyl | 4-morpholino |
| 456 | SO$_2$CH$_3$ | 2-Cl-phenyl | 2-(1'-CF$_3$-tetrazol-2-yl)phenyl |
| 457 | SO$_2$CH$_3$ | 2-Cl-phenyl | 4-morpholinocarbonyl |
| 458 | SO$_2$CH$_3$ | 2-Cl-phenyl | 2-methyl-1-imidazolyl |
| 459 | SO$_2$CH$_3$ | 2-Cl-phenyl | 5-methyl-1-imidazolyl |
| 460 | SO$_2$CH$_3$ | 2-Cl-phenyl | 2-methylsulfonyl-1-imidazolyl |
| 461 | SO$_2$CH$_3$ | 2-F-phenyl | 2-(aminosulfonyl)phenyl |
| 462 | SO$_2$CH$_3$ | 2-F-phenyl | 2-(methylaminosulfonyl)phenyl |
| 463 | SO$_2$CH$_3$ | 2-F-phenyl | 1-pyrrolidinocarbonyl |
| 464 | SO$_2$CH$_3$ | 2-F-phenyl | 2-(methylsulfonyl)phenyl |
| 465 | SO$_2$CH$_3$ | 2-F-phenyl | 4-morpholino |
| 466 | SO$_2$CH$_3$ | 2-F-phenyl | 2-(1'-CF$_3$-tetrazol-2-yl)phenyl |
| 467 | SO$_2$CH$_3$ | 2-F-phenyl | 4-morpholinocarbonyl |
| 468 | SO$_2$CH$_3$ | 2-F-phenyl | 2-methyl-1-imidazolyl |
| 469 | SO$_2$CH$_3$ | 2-F-phenyl | 5-methyl-1-imidazolyl |
| 470 | SO$_2$CH$_3$ | 2-F-phenyl | 2-methylsulfonyl-1-imidazolyl |
| 471 | SO$_2$CH$_3$ | 2,6-diF-phenyl | 2-(aminosulfonyl)phenyl |
| 472 | SO$_2$CH$_3$ | 2,6-diF-phenyl | 2-(methylaminosulfonyl)phenyl |
| 473 | SO$_2$CH$_3$ | 2,6-diF-phenyl | 1-pyrrolidinocarbonyl |
| 474 | SO$_2$CH$_3$ | 2,6-diF-phenyl | 2-(methylsulfonyl)phenyl |
| 475 | SO$_2$CH$_3$ | 2,6-diF-phenyl | 4-morpholino |
| 476 | SO$_2$CH$_3$ | 2,6-diF-phenyl | 2-(1'-CF$_3$-tetrazol-2-yl)phenyl |
| 477 | SO$_2$CH$_3$ | 2,6-diF-phenyl | 4-morpholinocarbonyl |
| 478 | SO$_2$CH$_3$ | 2,6-diF-phenyl | 2-methyl-1-imidazolyl |
| 479 | SO$_2$CH$_3$ | 2,6-diF-phenyl | 5-methyl-1-imidazolyl |
| 480 | SO$_2$CH$_3$ | 2,6-diF-phenyl | 2-methylsulfonyl-1-imidazolyl |
| 481 | CH$_2$NH—SO$_2$CH$_3$ | phenyl | 2-(aminosulfonyl)phenyl |
| 482 | CH$_2$NH—SO$_2$CH$_3$ | phenyl | 2-(methylaminosulfonyl)phenyl |
| 483 | CH$_2$NH—SO$_2$CH$_3$ | phenyl | 1-pyrrolidinocarbonyl |
| 484 | CH$_2$NH—SO$_2$CH$_3$ | phenyl | 2-(methylsulfonyl)phenyl |
| 485 | CH$_2$NH—SO$_2$CH$_3$ | phenyl | 4-morpholino |
| 486 | CH$_2$NH—SO$_2$CH$_3$ | phenyl | 2-(1'-CF$_3$-tetrazol-2-yl)phenyl |
| 487 | CH$_2$NH—SO$_2$CH$_3$ | phenyl | 4-morpholinocarbonyl |
| 488 | CH$_2$NH—SO$_2$CH$_3$ | phenyl | 2-methyl-1-imidazolyl |
| 489 | CH$_2$NH—SO$_2$CH$_3$ | phenyl | 5-methyl-1-imidazolyl |
| 490 | CH$_2$NH—SO$_2$CH$_3$ | phenyl | 2-methylsulfonyl-1-imidazolyl |
| 491 | CH$_2$NH—SO$_2$CH$_3$ | 2-pyridyl | 2-(aminosulfonyl)phenyl |
| 492 | CH$_2$NH—SO$_2$CH$_3$ | 2-pyridyl | 2-(methylaminosulfonyl)phenyl |
| 493 | CH$_2$NH—SO$_2$CH$_3$ | 2-pyridyl | 1-pyrrolidinocarbonyl |
| 494 | CH$_2$NH—SO$_2$CH$_3$ | 2-pyridyl | 2-(methylsulfonyl)phenyl |
| 495 | CH$_2$NH—SO$_2$CH$_3$ | 2-pyridyl | 4-morpholino |
| 496 | CH$_2$NH—SO$_2$CH$_3$ | 2-pyridyl | 2-(1'-CF$_3$-tetrazol-2-yl)phenyl |
| 497 | CH$_2$NH—SO$_2$CH$_3$ | 2-pyridyl | 4-morpholinocarbonyl |
| 498 | CH$_2$NH—SO$_2$CH$_3$ | 2-pyridyl | 2-methyl-1-imidazolyl |
| 499 | CH$_2$NH—SO$_2$CH$_3$ | 2-pyridyl | 5-methyl-1-imidazolyl |
| 500 | CH$_2$NH—SO$_2$CH$_3$ | 2-pyridyl | 2-methylsulfonyl-1-imidazolyl |
| 501 | CH$_2$NH—SO$_2$CH$_3$ | 3-pyridyl | 2-(aminosulfonyl)phenyl |
| 502 | CH$_2$NH—SO$_2$CH$_3$ | 3-pyridyl | 2-(methylaminosulfonyl)phenyl |
| 503 | CH$_2$NH—SO$_2$CH$_3$ | 3-pyridyl | 1-pyrrolidinocarbonyl |
| 504 | CH$_2$NH—SO$_2$CH$_3$ | 3-pyridyl | 2-(methylsulfonyl)phenyl |
| 505 | CH$_2$NH—SO$_2$CH$_3$ | 3-pyridyl | 4-morpholino |
| 506 | CH$_2$NH—SO$_2$CH$_3$ | 3-pyridyl | 2-(1'-CF$_3$-tetrazol-2-yl)phenyl |

TABLE 1-continued

| | | | |
|---|---|---|---|
| 507 | CH$_2$NH—SO$_2$CH$_3$ | 3-pyridyl | 4-morpholinocarbonyl |
| 508 | CH$_2$NH—SO$_2$CH$_3$ | 3-pyridyl | 2-methyl-1-imidazolyl |
| 509 | CH$_2$NH—SO$_2$CH$_3$ | 3-pyridyl | 5-methyl-1-imidazolyl |
| 510 | CH$_2$NH—SO$_2$CH$_3$ | 3-pyridyl | 2-methylsulfonyl-1-imidazolyl |
| 511 | CH$_2$NH—SO$_2$CH$_3$ | 2-pyrimidyl | 2-(aminosulfonyl)phenyl |
| 512 | CH$_2$NH—SO$_2$CH$_3$ | 2-pyrimidyl | 2-(methylaminosulfonyl)phenyl |
| 513 | CH$_2$NH—SO$_2$CH$_3$ | 2-pyrimidyl | 1-pyrrolidinocarbonyl |
| 514 | CH$_2$NH—SO$_2$CH$_3$ | 2-pyrimidyl | 2-(methylsulfonyl)phenyl |
| 515 | CH$_2$NH—SO$_2$CH$_3$ | 2-pyrimidyl | 4-morpholino |
| 516 | CH$_2$NH—SO$_2$CH$_3$ | 2-pyrimidyl | 2-(1'-CF$_3$-tetrazol-2-yl)phenyl |
| 517 | CH$_2$NH—SO$_2$CH$_3$ | 2-pyrimidyl | 4-morpholinocarbonyl |
| 518 | CH$_2$NH—SO$_2$CH$_3$ | 2-pyrimidyl | 2-methyl-1-imidazolyl |
| 519 | CH$_2$NH—SO$_2$CH$_3$ | 2-pyrimidyl | 5-methyl-1-imidazolyl |
| 520 | CH$_2$NH—SO$_2$CH$_3$ | 2-pyrimidyl | 2-methylsulfonyl-1-imidazolyl |
| 521 | CH$_2$NH—SO$_2$CH$_3$ | 5-pyrimidyl | 2-(aminosulfonyl)phenyl |
| 522 | CH$_2$NH—SO$_2$CH$_3$ | 5-pyrimidyl | 2-(methylaminosulfonyl)phenyl |
| 523 | CH$_2$NH—SO$_2$CH$_3$ | 5-pyrimidyl | 1-pyrrolidinocarbonyl |
| 524 | CH$_2$NH—SO$_2$CH$_3$ | 5-pyrimidyl | 2-(methylsulfonyl)phenyl |
| 525 | CH$_2$NH—SO$_2$CH$_3$ | 5-pyrimidyl | 4-morpholino |
| 526 | CH$_2$NH—SO$_2$CH$_3$ | 5-pyrimidyl | 2-(1'-CF$_3$-tetrazol-2-yl)phenyl |
| 527 | CH$_2$NH—SO$_2$CH$_3$ | 5-pyrimidyl | 4-morpholinocarbonyl |
| 528 | CH$_2$NH—SO$_2$CH$_3$ | 5-pyrimidyl | 2-methyl-1-imidazolyl |
| 529 | CH$_2$NH—SO$_2$CH$_3$ | 5-pyrimidyl | 5-methyl-1-imidazolyl |
| 530 | CH$_2$NH—SO$_2$CH$_3$ | 5-pyrimidyl | 2-methylsulfonyl-1-imidazolyl |
| 531 | CH$_2$NH—SO$_2$CH$_3$ | 2-Cl-phenyl | 2-(aminosulfonyl)phenyl |
| 532 | CH$_2$NH—SO$_2$CH$_3$ | 2-Cl-phenyl | 2-(methylaminosulfonyl)phenyl |
| 533 | CH$_2$NH—SO$_2$CH$_3$ | 2-Cl-phenyl | 1-pyrrolidinocarbonyl |
| 534 | CH$_2$NH—SO$_2$CH$_3$ | 2-Cl-phenyl | 2-(methylsulfonyl)phenyl |
| 535 | CH$_2$NH—SO$_2$CH$_3$ | 2-Cl-phenyl | 4-morpholino |
| 536 | CH$_2$NH—SO$_2$CH$_3$ | 2-Cl-phenyl | 2-(1'-CF$_3$-tetrazol-2-yl)phenyl |
| 537 | CH$_2$NH—SO$_2$CH$_3$ | 2-Cl-phenyl | 4-morpholinocarbonyl |
| 538 | CH$_2$NH—SO$_2$CH$_3$ | 2-Cl-phenyl | 2-methyl-1-imidazolyl |
| 539 | CH$_2$NH—SO$_2$CH$_3$ | 2-Cl-phenyl | 5-methyl-1-imidazolyl |
| 540 | CH$_2$NH—SO$_2$CH$_3$ | 2-Cl-phenyl | 2-methylsulfonyl-1-imidazolyl |
| 541 | CH$_2$NH—SO$_2$CH$_3$ | 2-F-phenyl | 2-(aminosulfonyl)phenyl |
| 542 | CH$_2$NH—SO$_2$CH$_3$ | 2-F-phenyl | 2-(methylaminosulfonyl)phenyl |
| 543 | CH$_2$NH—SO$_2$CH$_3$ | 2-F-phenyl | 1-pyrrolidinocarbonyl |
| 544 | CH$_2$NH—SO$_2$CH$_3$ | 2-F-phenyl | 2-(methylsulfonyl)phenyl |
| 545 | CH$_2$NH—SO$_2$CH$_3$ | 2-F-phenyl | 4-morpholino |
| 546 | CH$_2$NH—SO$_2$CH$_3$ | 2-F-phenyl | 2-(1'-CF$_3$-tetrazol-2-yl)phenyl |
| 547 | CH$_2$NH—SO$_2$CH$_3$ | 2-F-phenyl | 4-morpholinocarbonyl |
| 548 | CH$_2$NH—SO$_2$CH$_3$ | 2-F-phenyl | 2-methyl-1-imidazolyl |
| 549 | CH$_2$NH—SO$_2$CH$_3$ | 2-F-phenyl | 5-methyl-1-imidazolyl |
| 550 | CH$_2$NH—SO$_2$CH$_3$ | 2-F-phenyl | 2-methylsulfonyl-1-imidazolyl |
| 551 | CH$_2$NH—SO$_2$CH$_3$ | 2,6-diF-phenyl | 2-(aminosulfonyl)phenyl |
| 552 | CH$_2$NH—SO$_2$CH$_3$ | 2,6-diF-phenyl | 2-(methylaminosulfonyl)phenyl |
| 553 | CH$_2$NH—SO$_2$CH$_3$ | 2,6-diF-phenyl | 1-pyrrolidinocarbonyl |
| 554 | CH$_2$NH—SO$_2$CH$_3$ | 2,6-diF-phenyl | 2-(methylsulfonyl)phenyl |
| 555 | CH$_2$NH—SO$_2$CH$_3$ | 2,6-diF-phenyl | 4-morpholino |
| 556 | CH$_2$NH—SO$_2$CH$_3$ | 2,6-diF-phenyl | 2-(1'-CF$_3$-tetrazol-2-yl)phenyl |
| 557 | CH$_2$NH—SO$_2$CH$_3$ | 2,6-diF-phenyl | 4-morpholinocarbonyl |
| 558 | CH$_2$NH—SO$_2$CH$_3$ | 2,6-diF-phenyl | 2-methyl-1-imidazolyl |
| 559 | CH$_2$NH—SO$_2$CH$_3$ | 2,6-diF-phenyl | 5-methyl-1-imidazolyl |
| 560 | CH$_2$NH—SO$_2$CH$_3$ | 2,6-diF-phenyl | 2-methylsulfonyl-1-imidazolyl |
| 561 | Cl | phenyl | 2-(aminosulfonyl)phenyl |
| 562 | Cl | phenyl | 2-(methylaminosulfonyl)phenyl |
| 563 | Cl | phenyl | 1-pyrrolidinocarbonyl |
| 564 | Cl | phenyl | 2-(methylsulfonyl)phenyl |
| 565 | Cl | phenyl | 4-morpholino |
| 566 | Cl | phenyl | 2-(1'-CF$_3$-tetrazol-2-yl)phenyl |
| 567 | Cl | phenyl | 4-morpholinocarbonyl |
| 568 | Cl | phenyl | 2-methyl-1-imidazolyl |
| 569 | Cl | phenyl | 5-methyl-1-imidazolyl |
| 570 | Cl | phenyl | 2-methylsulfonyl-1-imidazolyl |
| 571 | Cl | 2-pyridyl | 2-(aminosulfonyl)phenyl |
| 572 | Cl | 2-pyridyl | 2-(methylaminosulfonyl)phenyl |
| 573 | Cl | 2-pyridyl | 1-pyrrolidinocarbonyl |
| 574 | Cl | 2-pyridyl | 2-(methylsulfonyl)phenyl |
| 575 | Cl | 2-pyridyl | 4-morpholino |
| 576 | Cl | 2-pyridyl | 2-(1'-CF$_3$-tetrazol-2-yl)phenyl |
| 577 | Cl | 2-pyridyl | 4-morpholinocarbonyl |
| 578 | Cl | 2-pyridyl | 2-methyl-1-imidazolyl |
| 579 | Cl | 2-pyridyl | 5-methyl-1-imidazolyl |
| 580 | Cl | 2-pyridyl | 2-methylsulfonyl-1-imidazolyl |
| 581 | Cl | 3-pyridyl | 2-(aminosulfonyl)phenyl |
| 582 | Cl | 3-pyridyl | 2-(methylaminosulfonyl)phenyl |
| 583 | Cl | 3-pyridyl | 1-pyrrolidinocarbonyl |
| 584 | Cl | 3-pyridyl | 2-(methylsulfonyl)phenyl |
| 585 | Cl | 3-pyridyl | 4-morpholino |

TABLE 1-continued

| | | | |
|---|---|---|---|
| 586 | Cl | 3-pyridyl | 2-(1'-CF$_3$-tetrazol-2-yl)phenyl |
| 587 | Cl | 3-pyridyl | 4-morpholinocarbonyl |
| 588 | Cl | 3-pyridyl | 2-methyl-1-imidazolyl |
| 589 | Cl | 3-pyridyl | 5-methyl-1-imidazolyl |
| 590 | Cl | 3-pyridyl | 2-methylsulfonyl-1-imidazolyl |
| 591 | Cl | 2-pyrimidyl | 2-(aminosulfonyl)phenyl |
| 592 | Cl | 2-pyrimidyl | 2-(methylaminosulfonyl)phenyl |
| 593 | Cl | 2-pyrimidyl | 1-pyrrolidinocarbonyl |
| 594 | Cl | 2-pyrimidyl | 2-(methylsulfonyl)phenyl |
| 595 | Cl | 2-pyrimidyl | 4-morpholino |
| 596 | Cl | 2-pyrimidyl | 2-(1'-CF$_3$-tetrazol-2-yl)phenyl |
| 597 | Cl | 2-pyrimidyl | 4-morpholinocarbonyl |
| 598 | Cl | 2-pyrimidyl | 2-methyl-1-imidazolyl |
| 599 | Cl | 2-pyrimidyl | 5-methyl-1-imidazolyl |
| 600 | Cl | 2-pyrimidyl | 2-methylsulfonyl-1-imidazolyl |
| 601 | Cl | 5-pyrimidyl | 2-(aminosulfonyl)phenyl |
| 602 | Cl | 5-pyrimidyl | 2-(methylaminosulfonyl)phenyl |
| 603 | Cl | 5-pyrimidyl | 1-pyrrolidinocarbonyl |
| 604 | Cl | 5-pyrimidyl | 2-(methylsulfonyl)phenyl |
| 605 | Cl | 5-pyrimidyl | 4-morpholino |
| 606 | Cl | 5-pyrimidyl | 2-(1'-CF$_3$-tetrazol-2-yl)phenyl |
| 607 | Cl | 5-pyrimidyl | 4-morpholinocarbonyl |
| 608 | Cl | 5-pyrimidyl | 2-methyl-1-imidazolyl |
| 609 | Cl | 5-pyrimidyl | 5-methyl-1-imidazolyl |
| 610 | Cl | 5-pyrimidyl | 2-methylsulfonyl-1-imidazolyl |
| 611 | Cl | 2-Cl-phenyl | 2-(aminosulfonyl)phenyl |
| 612 | Cl | 2-Cl-phenyl | 2-(methylaminosulfonyl)phenyl |
| 613 | Cl | 2-Cl-phenyl | 1-pyrrolidinocarbonyl |
| 614 | Cl | 2-Cl-phenyl | 2-(methylsulfonyl)phenyl |
| 615 | Cl | 2-Cl-phenyl | 4-morpholino |
| 616 | Cl | 2-Cl-phenyl | 2-(1'-CF$_3$-tetrazol-2-yl)phenyl |
| 617 | Cl | 2-Cl-phenyl | 4-morpholinocarbonyl |
| 618 | Cl | 2-Cl-phenyl | 2-methyl-1-imidazolyl |
| 619 | Cl | 2-Cl-phenyl | 5-methyl-1-imidazolyl |
| 620 | Cl | 2-Cl-phenyl | 2-methylsulfonyl-1-imidazolyl |
| 621 | Cl | 2-F-phenyl | 2-(aminosulfonyl)phenyl |
| 622 | Cl | 2-F-phenyl | 2-(methylaminosulfonyl)phenyl |
| 623 | Cl | 2-F-phenyl | 1-pyrrolidinocarbonyl |
| 624 | Cl | 2-F-phenyl | 2-(methylsulfonyl)phenyl |
| 625 | Cl | 2-F-phenyl | 4-morpholino |
| 626 | Cl | 2-F-phenyl | 2-(1'-CF$_3$-tetrazol-2-yl)phenyl |
| 627 | Cl | 2-F-phenyl | 4-morpholinocarbonyl |
| 628 | Cl | 2-F-phenyl | 2-methyl-1-imidazolyl |
| 629 | Cl | 2-F-phenyl | 5-methyl-1-imidazolyl |
| 630 | Cl | 2-F-phenyl | 2-methylsulfonyl-1-imidazolyl |
| 631 | Cl | 2,6-diF-phenyl | 2-(aminosulfonyl)phenyl |
| 632 | Cl | 2,6-diF-phenyl | 2-(methylaminosulfonyl)phenyl |
| 633 | Cl | 2,6-diF-phenyl | 1-pyrrolidinocarbonyl |
| 634 | Cl | 2,6-diF-phenyl | 2-(methylsulfonyl)phenyl |
| 635 | Cl | 2,6-diF-phenyl | 4-morpholino |
| 636 | Cl | 2,6-diF-phenyl | 2-(1'-CF$_3$-tetrazol-2-yl)phenyl |
| 637 | Cl | 2,6-diF-phenyl | 4-morpholinocarbonyl |
| 638 | Cl | 2,6-diF-phenyl | 2-methyl-1-imidazolyl |
| 639 | Cl | 2,6-diF-phenyl | 5-methyl-1-imidazolyl |
| 640 | Cl | 2,6-diF-phenyl | 2-methylsulfonyl-1-imidazolyl |
| 641 | F | phenyl | 2-(aminosulfonyl)phenyl |
| 642 | F | phenyl | 2-(methylaminosulfonyl)phenyl |
| 643 | F | phenyl | 1-pyrrolidinocarbonyl |
| 644 | F | phenyl | 2-(methylsulfonyl)phenyl |
| 645 | F | phenyl | 4-morpholino |
| 646 | F | phenyl | 2-(1'-CF$_3$-tetrazol-2-yl)phenyl |
| 647 | F | phenyl | 4-morpholinocarbonyl |
| 648 | F | phenyl | 2-methyl-1-imidazolyl |
| 649 | F | phenyl | 5-methyl-1-imidazolyl |
| 650 | F | phenyl | 2-methylsulfonyl-1-imidazolyl |
| 651 | F | 2-pyridyl | 2-(aminosulfonyl)phenyl |
| 652 | F | 2-pyridyl | 2-(methylaminosulfonyl)phenyl |
| 653 | F | 2-pyridyl | 1-pyrrolidinocarbonyl |
| 654 | F | 2-pyridyl | 2-(methylsulfonyl)phenyl |
| 655 | F | 2-pyridyl | 4-morpholino |
| 656 | F | 2-pyridyl | 2-(1'-CF$_3$-tetrazol-2-yl)phenyl |
| 657 | F | 2-pyridyl | 4-morpholinocarbonyl |
| 658 | F | 2-pyridyl | 2-methyl-1-imidazolyl |
| 659 | F | 2-pyridyl | 5-methyl-1-imidazolyl |
| 660 | F | 2-pyridyl | 2-methylsulfonyl-1-imidazolyl |
| 661 | F | 3-pyridyl | 2-(aminosulfonyl)phenyl |
| 662 | F | 3-pyridyl | 2-(methylaminosulfonyl)phenyl |
| 663 | F | 3-pyridyl | 1-pyrrolidinocarbonyl |
| 664 | F | 3-pyridyl | 2-(methylsulfonyl)phenyl |

TABLE 1-continued

| | | | |
|---|---|---|---|
| 665 | F | 3-pyridyl | 4-morpholino |
| 666 | F | 3-pyridyl | 2-(1'-$CF_3$-tetrazol-2-yl)phenyl |
| 667 | F | 3-pyridyl | 4-morpholinocarbonyl |
| 668 | F | 3-pyridyl | 2-methyl-1-imidazolyl |
| 669 | F | 3-pyridyl | 5-methyl-1-imidazolyl |
| 670 | F | 3-pyridyl | 2-methylsulfonyl-1-imidazolyl |
| 671 | F | 2-pyrimidyl | 2-(aminosulfonyl)phenyl |
| 672 | F | 2-pyrimidyl | 2-(methylaminosulfonyl)phenyl |
| 673 | F | 2-pyrimidyl | 1-pyrrolidinocarbonyl |
| 674 | F | 2-pyrimidyl | 2-(methylsulfonyl)phenyl |
| 675 | F | 2-pyrimidyl | 4-morpholino |
| 676 | F | 2-pyrimidyl | 2-(1'-$CF_3$-tetrazol-2-yl)phenyl |
| 677 | F | 2-pyrimidyl | 4-morpholinocarbonyl |
| 678 | F | 2-pyrimidyl | 2-methyl-1-imidazolyl |
| 679 | F | 2-pyrimidyl | 5-methyl-1-imidazolyl |
| 680 | F | 2-pyrimidyl | 2-methylsulfonyl-1-imidazolyl |
| 681 | F | 5-pyrimidyl | 2-(aminosulfonyl)phenyl |
| 682 | F | 5-pyrimidyl | 2-(methylaminosulfonyl)phenyl |
| 683 | F | 5-pyrimidyl | 1-pyrrolidinocarbonyl |
| 684 | F | 5-pyrimidyl | 2-(methylsulfonyl)phenyl |
| 685 | F | 5-pyrimidyl | 4-morpholino |
| 686 | F | 5-pyrimidyl | 2-(1'-$CF_3$-tetrazol-2-yl)phenyl |
| 687 | F | 5-pyrimidyl | 4-morpholinocarbonyl |
| 688 | F | 5-pyrimidyl | 2-methyl-1-imidazolyl |
| 689 | F | 5-pyrimidyl | 5-methyl-1-imidazolyl |
| 690 | F | 5-pyrimidyl | 2-methylsulfonyl-1-imidazolyl |
| 691 | F | 2-Cl-phenyl | 2-(aminosulfonyl)phenyl |
| 692 | F | 2-Cl-phenyl | 2-(methylaminosulfonyl)phenyl |
| 693 | F | 2-Cl-phenyl | 1-pyrrolidinocarbonyl |
| 694 | F | 2-Cl-phenyl | 2-(methylsulfonyl)phenyl |
| 695 | F | 2-Cl-phenyl | 4-morpholino |
| 696 | F | 2-Cl-phenyl | 2-(1'-$CF_3$-tetrazol-2-yl)phenyl |
| 697 | F | 2-Cl-phenyl | 4-morpholinocarbonyl |
| 698 | F | 2-Cl-phenyl | 2-methyl-1-imidazolyl |
| 699 | F | 2-Cl-phenyl | 5-methyl-1-imidazolyl |
| 700 | F | 2-Cl-phenyl | 2-methylsulfonyl-1-imidazolyl |
| 701 | F | 2-F-phenyl | 2-(aminosulfonyl)phenyl |
| 702 | F | 2-F-phenyl | 2-(methylaminosulfonyl)phenyl |
| 703 | F | 2-F-phenyl | 1-pyrrolidinocarbonyl |
| 704 | F | 2-F-phenyl | 2-(methylsulfonyl)phenyl |
| 705 | F | 2-F-phenyl | 4-morpholino |
| 706 | F | 2-F-phenyl | 2-(1'-$CF_3$-tetrazol-2-yl)phenyl |
| 707 | F | 2-F-phenyl | 4-morpholinocarbonyl |
| 708 | F | 2-F-phenyl | 2-methyl-1-imidazolyl |
| 709 | F | 2-F-phenyl | 5-methyl-1-imidazolyl |
| 710 | F | 2-F-phenyl | 2-methylsulfonyl-1-imidazolyl |
| 711 | F | 2,6-diF-phenyl | 2-(aminosulfonyl)phenyl |
| 712 | F | 2,6-diF-phenyl | 2-(methylaminosulfonyl)phenyl |
| 713 | F | 2,6-diF-phenyl | 1-pyrrolidinocarbonyl |
| 714 | F | 2,6-diF-phenyl | 2-(methylsulfonyl)phenyl |
| 715 | F | 2,6-diF-phenyl | 4-morpholino |
| 716 | F | 2,6-diF-phenyl | 2-(1'-$CF_3$-tetrazol-2-yl)phenyl |
| 717 | F | 2,6-diF-phenyl | 4-morpholinocarbonyl |
| 718 | F | 2,6-diF-phenyl | 2-methyl-1-imidazolyl |
| 719 | F | 2,6-diF-phenyl | 5-methyl-1-imidazolyl |
| 720 | F | 2,6-diF-phenyl | 2-methylsulfonyl-1-imidazolyl |
| 721 | $CO_2CH_3$ | phenyl | 2-(aminosulfonyl)phenyl |
| 722 | $CO_2CH_3$ | phenyl | 2-(methylaminosulfonyl)phenyl |
| 723 | $CO_2CH_3$ | phenyl | 1-pyrrolidinocarbonyl |
| 724 | $CO_2CH_3$ | phenyl | 2-(methylsulfonyl)phenyl |
| 725 | $CO_2CH_3$ | phenyl | 4-morpholino |
| 726 | $CO_2CH_3$ | phenyl | 2-(1'-$CF_3$-tetrazol-2-yl)phenyl |
| 727 | $CO_2CH_3$ | phenyl | 4-morpholinocarbonyl |
| 728 | $CO_2CH_3$ | phenyl | 2-methyl-1-imidazolyl |
| 729 | $CO_2CH_3$ | phenyl | 5-methyl-1-imidazolyl |
| 730 | $CO_2CH_3$ | phenyl | 2-methylsulfonyl-1-imidazolyl |
| 731 | $CO_2CH_3$ | 2-pyridyl | 2-(aminosulfonyl)phenyl |
| 732 | $CO_2CH_3$ | 2-pyridyl | 2-(methylaminosulfonyl)phenyl |
| 733 | $CO_2CH_3$ | 2-pyridyl | 1-pyrrolidinocarbonyl |
| 734 | $CO_2CH_3$ | 2-pyridyl | 2-(methylsulfonyl)phenyl |
| 735 | $CO_2CH_3$ | 2-pyridyl | 4-morpholino |
| 736 | $CO_2CH_3$ | 2-pyridyl | 2-(1'-$CF_3$-tetrazol-2-yl)phenyl |
| 737 | $CO_2CH_3$ | 2-pyridyl | 4-morpholinocarbonyl |
| 738 | $CO_2CH_3$ | 2-pyridyl | 2-methyl-1-imidazolyl |
| 739 | $CO_2CH_3$ | 2-pyridyl | 5-methyl-1-imidazolyl |
| 740 | $CO_2CH_3$ | 2-pyridyl | 2-methylsulfonyl-1-imidazolyl |
| 741 | $CO_2CH_3$ | 3-pyridyl | 2-(aminosulfonyl)phenyl |
| 742 | $CO_2CH_3$ | 3-pyridyl | 2-(methylaminosulfonyl)phenyl |
| 743 | $CO_2CH_3$ | 3-pyridyl | 1-pyrrolidinocarbonyl |

TABLE 1-continued

| | | | |
|---|---|---|---|
| 744 | $CO_2CH_3$ | 3-pyridyl | 2-(methylsulfonyl)phenyl |
| 745 | $CO_2CH_3$ | 3-pyridyl | 4-morpholino |
| 746 | $CO_2CH_3$ | 3-pyridyl | 2-(1'-$CF_3$-tetrazol-2-yl)phenyl |
| 747 | $CO_2CH_3$ | 3-pyridyl | 4-morpholinocarbonyl |
| 748 | $CO_2CH_3$ | 3-pyridyl | 2-methyl-1-imidazolyl |
| 749 | $CO_2CH_3$ | 3-pyridyl | 5-methyl-1-imidazolyl |
| 750 | $CO_2CH_3$ | 3-pyridyl | 2-methylsulfonyl-1-imidazolyl |
| 751 | $CO_2CH_3$ | 2-pyrimidyl | 2-(aminosulfonyl)phenyl |
| 752 | $CO_2CH_3$ | 2-pyrimidyl | 2-(methylaminosulfonyl)phenyl |
| 753 | $CO_2CH_3$ | 2-pyrimidyl | 1-pyrrolidinocarbonyl |
| 754 | $CO_2CH_3$ | 2-pyrimidyl | 2-(methylsulfonyl)phenyl |
| 755 | $CO_2CH_3$ | 2-pyrimidyl | 4-morpholino |
| 756 | $CO_2CH_3$ | 2-pyrimidyl | 2-(1'-$CF_3$-tetrazol-2-yl)phenyl |
| 757 | $CO_2CH_3$ | 2-pyrimidyl | 4-morpholinocarbonyl |
| 758 | $CO_2CH_3$ | 2-pyrimidyl | 2-methyl-1-imidazolyl |
| 759 | $CO_2CH_3$ | 2-pyrimidyl | 5-methyl-1-imidazolyl |
| 760 | $CO_2CH_3$ | 2-pyrimidyl | 2-methylsulfonyl-1-imidazolyl |
| 761 | $CO_2CH_3$ | 5-pyrimidyl | 2-(aminosulfonyl)phenyl |
| 762 | $CO_2CH_3$ | 5-pyrimidyl | 2-(methylaminosulfonyl)phenyl |
| 763 | $CO_2CH_3$ | 5-pyrimidyl | 1-pyrrolidinocarbonyl |
| 764 | $CO_2CH_3$ | 5-pyrimidyl | 2-(methylsulfonyl)phenyl |
| 765 | $CO_2CH_3$ | 5-pyrimidyl | 4-morpholino |
| 766 | $CO_2CH_3$ | 5-pyrimidyl | 2-(1'-$CF_3$-tetrazol-2-yl)phenyl |
| 767 | $CO_2CH_3$ | 5-pyrimidyl | 4-morpholinocarbonyl |
| 768 | $CO_2CH_3$ | 5-pyrimidyl | 2-methyl-1-imidazolyl |
| 769 | $CO_2CH_3$ | 5-pyrimidyl | 5-methyl-1-imidazolyl |
| 770 | $CO_2CH_3$ | 5-pyrimidyl | 2-methylsulfonyl-1-imidazolyl |
| 771 | $CO_2CH_3$ | 2-Cl-phenyl | 2-(aminosulfonyl)phenyl |
| 772 | $CO_2CH_3$ | 2-Cl-phenyl | 2-(methylaminosulfonyl)phenyl |
| 773 | $CO_2CH_3$ | 2-Cl-phenyl | 1-pyrrolidinocarbonyl |
| 774 | $CO_2CH_3$ | 2-Cl-phenyl | 2-(methylsulfonyl)phenyl |
| 775 | $CO_2CH_3$ | 2-Cl-phenyl | 4-morpholino |
| 776 | $CO_2CH_3$ | 2-Cl-phenyl | 2-(1'-$CF_3$-tetrazol-2-yl)phenyl |
| 777 | $CO_2CH_3$ | 2-Cl-phenyl | 4-morpholinocarbonyl |
| 778 | $CO_2CH_3$ | 2-Cl-phenyl | 2-methyl-1-imidazolyl |
| 779 | $CO_2CH_3$ | 2-Cl-phenyl | 5-methyl-1-imidazolyl |
| 780 | $CO_2CH_3$ | 2-Cl-phenyl | 2-methylsulfonyl-1-imidazolyl |
| 781 | $CO_2CH_3$ | 2-F-phenyl | 2-(aminosulfonyl)phenyl |
| 782 | $CO_2CH_3$ | 2-F-phenyl | 2-(methylaminosulfonyl)phenyl |
| 783 | $CO_2CH_3$ | 2-F-phenyl | 1-pyrrolidinocarbonyl |
| 784 | $CO_2CH_3$ | 2-F-phenyl | 2-(methylsulfonyl)phenyl |
| 785 | $CO_2CH_3$ | 2-F-phenyl | 4-morpholino |
| 786 | $CO_2CH_3$ | 2-F-phenyl | 2-(1'-$CF_3$-tetrazol-2-yl)phenyl |
| 787 | $CO_2CH_3$ | 2-F-phenyl | 4-morpholinocarbonyl |
| 788 | $CO_2CH_3$ | 2-F-phenyl | 2-methyl-1-imidazolyl |
| 789 | $CO_2CH_3$ | 2-F-phenyl | 5-methyl-1-imidazolyl |
| 790 | $CO_2CH_3$ | 2-F-phenyl | 2-methylsulfonyl-1-imidazolyl |
| 791 | $CO_2CH_3$ | 2,6-diF-phenyl | 2-(aminosulfonyl)phenyl |
| 792 | $CO_2CH_3$ | 2,6-diF-phenyl | 2-(methylaminosulfonyl)phenyl |
| 793 | $CO_2CH_3$ | 2,6-diF-phenyl | 1-pyrrolidinocarbonyl |
| 794 | $CO_2CH_3$ | 2,6-diF-phenyl | 2-(methylsulfonyl)phenyl |
| 795 | $CO_2CH_3$ | 2,6-diF-phenyl | 4-morpholino |
| 796 | $CO_2CH_3$ | 2,6-diF-phenyl | 2-(1'-$CF_3$-tetrazol-2-yl)phenyl |
| 797 | $CO_2CH_3$ | 2,6-diF-phenyl | 4-morpholinocarbonyl |
| 798 | $CO_2CH_3$ | 2,6-diF-phenyl | 2-methyl-1-imidazolyl |
| 799 | $CO_2CH_3$ | 2,6-diF-phenyl | 5-methyl-1-imidazolyl |
| 800 | $CO_2CH_3$ | 2,6-diF-phenyl | 2-methylsulfonyl-1-imidazolyl |
| 801 | $CH_2OCH_3$ | phenyl | 2-(aminosulfonyl)phenyl |
| 802 | $CH_2OCH_3$ | phenyl | 2-(methylaminosulfonyl)phenyl |
| 803 | $CH_2OCH_3$ | phenyl | 1-pyrrolidinocarbonyl |
| 804 | $CH_2OCH_3$ | phenyl | 2-(methylsulfonyl)phenyl |
| 805 | $CH_2OCH_3$ | phenyl | 4-morpholino |
| 806 | $CH_2OCH_3$ | phenyl | 2-(1'-$CF_3$-tetrazol-2-yl)phenyl |
| 807 | $CH_2OCH_3$ | phenyl | 4-morpholinocarbonyl |
| 808 | $CH_2OCH_3$ | phenyl | 2-methyl-1-imidazolyl |
| 809 | $CH_2OCH_3$ | phenyl | 5-methyl-1-imidazolyl |
| 810 | $CH_2OCH_3$ | phenyl | 2-methylsulfonyl-1-imidazolyl |
| 811 | $CH_2OCH_3$ | 2-pyridyl | 2-(aminosulfonyl)phenyl |
| 812 | $CH_2OCH_3$ | 2-pyridyl | 2-(methylaminosulfonyl)phenyl |
| 813 | $CH_2OCH_3$ | 2-pyridyl | 1-pyrrolidinocarbonyl |
| 814 | $CH_2OCH_3$ | 2-pyridyl | 2-(methylsulfonyl)phenyl |
| 815 | $CH_2OCH_3$ | 2-pyridyl | 4-morpholino |
| 816 | $CH_2OCH_3$ | 2-pyridyl | 2-(1'-$CF_3$-tetrazol-2-yl)phenyl |
| 817 | $CH_2OCH_3$ | 2-pyridyl | 4-morpholinocarbonyl |
| 818 | $CH_2OCH_3$ | 2-pyridyl | 2-methyl-1-imidazolyl |
| 819 | $CH_2OCH_3$ | 2-pyridyl | 5-methyl-1-imidazolyl |
| 820 | $CH_2OCH_3$ | 2-pyridyl | 2-methylsulfonyl-1-imidazolyl |
| 821 | $CH_2OCH_3$ | 3-pyridyl | 2-(aminosulfonyl)phenyl |
| 822 | $CH_2OCH_3$ | 3-pyridyl | 2-(methylaminosulfonyl)phenyl |

TABLE 1-continued

| | | | |
|---|---|---|---|
| 823 | $CH_2OCH_3$ | 3-pyridyl | 1-pyrrolidinocarbonyl |
| 824 | $CH_2OCH_3$ | 3-pyridyl | 2-(methylsulfonyl)phenyl |
| 825 | $CH_2OCH_3$ | 3-pyridyl | 4-morpholino |
| 826 | $CH_2OCH_3$ | 3-pyridyl | 2-(1'-$CF_3$-tetrazol-2-yl)phenyl |
| 827 | $CH_2OCH_3$ | 3-pyridyl | 4-morpholinocarbonyl |
| 828 | $CH_2OCH_3$ | 3-pyridyl | 2-methyl-1-imidazolyl |
| 829 | $CH_2OCH_3$ | 3-pyridyl | 5-methyl-1-imidazolyl |
| 830 | $CH_2OCH_3$ | 3-pyridyl | 2-methylsulfonyl-1-imidazolyl |
| 831 | $CH_2OCH_3$ | 2-pyrimidyl | 2-(aminosulfonyl)phenyl |
| 832 | $CH_2OCH_3$ | 2-pyrimidyl | 2-(methylaminosulfonyl)phenyl |
| 833 | $CH_2OCH_3$ | 2-pyrimidyl | 1-pyrrolidinocarbonyl |
| 834 | $CH_2OCH_3$ | 2-pyrimidyl | 2-(methylsulfonyl)phenyl |
| 835 | $CH_2OCH_3$ | 2-pyrimidyl | 4-morpholino |
| 836 | $CH_2OCH_3$ | 2-pyrimidyl | 2-(1'-$CF_3$-tetrazol-2-yl)phenyl |
| 837 | $CH_2OCH_3$ | 2-pyrimidyl | 4-morpholinocarbonyl |
| 838 | $CH_2OCH_3$ | 2-pyrimidyl | 2-methyl-1-imidazolyl |
| 839 | $CH_2OCH_3$ | 2-pyrimidyl | 5-methyl-1-imidazolyl |
| 840 | $CH_2OCH_3$ | 2-pyrimidyl | 2-methylsulfonyl-1-imidazolyl |
| 841 | $CH_2OCH_3$ | 5-pyrimidyl | 2-(aminosulfonyl)phenyl |
| 842 | $CH_2OCH_3$ | 5-pyrimidyl | 2-(methylaminosulfonyl)phenyl |
| 843 | $CH_2OCH_3$ | 5-pyrimidyl | 1-pyrrolidinocarbonyl |
| 844 | $CH_2OCH_3$ | 5-pyrimidyl | 2-(methylsulfonyl)phenyl |
| 845 | $CH_2OCH_3$ | 5-pyrimidyl | 4-morpholino |
| 846 | $CH_2OCH_3$ | 5-pyrimidyl | 2-(1'-$CF_3$-tetrazol-2-yl)phenyl |
| 847 | $CH_2OCH_3$ | 5-pyrimidyl | 4-morpholinocarbonyl |
| 848 | $CH_2OCH_3$ | 5-pyrimidyl | 2-methyl-1-imidazolyl |
| 849 | $CH_2OCH_3$ | 5-pyrimidyl | 5-methyl-1-imidazolyl |
| 850 | $CH_2OCH_3$ | 5-pyrimidyl | 2-methylsulfonyl-1-imidazolyl |
| 851 | $CH_2OCH_3$ | 2-Cl-phenyl | 2-(aminosulfonyl)phenyl |
| 852 | $CH_2OCH_3$ | 2-Cl-phenyl | 2-(methylaminosulfonyl)phenyl |
| 853 | $CH_2OCH_3$ | 2-Cl-phenyl | 1-pyrrolidinocarbonyl |
| 854 | $CH_2OCH_3$ | 2-Cl-phenyl | 2-(methylsulfonyl)phenyl |
| 855 | $CH_2OCH_3$ | 2-Cl-phenyl | 4-morpholino |
| 856 | $CH_2OCH_3$ | 2-Cl-phenyl | 2-(1'-$CF_3$-tetrazol-2-yl)phenyl |
| 857 | $CH_2OCH_3$ | 2-Cl-phenyl | 4-morpholinocarbonyl |
| 858 | $CH_2OCH_3$ | 2-Cl-phenyl | 2-methyl-1-imidazolyl |
| 859 | $CH_2OCH_3$ | 2-Cl-phenyl | 5-methyl-1-imidazolyl |
| 860 | $CH_2OCH_3$ | 2-Cl-phenyl | 2-methylsulfonyl-1-imidazolyl |
| 861 | $CH_2OCH_3$ | 2-F-phenyl | 2-(aminosulfonyl)phenyl |
| 862 | $CH_2OCH_3$ | 2-F-phenyl | 2-(methylaminosulfonyl)phenyl |
| 863 | $CH_2OCH_3$ | 2-F-phenyl | 1-pyrrolidinocarbonyl |
| 864 | $CH_2OCH_3$ | 2-F-phenyl | 2-(methylsulfonyl)phenyl |
| 865 | $CH_2OCH_3$ | 2-F-phenyl | 4-morpholino |
| 866 | $CH_2OCH_3$ | 2-F-phenyl | 2-(1'-$CF_3$-tetrazol-2-yl)phenyl |
| 867 | $CH_2OCH_3$ | 2-F-phenyl | 4-morpholinocarbonyl |
| 868 | $CH_2OCH_3$ | 2-F-phenyl | 2-methyl-1-imidazolyl |
| 869 | $CH_2OCH_3$ | 2-F-phenyl | 5-methyl-1-imidazolyl |
| 870 | $CH_2OCH_3$ | 2-F-phenyl | 2-methylsulfonyl-1-imidazolyl |
| 871 | $CH_2OCH_3$ | 2,6-diF-phenyl | 2-(aminosulfonyl)phenyl |
| 872 | $CH_2OCH_3$ | 2,6-diF-phenyl | 2-(methylaminosulfonyl)phenyl |
| 873 | $CH_2OCH_3$ | 2,6-diF-phenyl | 1-pyrrolidinocarbonyl |
| 874 | $CH_2OCH_3$ | 2,6-diF-phenyl | 2-(methylsulfonyl)phenyl |
| 875 | $CH_2OCH_3$ | 2,6-diF-phenyl | 4-morpholino |
| 876 | $CH_2OCH_3$ | 2,6-diF-phenyl | 2-(1'-$CF_3$-tetrazol-2-yl)phenyl |
| 877 | $CH_2OCH_3$ | 2,6-diF-phenyl | 4-morpholinocarbonyl |
| 878 | $CH_2OCH_3$ | 2,6-diF-phenyl | 2-methyl-1-imidazolyl |
| 879 | $CH_2OCH_3$ | 2,6-diF-phenyl | 5-methyl-1-imidazolyl |
| 880 | $CH_2OCH_3$ | 2,6-diF-phenyl | 2-methylsulfonyl-1-imidazolyl |
| 881 | $CONH_2$ | phenyl | 2-(aminosulfonyl)phenyl |
| 882 | $CONH_2$ | phenyl | 2-(methylaminosulfonyl)phenyl |
| 883 | $CONH_2$ | phenyl | 1-pyrrolidinocarbonyl |
| 884 | $CONH_2$ | phenyl | 2-(methylsulfonyl)phenyl |
| 885 | $CONH_2$ | phenyl | 4-morpholino |
| 886 | $CONH_2$ | phenyl | 2-(1'-$CF_3$-tetrazol-2-yl)phenyl |
| 887 | $CONH_2$ | phenyl | 4-morpholinocarbonyl |
| 888 | $CONH_2$ | phenyl | 2-methyl-1-imidazolyl |
| 889 | $CONH_2$ | phenyl | 5-methyl-1-imidazolyl |
| 890 | $CONH_2$ | phenyl | 2-methylsulfonyl-1-imidazolyl |
| 891 | $CONH_2$ | 2-pyridyl | 2-(aminosulfonyl)phenyl |
| 892 | $CONH_2$ | 2-pyridyl | 2-(methylaminosulfonyl)phenyl |
| 893 | $CONH_2$ | 2-pyridyl | 1-pyrrolidinocarbonyl |
| 894 | $CONH_2$ | 2-pyridyl | 2-(methylsulfonyl)phenyl |
| 895 | $CONH_2$ | 2-pyridyl | 4-morpholino |
| 896 | $CONH_2$ | 2-pyridyl | 2-(1'-$CF_3$-tetrazol-2-yl)phenyl |
| 897 | $CONH_2$ | 2-pyridyl | 4-morpholinocarbonyl |
| 898 | $CONH_2$ | 2-pyridyl | 2-methyl-1-imidazolyl |
| 899 | $CONH_2$ | 2-pyridyl | 5-methyl-1-imidazolyl |
| 900 | $CONH_2$ | 2-pyridyl | 2-methylsulfonyl-1-imidazolyl |
| 901 | $CONH_2$ | 3-pyridyl | 2-(aminosulfonyl)phenyl |

TABLE 1-continued

| | | | |
|---|---|---|---|
| 902 | CONH$_2$ | 3-pyridyl | 2-(methylaminosulfonyl)phenyl |
| 903 | CONH$_2$ | 3-pyridyl | 1-pyrrolidinocarbonyl |
| 904 | CONH$_2$ | 3-pyridyl | 2-(methylsulfonyl)phenyl |
| 905 | CONH$_2$ | 3-pyridyl | 4-morpholino |
| 906 | CONH$_2$ | 3-pyridyl | 2-(1'-CF$_3$-tetrazol-2-yl)phenyl |
| 907 | CONH$_2$ | 3-pyridyl | 4-morpholinocarbonyl |
| 908 | CONH$_2$ | 3-pyridyl | 2-methyl-1-imidazolyl |
| 909 | CONH$_2$ | 3-pyridyl | 5-methyl-1-imidazolyl |
| 910 | CONH$_2$ | 3-pyridyl | 2-methylsulfonyl-1-imidazolyl |
| 911 | CONH$_2$ | 2-pyrimidyl | 2-(aminosulfonyl)phenyl |
| 912 | CONH$_2$ | 2-pyrimidyl | 2-(methylaminosulfonyl)phenyl |
| 913 | CONH$_2$ | 2-pyrimidyl | 1-pyrrolidinocarbonyl |
| 914 | CONH$_2$ | 2-pyrimidyl | 2-(methylsulfonyl)phenyl |
| 915 | CONH$_2$ | 2-pyrimidyl | 4-morpholino |
| 916 | CONH$_2$ | 2-pyrimidyl | 2-(1'-CF$_3$-tetrazol-2-yl)phenyl |
| 917 | CONH$_2$ | 2-pyrimidyl | 4-morpholinocarbonyl |
| 918 | CONH$_2$ | 2-pyrimidyl | 2-methyl-1-imidazolyl |
| 919 | CONH$_2$ | 2-pyrimidyl | 5-methyl-1-imidazolyl |
| 920 | CONH$_2$ | 2-pyrimidyl | 2-methylsulfonyl-1-imidazolyl |
| 921 | CONH$_2$ | 5-pyrimidyl | 2-(aminosulfonyl)phenyl |
| 922 | CONH$_2$ | 5-pyrimidyl | 2-(methylaminosulfonyl)phenyl |
| 923 | CONH$_2$ | 5-pyrimidyl | 1-pyrrolidinocarbonyl |
| 924 | CONH$_2$ | 5-pyrimidyl | 2-(methylsulfonyl)phenyl |
| 925 | CONH$_2$ | 5-pyrimidyl | 4-morpholino |
| 926 | CONH$_2$ | 5-pyrimidyl | 2-(1'-CF$_3$-tetrazol-2-yl)phenyl |
| 927 | CONH$_2$ | 5-pyrimidyl | 4-morpholinocarbonyl |
| 928 | CONH$_2$ | 5-pyrimidyl | 2-methyl-1-imidazolyl |
| 929 | CONH$_2$ | 5-pyrimidyl | 5-methyl-1-imidazolyl |
| 930 | CONH$_2$ | 5-pyrimidyl | 2-methylsulfonyl-1-imidazolyl |
| 931 | CONH$_2$ | 2-Cl-phenyl | 2-(aminosulfonyl)phenyl |
| 932 | CONH$_2$ | 2-Cl-phenyl | 2-(methylaminosulfonyl)phenyl |
| 933 | CONH$_2$ | 2-Cl-phenyl | 1-pyrrolidinocarbonyl |
| 934 | CONH$_2$ | 2-Cl-phenyl | 2-(methylsulfonyl)phenyl |
| 935 | CONH$_2$ | 2-Cl-phenyl | 4-morpholino |
| 936 | CONH$_2$ | 2-Cl-phenyl | 2-(1'-CF$_3$-tetrazol-2-yl)phenyl |
| 937 | CONH$_2$ | 2-Cl-phenyl | 4-morpholinocarbonyl |
| 938 | CONH$_2$ | 2-Cl-phenyl | 2-methyl-1-imidazolyl |
| 939 | CONH$_2$ | 2-Cl-phenyl | 5-methyl-1-imidazolyl |
| 940 | CONH$_2$ | 2-Cl-phenyl | 2-methylsulfonyl-1-imidazolyl |
| 941 | CONH$_2$ | 2-F-phenyl | 2-(aminosulfonyl)phenyl |
| 942 | CONH$_2$ | 2-F-phenyl | 2-(methylaminosulfonyl)phenyl |
| 943 | CONH$_2$ | 2-F-phenyl | 1-pyrrolidinocarbonyl |
| 944 | CONH$_2$ | 2-F-phenyl | 2-(methylsulfonyl)phenyl |
| 945 | CONH$_2$ | 2-F-phenyl | 4-morpholino |
| 946 | CONH$_2$ | 2-F-phenyl | 2-(1'-CF$_3$-tetrazol-2-yl)phenyl |
| 947 | CONH$_2$ | 2-F-phenyl | 4-morpholinocarbonyl |
| 948 | CONH$_2$ | 2-F-phenyl | 2-methyl-1-imidazolyl |
| 949 | CONH$_2$ | 2-F-phenyl | 5-methyl-1-imidazolyl |
| 950 | CONH$_2$ | 2-F-phenyl | 2-methylsulfonyl-1-imidazolyl |
| 951 | CONH$_2$ | 2,6-diF-phenyl | 2-(aminosulfonyl)phenyl |
| 952 | CONH$_2$ | 2,6-diF-phenyl | 2-(methylaminosulfonyl)phenyl |
| 953 | CONH$_2$ | 2,6-diF-phenyl | 1-pyrrolidinocarbonyl |
| 954 | CONH$_2$ | 2,6-diF-phenyl | 2-(methylsulfonyl)phenyl |
| 955 | CONH$_2$ | 2,6-diF-phenyl | 4-morpholino |
| 956 | CONH$_2$ | 2,6-diF-phenyl | 2-(1'-CF$_3$-tetrazol-2-yl)phenyl |
| 957 | CONH$_2$ | 2,6-diF-phenyl | 4-morpholinocarbonyl |
| 958 | CONH$_2$ | 2,6-diF-phenyl | 2-methyl-1-imidazolyl |
| 959 | CONH$_2$ | 2,6-diF-phenyl | 5-methyl-1-imidazolyl |
| 960 | CONH$_2$ | 2,6-diF-phenyl | 2-methylsulfonyl-1-imidazolyl |

TABLE 2

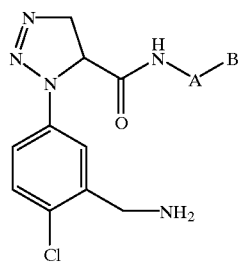

a

TABLE 2-continued

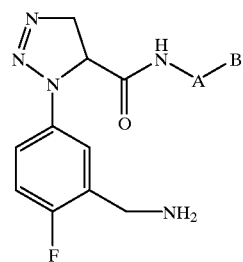

b

TABLE 2-continued
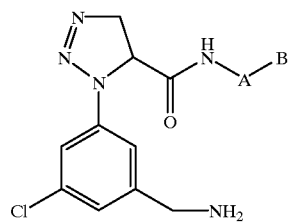 c
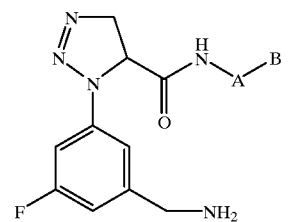 d
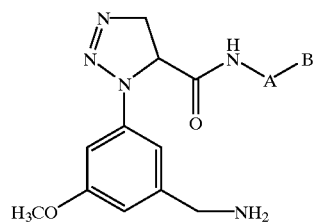 e
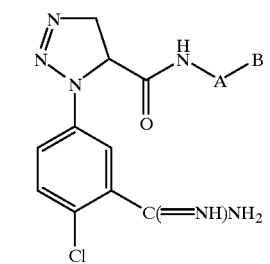 f
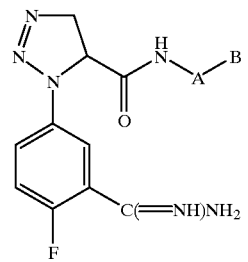 g
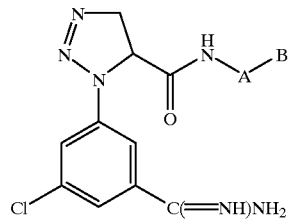 h
TABLE 2-continued
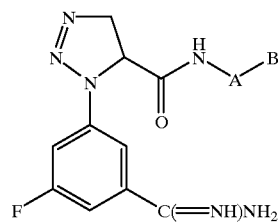 i
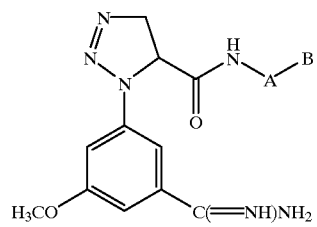 j
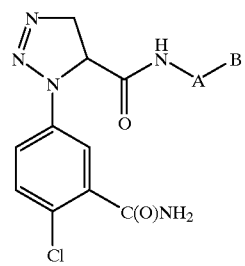 k
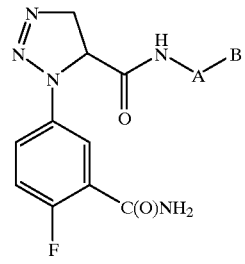 l
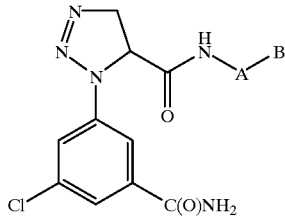 m
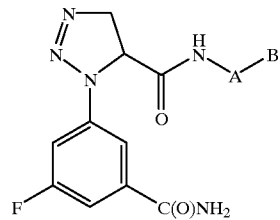 n TABLE 2-continued
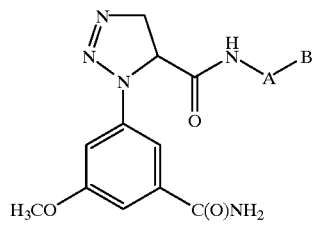 o
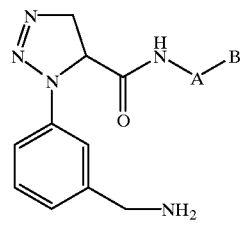 p
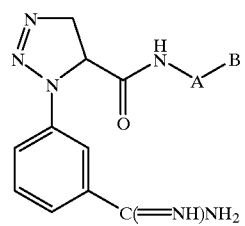 q
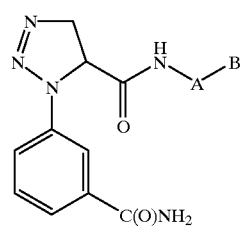 r
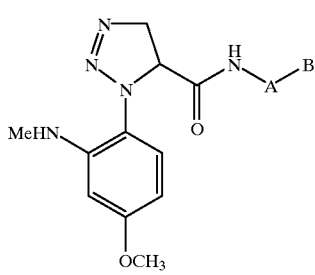 s
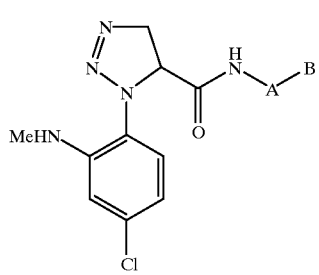 t
TABLE 2-continued
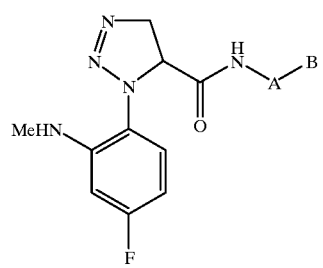 u
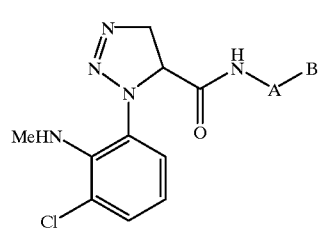 v
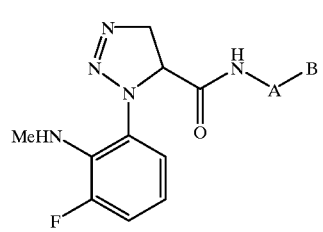 w
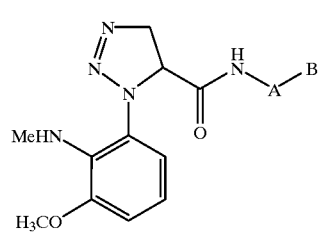 x
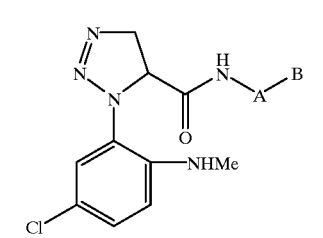 y
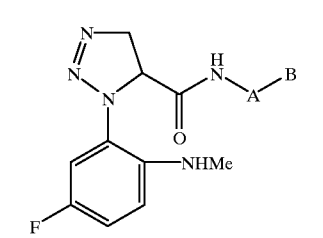 z TABLE 2-continued
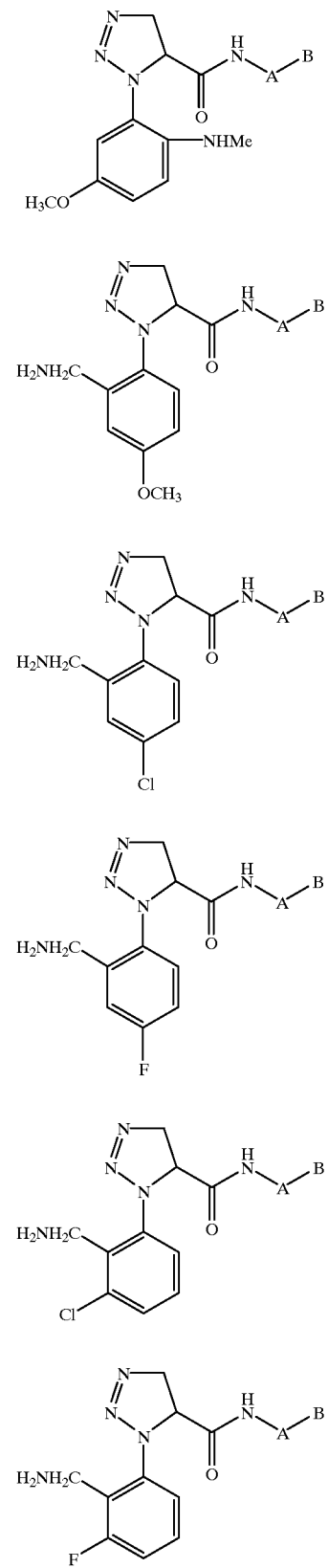
TABLE 2-continued
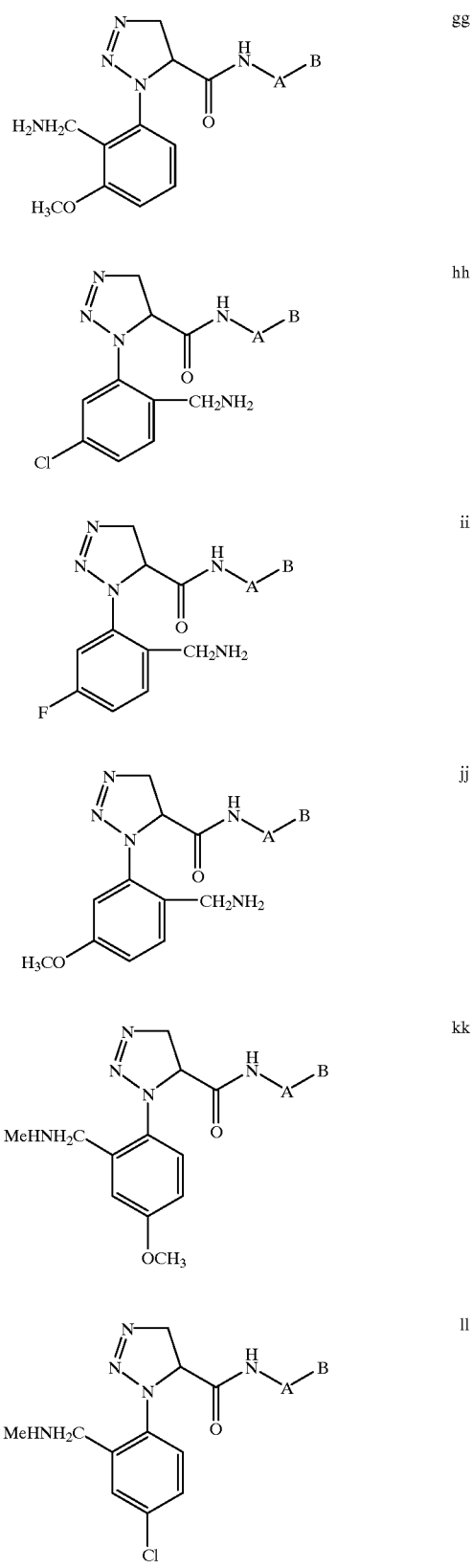

TABLE 2-continued

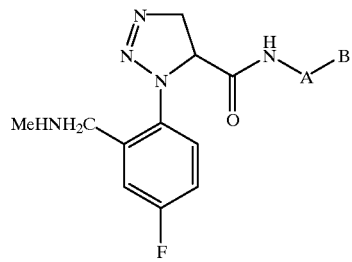
mm

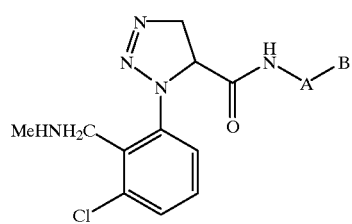
nn

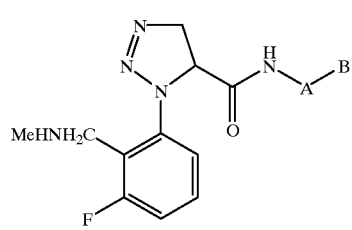
oo

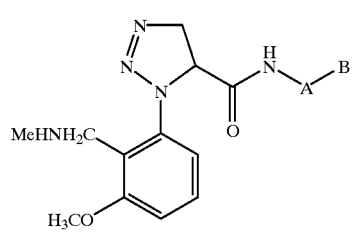
pp

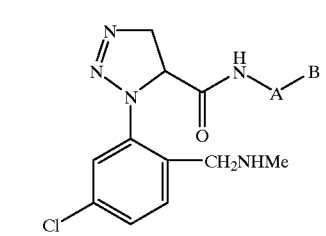
qq

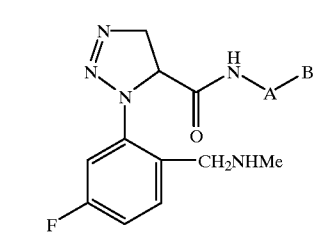
rr

TABLE 2-continued

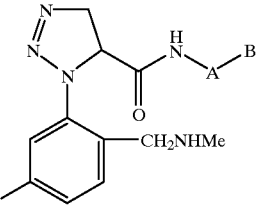
ss

| Ex # | A | B |
|---|---|---|
| 1 | phenyl | 2-(aminosulfonyl)phenyl |
| 2 | phenyl | 2-(methylaminosulfonyl)phenyl |
| 3 | phenyl | 1-pyrrolidinocarbonyl |
| 4 | phenyl | 2-(methylsulfonyl)phenyl |
| 5 | phenyl | 4-morpholino |
| 6 | phenyl | 2-(1'-CF$_3$-tetrazol-2-yl)phenyl |
| 7 | phenyl | 4-morpholinocarbonyl |
| 8 | phenyl | 2-methyl-1-imidazolyl |
| 9 | phenyl | 5-methyl-1-imidazolyl |
| 10 | phenyl | 2-methylsulfonyl-1-imidazolyl |
| 11 | 2-pyridyl | 2-(aminosulfonyl)phenyl |
| 12 | 2-pyridyl | 2-(methylaminosulfonyl)phenyl |
| 13 | 2-pyridyl | 1-pyrrolidinocarbonyl |
| 14 | 2-pyridyl | 2-(methylsulfonyl)phenyl |
| 15 | 2-pyridyl | 4-morpholino |
| 16 | 2-pyridyl | 2-(1'-CF$_3$-tetrazol-2-yl)phenyl |
| 17 | 2-pyridyl | 4-morpholinocarbonyl |
| 18 | 2-pyridyl | 2-methyl-1-imidazolyl |
| 19 | 2-pyridyl | 5-methyl-1-imidazolyl |
| 20 | 2-pyridyl | 2-methylsulfonyl-1-imidazolyl |
| 21 | 3-pyridyl | 2-(aminosulfonyl)phenyl |
| 22 | 3-pyridyl | 2-(methylaminosulfonyl)phenyl |
| 23 | 3-pyridyl | 1-pyrrolidinocarbonyl |
| 24 | 3-pyridyl | 2-(methylsulfonyl)phenyl |
| 25 | 3-pyridyl | 4-morpholino |
| 26 | 3-pyridyl | 2-(1'-CF$_3$-tetrazol-2-yl)phenyl |
| 27 | 3-pyridyl | 4-morpholinocarbonyl |
| 28 | 3-pyridyl | 2-methyl-1-imidazolyl |
| 29 | 3-pyridyl | 5-methyl-1-imidazolyl |
| 30 | 3-pyridyl | 2-methylsulfonyl-1-imidazolyl |
| 31 | 2-pyrimidyl | 2-(aminosulfonyl)phenyl |
| 32 | 2-pyrimidyl | 2-(methylaminosulfonyl)phenyl |
| 33 | 2-pyrimidyl | 1-pyrrolidinocarbonyl |
| 34 | 2-pyrimidyl | 2-(methylsulfonyl)phenyl |
| 35 | 2-pyrimidyl | 4-morpholino |
| 36 | 2-pyrimidyl | 2-(1'-CF$_3$-tetrazol-2-yl)phenyl |
| 37 | 2-pyrimidyl | 4-morpholinocarbonyl |
| 38 | 2-pyrimidyl | 2-methyl-1-imidazolyl |
| 39 | 2-pyrimidyl | 5-methyl-1-imidazolyl |
| 40 | 2-pyrimidyl | 2-methylsulfonyl-1-imidazolyl |
| 41 | 5-pyrimidyl | 2-(aminosulfonyl)phenyl |
| 42 | 5-pyrimidyl | 2-(methylaminosulfonyl)phenyl |
| 43 | 5-pyrimidyl | 1-pyrrolidinocarbonyl |
| 44 | 5-pyrimidyl | 2-(methylsulfonyl)phenyl |
| 45 | 5-pyrimidyl | 4-morpholino |
| 46 | 5-pyrimidyl | 2-(1'-CF$_3$-tetrazol-2-yl)phenyl |
| 47 | 5-pyrimidyl | 4-morpholinocarbonyl |
| 48 | 5-pyrimidyl | 2-methyl-1-imidazolyl |
| 49 | 5-pyrimidyl | 5-methyl-1-imidazolyl |
| 50 | 5-pyrimidyl | 2-methylsulfonyl-1-imidazolyl |
| 51 | 2-Cl-phenyl | 2-(aminosulfonyl)phenyl |
| 52 | 2-Cl-phenyl | 2-(methylaminosulfonyl)phenyl |
| 53 | 2-Cl-phenyl | 1-pyrrolidinocarbonyl |
| 54 | 2-Cl-phenyl | 2-(methylsulfonyl)phenyl |
| 55 | 2-Cl-phenyl | 4-morpholino |
| 56 | 2-Cl-phenyl | 2-(1'-CF$_3$-tetrazol-2-yl)phenyl |
| 57 | 2-Cl-phenyl | 4-morpholinocarbonyl |
| 58 | 2-Cl-phenyl | 2-methyl-1-imidazolyl |
| 59 | 2-Cl-phenyl | 5-methyl-1-imidazolyl |
| 60 | 2-Cl-phenyl | 2-methylsulfonyl-1-imidazolyl |
| 61 | 2-F-phenyl | 2-(aminosulfonyl)phenyl |
| 62 | 2-F-phenyl | 2-(methylaminosulfonyl)phenyl |
| 63 | 2-F-phenyl | 1-pyrrolidinocarbonyl |
| 64 | 2-F-phenyl | 2-(methylsulfonyl)phenyl |
| 65 | 2-F-phenyl | 4-morpholino |

TABLE 2-continued

| 66 | 2-F-phenyl | 2-(1'-CF$_3$-tetrazol-2-yl)phenyl |
| 67 | 2-F-phenyl | 4-morpholinocarbonyl |
| 68 | 2-F-phenyl | 2-methyl-1-imidazolyl |
| 69 | 2-F-phenyl | 5-methyl-1-imidazolyl |
| 70 | 2-F-phenyl | 2-methylsulfonyl-1-imidazolyl |
| 71 | 2,6-diF-phenyl | 2-(aminosulfonyl)phenyl |
| 72 | 2,6-diF-phenyl | 2-(methylaminosulfonyl)phenyl |
| 73 | 2,6-diF-phenyl | 1-pyrrolidinocarbonyl |
| 74 | 2,6-diF-phenyl | 2-(methylsulfonyl)phenyl |
| 75 | 2,6-diF-phenyl | 4-morpholino |
| 76 | 2,6-diF-phenyl | 2-(1'-CF$_3$-tetrazol-2-yl)phenyl |
| 77 | 2,6-diF-phenyl | 4-morpholinocarbonyl |
| 78 | 2,6-diF-phenyl | 2-methyl-1-imidazolyl |
| 79 | 2,6-diF-phenyl | 5-methyl-1-imidazolyl |
| 80 | 2,6-diF-phenyl | 2-methylsulfonyl-1-imidazolyl |

UTILITY

The compounds of this invention are useful as anticoagulants for the treatment or prevention of thromboembolic disorders in mammals. The term "thromboembolic disorders" as used herein includes arterial or venous cardiovascular or cerebrovascular thromboembolic disorders, including, for example, unstable angina, first or recurrent myocardial infarction, ischemic sudden death, transient ischemic attack, stroke, atherosclerosis, venous thrombosis, deep vein thrombosis, thrombophlebitis, arterial embolism, coronary and cerebral arterial thrombosis, cerebral embolism, kidney embolisms, and pulmonary embolisms. The anticoagulant effect of compounds of the present invention is believed to be due to inhibition of factor Xa or thrombin.

The effectiveness of compounds of the present invention as inhibitors of factor Xa was determined using purified human factor Xa and synthetic substrate. The rate of factor Xa hydrolysis of chromogenic substrate S2222 (Kabi Pharmacia, Franklin, Ohio) was measured both in the absence and presence of compounds of the present invention. Hydrolysis of the substrate resulted in the release of pNA, which was monitored spectrophotometrically by measuring the increase in absorbance at 405 nM. A decrease in the rate of absorbance change at 405 nm in the presence of inhibitor is indicative of enzyme inhibition. The results of this assay are expressed as inhibitory constant, $K_i$.

Factor Xa determinations were made in 0.10 M sodium phosphate buffer, pH 7.5, containing 0.20 M NaCl, and 0.5% PEG 8000. The Michaelis constant, $K_m$, for substrate hydrolysis was determined at 25° C. using the method of Lineweaver and Burk. Values of $K_i$ were determined by allowing 0.2–0.5 nM human factor Xa (Enzyme Research Laboratories, South Bend, Ind.) to react with the substrate (0.20 mM–1 mM) in the presence of inhibitor. Reactions were allowed to go for 30 minutes and the velocities (rate of absorbance change vs time) were measured in the time frame of 25–30 minutes. The following relationship was used to calculate $K_i$ values:

$$(v_o 31\ v_s)/v_s = I/(K_i(1+S/K_m))$$

where:
  $v_o$ is the velocity of the control in the absence of inhibitor;
  $v_s$ is the velocity in the presence of inhibitor;
  I is the concentration of inhibitor;
  $K_i$ is the dissociation constant of the enzyme:inhibitor complex;
  S is the concentration of substrate;
  $K_m$ is the Michaelis constant.

Using the methodology described above, a compound of the present invention were found to exhibit a $K_i$ of $\leq 10\ \mu M$, thereby confirming the utility of the compounds of the present invention as effective Xa inhibitors.

The antithrombotic effect of compounds of the present invention can be demonstrated in a rabbit arterio-venous (AV) shunt thrombosis model. In this model, rabbits weighing 2–3 kg anesthetized with a mixture of xylazine (10 mg/kg i.m.) and ketamine (50 mg/kg i.m.) are used. A saline-filled AV shunt device is connected between the femoral arterial and the femoral venous cannulae. The AV shunt device consists of a piece of 6-cm tygon tubing which contains a piece of silk thread. Blood will flow from the femoral artery via the AV-shunt into the femoral vein. The exposure of flowing blood to a silk thread will induce the formation of a significant thrombus. After forty minutes, the shunt is disconnected and the silk thread covered with thrombus is weighed. Test agents or vehicle will be given (i.v., i.p., s.c., or orally) prior to the opening of the AV shunt. The percentage inhibition of thrombus formation is determined for each treatment group. The ID50 values (dose which produces 50% inhibition of thrombus formation) are estimated by linear regression.

The compounds of formula (I) may also be useful as inhibitors of serine proteases, notably human thrombin, plasma kallikrein and plasmin. Because of their inhibitory action, these compounds are indicated for use in the prevention or treatment of physiological reactions, blood coagulation and inflammation, catalyzed by the aforesaid class of enzymes. Specifically, the compounds have utility as drugs for the treatment of diseases arising from elevated thrombin activity such as myocardial infarction, and as reagents used as anticoagulants in the processing of blood to plasma for diagnostic and other commercial purposes.

Some compounds of the present invention were shown to be direct acting inhibitors of the serine protease thrombin by their ability to inhibit the cleavage of small molecule substrates by thrombin in a purified system. In vitro inhibition constants were determined by the method described by Kettner et al. in *J. Biol. Chem.* 265, 18289–18297 (1990), herein incorporated by reference. In these assays, thrombin-mediated hydrolysis of the chromogenic substrate S2238 (Helena Laboratories, Beaumont, Tex.) was monitored spectrophotometrically. Addition of an inhibitor to the assay mixture results in decreased absorbance and is indicative of thrombin inhibition. Human thrombin (Enzyme Research Laboratories, Inc., South Bend, Ind.) at a concentration of 0.2 nM in 0.10 M sodium phosphate buffer, pH 7.5, 0.20 M NaCl, and 0.5% PEG 6000, was incubated with various substrate concentrations ranging from 0.20 to 0.02 mM. After 25 to 30 minutes of incubation, thrombin activity was assayed by monitoring the rate of increase in absorbance at 405 nm which arises owing to substrate hydrolysis. Inhibition constants were derived from reciprocal plots of the reaction velocity as a function of substrate concentration using the standard method of Lineweaver and Burk. Using the methodology described above, some compounds of this invention were evaluated and found to exhibit a $K_i$ of less than 10 μm, thereby confirming the utility of the compounds of the present invention as effective thrombin inhibitors.

The compounds of the present invention can be administered alone or in combination with one or more additional therapeutic agents. These include other anti-coagulant or coagulation inhibitory agents, anti-platelet or platelet inhibitory agents, thrombin inhibitors, or thrombolytic or fibrinolytic agents.

The compounds are administered to a mammal in a therapeutically effective amount. By "therapeutically effective amount" it is meant an amount of a compound of Formula I that, when administered alone or in combination with an additional therapeutic agent to a mammal, is effective to prevent or ameliorate the thromboembolic disease condition or the progression of the disease.

By "administered in combination" or "combination therapy" it is meant that the compound of Formula I and one or more additional therapeutic agents are administered concurrently to the mammal being treated. When administered in combination each component may be administered at the same time or sequentially in any order at different points in time. Thus, each component may be administered separately but sufficiently closely in time so as to provide the desired therapeutic effect. Other anticoagulant agents (or coagulation inhibitory agents) that may be used in combination with the compounds of this invention include warfarin and heparin, as well as other factor Xa inhibitors such as those described in the publications identified above under Background of the Invention.

The term anti-platelet agents (or platelet inhibitory agents), as used herein, denotes agents that inhibit platelet function such as by inhibiting the aggregation, adhesion or granular secretion of platelets. Such agents include, but are not limited to, the various known non-steroidal anti-inflammatory drugs (NSAIDS) such as aspirin, ibuprofen, naproxen, sulindac, indomethacin, mefenamate, droxicam, diclofenac, sulfinpyrazone, and piroxicam, including pharmaceutically acceptable salts or prodrugs thereof. Of the NSAIDS, aspirin (acetylsalicyclic acid or ASA), and piroxicam are preferred. Other suitable anti-platelet agents include ticlopidine, including pharmaceutically acceptable salts or prodrugs thereof. Ticlopidine is also a preferred compound since it is known to be gentle on the gastro-intestinal tract in use. Still other suitable platelet inhibitory agents include IIb/IIIa antagonists, thromboxane-A2-receptor antagonists and thromboxane-A2-synthetase inhibitors, as well as pharmaceutically acceptable salts or prodrugs thereof.

The term thrombin inhibitors (or anti-thrombin agents), as used herein, denotes inhibitors of the serine protease thrombin. By inhibiting thrombin, various thrombin-mediated processes, such as thrombin-mediated platelet activation (that is, for example, the aggregation of platelets, and/or the granular secretion of plasminogen activator inhibitor-1 and/or serotonin) and/or fibrin formation are disrupted. A number of thrombin inhibitors are known to one of skill in the art and these inhibitors are contemplated to be used in combination with the present compounds. Such inhibitors include, but are not limited to, boroarginine derivatives, boropeptides, heparins, hirudin and argatroban, including pharmaceutically acceptable salts and prodrugs thereof. Boroarginine derivatives and boropeptides include N-acetyl and peptide derivatives of boronic acid, such as C-terminal a-aminoboronic acid derivatives of lysine, ornithine, arginine, homoarginine and corresponding isothiouronium analogs thereof. The term hirudin, as used herein, includes suitable derivatives or analogs of hirudin, referred to herein as hirulogs, such as disulfatohirudin. Boropeptide thrombin inhibitors include compounds described in Kettner et al., U.S. Pat. No. 5,187,157 and European Patent Application Publication Number 293 881 A2, the disclosures of which are hereby incorporated herein by reference. Other suitable boroarginine derivatives and boropeptide thrombin inhibitors include those disclosed in PCT Application Publication Number 92/07869 and European Patent Application Publication Number 471,651 A2, the disclosures of which are hereby incorporated herein by reference.

The term thrombolytics (or fibrinolytic) agents (or thrombolytics or fibrinolytics), as used herein, denotes agents that lyse blood clots (thrombi). Such agents include tissue plasminogen activator, anistreplase, urokinase or streptokinase, including pharmaceutically acceptable salts or prodrugs thereof. The term anistreplase, as used herein, refers to anisoylated plasminogen streptokinase activator complex, as described, for example, in European Patent Application No. 028,489, the disclosure of which is hereby incorporated herein by reference herein. The term urokinase, as used herein, is intended to denote both dual and single chain urokinase, the latter also being referred to herein as prourokinase.

Administration of the compounds of Formula I of the invention in combination with such additional therapeutic agent, may afford an efficacy advantage over the compounds and agents alone, and may do so while permitting the use of lower doses of each. A lower dosage minimizes the potential of side effects, thereby providing an increased margin of safety.

The compounds of the present invention are also useful as standard or reference compounds, for example as a quality standard or control, in tests or assays involving the inhibition of factor Xa. Such compounds may be provided in a commercial kit, for example, for use in pharmaceutical research involving factor Xa. For example, a compound of the present invention could be used as a reference in an assay to compare its known activity to a compound with an unknown activity. This would ensure the experimenter that the assay was being performed properly and provide a basis for comparison, especially if the test compound was a derivative of the reference compound. When developing new assays or protocols, compounds according to the present invention could be used to test their effectiveness.

The compounds of the present invention may also be used in diagnostic assays involving factor Xa. For example, the presence of factor Xa in an unknown sample could be determined by addition of chromogenic substrate S2222 to a series of solutions containing test sample and optionally one of the compounds of the present invention. If production of pNA is observed in the solutions containing test sample, but not in the presence of a compound of the present invention, then one would conclude factor Xa was present.

Dosage and Formulation

The compounds of this invention can be administered in such oral dosage forms as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, or intramuscular form, all using dosage forms well known to those of ordinary skill in the pharmaceutical arts. They can be administered alone, but generally will be administered with a pharmaceutical carrier selected on the basis of the chosen route of administration and standard pharmaceutical practice.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient,and the effect desired. A physician or veterinarian can determine and prescribe the effective amount of the drug required to prevent, counter, or arrest the progress of the thromboembolic disorder.

By way of general guidance, the daily oral dosage of each active ingredient, when used for the indicated effects, will range between about 0.001 to 1000 mg/kg of body weight, preferably between about 0.01 to 100 mg/kg of body weight per day, and most preferably between about 1.0 to 20 mg/kg/day. Intravenously, the most preferred doses will range from about 1 to about 10 mg/kg/minute during a constant rate infusion. Compounds of this invention may be administered in a single daily dose, or the total daily dosage may be administered in divided doses of two, three, or four times daily.

Compounds of this invention can be administered in intranasal form via topical use of suitable intranasal vehicles, or via transdermal routes, using transdermal skin patches. When administered in the form of a transdermal delivery system, the dosage administration will, of course, be continuous rather than intermittent throughout the dosage regimen.

The compounds are typically administered in admixture with suitable pharmaceutical diluents, excipients, or carriers (collectively referred to herein as pharmaceutical carriers) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl callulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Dosage forms (pharmaceutical compositions) suitable for administration may contain from about 1 milligram to about 100 milligrams of active ingredient per dosage unit. In these pharmaceutical compositions the active ingredient will ordinarily be present in an amount of about 0.5–95% by weight based on the total weight of the composition.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in *Reminaton's Pharmaceutical Sciences*, Mack Publishing Company, a standard reference text in this field.

Representative useful pharmaceutical dosage-forms for administration of the compounds of this invention can be illustrated as follows:

Capsules

A large number of unit capsules can be prepared by filling standard two-piece hard gelatin capsules each with 100 milligrams of powdered active ingredient, 150 milligrams of lactose, 50 milligrams of cellulose, and 6 milligrams magnesium stearate.

Soft Gelatin Capsules

A mixture of active ingredient in a digestable oil such as soybean oil, cottonseed oil or olive oil may be prepared and injected by means of a positive displacement pump into gelatin to form soft gelatin capsules containing 100 milligrams of the active ingredient. The capsules should be washed and dried.

Tablets

Tablets may be prepared by conventional procedures so that the dosage unit is 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

Injectable

A parenteral composition suitable for administration by injection may be prepared by stirring 1.5% by weight of active ingredient in 10% by volume propylene glycol and water. The solution should be made isotonic with sodium chloride and sterilized.

Suspension

An aqueous suspension can be prepared for oral administration so that each 5 mL contain 100 mg of finely divided active ingredient, 200 mg of sodium carboxymethyl cellulose, 5 mg of sodium benzoate, 1.0 g of sorbitol solution, U.S.P., and 0.025 mL of vanillin.

Where the compounds of this invention are combined with other anticoagulant agents, for example, a daily dosage may be about 0.1 to 100 milligrams of the compound of Formula I and about 1 to 7.5 milligrams of the second anticoagulant, per kilogram of patient body weight. For a tablet dosage form, the compounds of this invention generally may be present in an amount of about 5 to 10 milligrams per dosage unit, and the second anti-coagulant in an amount of about 1 to 5 milligrams per dosage unit.

Where the compounds of Formula I are administered in combination with an anti-platelet agent, by way of general guidance, typically a daily dosage may be about 0.01 to 25 milligrams of the compound of Formula I and about 50 to 150 milligrams of the anti-platelet agent, preferably about 0.1 to 1 milligrams of the compound of Formula I and about 1 to 3 milligrams of antiplatelet agents, per kilogram of patient body weight.

Where the compounds of Formula I are adminstered in combination with thrombolytic agent, typically a daily dosage may be about 0.1 to 1 milligrams of the compound of Formula I, per kilogram of patient body weight and, in the case of the thrombolytic agents, the usual dosage of the thrombolyic agent when administered alone may be reduced by about 70–80% when administered with a compound of Formula I.

Where two or more of the foregoing second therapeutic agents are administered with the compound of Formula I, generally the amount of each component in a typical daily dosage and typical dosage form may be reduced relative to the usual dosage of the agent when administered alone, in view of the additive or synergistic effect of the therapeutic agents when administered in combination.

Particularly when provided as a single dosage unit, the potential exists for a chemical interaction between the combined active ingredients. For this reason, when the compound of Formula I and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material which effects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a lowviscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

Obviously, numerous modifications and variations of the present invention are possible in light of the above teachings. It is therefore to be understood that within the scope of the appended claims, the invention may be practiced otherwise that as specifically described herein.

What is claimed is:

1. A compound of formula I:

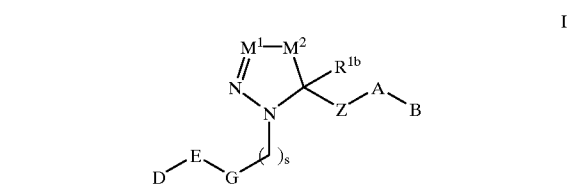

89

-continued

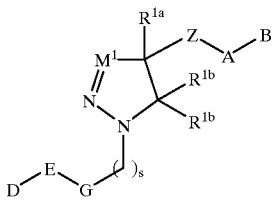

II or a steroisomer or pharmaceutically acceptable salt thereof, wherein;

$M^1$ is $CR^{1c}$;

$M^2$ is $CR^{1a}R^{1a}$;

D is selected from $C(=NR^8)NR^7R^9$, $NHC(=NR^8)NR^7R^9$, $NR^8CH(=NR^7)$, $C(O)NR^7R^8$, and $CR^8R^9NR^7R^8$;

E is selected from phenyl, pyridyl, pyrimidyl, pyrazinyl, pyridazinyl, and piperidinyl substituted with 1 R;

alternatively, D—E—G together represent pyridyl substituted with 1 R;

R is selected from H, Cl, F, Br, I, $(CH_2)_tOR^3$, $C_{1-4}$ alkyl, $OCF_3$, $CF_3$, $C(O)NR^7R^8$, and $(CR^8R^9)_tNR^7R^8$;

G is selected from $NHCH_2$, $OCH_2$, and $SCH_2$, provided that when s is 0, then G is absent;

Z is selected from a $C_{1-4}$ alkylene, $(CH_2)_rO(CH_2)_r$, $(CH_2)_r NR^3(CH_2)_r$, $(CH_2)_rC(O)(CH_2)_r$, $(CH_2)_rC(O)O(CH_2)_r$, $(CH_2)_rOC(O)(CH_2)_r$, $(CH_2)_rC(O)NR^3(CH_2)_r$, $(CH_2)_r NR^3C(O)(CH_2)_r$, $(CH_2)_rOC(O)O(CH_2)_r$, $(CH_2)_r OC(O)NR^3(CH_2)_r$, $(CH_2)_rNR^3C(O)O(CH_2)_r$, $(CH_2)_r NR^3C(O)NR^3(CH_2)_r$, $(CH_2)_rS(O)_p(CH_2)_r$, $(CH_2)_r SO_2NR^3(CH_2)_r$, $(CH_2)_rNR^3SO_2(CH_2)_r$, and $(CH_2)_r NR^3SO_2NR^3(CH_2)_r$, provided that Z does not form a N—N, N—O, N—S, $NCH_2N$, $NCH_2O$, or $NCH_2S$ bond with group A;

$R^{1a}$ and $R^{1b}$ are, at each occurrence, independently selected from H, $—(CH_2)_r—R^{1'}$, $NCH_2R^{1''}$, $OCH_2R^{1''}$, $SCH_2R^{1''}$, $N(CH_2)_2(CH_2)_rR^{1'}$, $O(CH_2)_2(CH_2)_rR^{1'}$, and $S(CH_2)_2(CH_2)_rR^{1'}$;

$R^{1c}$ is selected from H, $—(CH_2)_q—R^{1'}$, $C_{1-3}$ alkyl, $C(O)R^{2c}$, $(CF_2)_rCO_2R^{2c}$, $C(O)NR^2R^{2a}$, $C_{3-6}$ carbocyclic residue substituted 0–2 $R^4$, and 5–10 membered heterocyclic system comprising carbon atoms and from 1–4 heteroatoms selected from the group consisting of N, O, and S substituted 0–2 $R^4$;

$R^{1'}$ is selected from H, $C_{1-3}$ alkyl, halo, $(CF_2)_rCF_3$, $OR^2$, $NR^2R^{2a}$, $C(O)R^{2c}$, $OC(O)R^2$, $(CF_2)_rCO_2R^{2c}$, $S(O)_pR^{2b}$, $NR^2(CH_2)_rOR^2$, $NR^2C(O)R^{2b}$, $NR^2C(O)NHR^{2b}$, $NR^2C(O)_2R^{2a}$, $OC(O)NR^{2b}$, $C(O)NR^2R^{2a}$, $SO_2NR^2R^{2a}$, $NR^2SO_2R^{2b}$, $C_{3-6}$ carbocyclic residue substituted 0–2 $R^4$, and 5–10 membered heterocyclic system comprising carbon atoms and from 1–4 heteroatoms selected from the group consisting of N, O, and S substituted 0–2 $R^4$;

$R^{1''}$ is selected from H, $C(O)R^{2b}$, $C(O)NR^2R^{2a}$, $S(O)R^{2b}$, $S(O)_2R^{2b}$, and $SO_2NR^2R^{2a}$;

$R^2$, at each occurrence, is selected from H, $CF_3$, $C_{1-6}$ alkyl, benzyl, $C_{3-6}$ carbocyclic residue substituted 0–2 $R^{4b}$, and 5–6 membered heterocyclic system comprising carbon atoms and from 1–4 heteroatoms selected from the group consisting of N, O, and S substituted with 0–2 $R^{4b}$;

$R^{2a}$, at each occurrence, is selected from H, $CF_3$, $C_{1-6}$ alkyl, benzyl, $C_{3-6}$ carbocyclic residue substituted 0–2

90

$R^{4b}$, and 5–6 membered heterocyclic system comprising carbon atoms and from 1–4 heteroatoms selected from the group consisting of N, O, and S substituted with 0–2 $R^{4b}$;

$R^{2b}$, at each occurrence, is selected from $CF_3$, $C_{1-4}$ alkoxy, $C_{1-6}$ alkyl, benzyl, $C_{3-6}$ carbocyclic residue substituted with 0–2 $R^{4b}$, and 5–6 membered heterocyclic system comprising carbon atoms and from 1–4 heteroatoms selected from the group consisting of N, O, and S substituted with 0–2 $R^{4b}$;

$R^{2c}$, at each occurrence, is selected from $CF_3$, OH, $C_{1-4}$ alkoxy, $C_{1-6}$ alkyl, benzyl, $C_{3-6}$ carbocyclic residue substituted 0–2 $R^{4b}$, and 5–6 membered heterocyclic system comprising carbon atoms and from 1–4 heteroatoms selected from the group consisting of N, O, and S substituted 0–2 $R^{4b}$;

alternatively, $R^2$ and $R^{2a}$ combine to form a 5 or 6 membered saturated, partially saturated or unsaturated ring substituted 0–2 $R^{4b}$ which comprises from 0–1 additional heteroatoms selected from the group consisting of N, O, and S;

$R^3$, at each occurrence, is selected from H, $C_{1-4}$ alkyl, and phenyl;

$R^{3a}$, at each occurrence, is selected from H, $C_{1-4}$ alkyl, and phenyl;

A is selected from:
$C_{3-10}$ carbocyclic residue substituted 0–2 $R^4$, and
5–10 membered heterocyclic system comprising carbon atoms and from 1–4 heteroatoms selected from the group consisting of N, O, and S substituted 0–2 $R^4$;

B is selected from:
X—Y, $NR^2R^{2a}$, $C(=NR^2)NR^2R^{2a}$, $NR^2C(=NR^2)NR^2R^{2a}$,
$C_{3-10}$ carbocyclic residue substituted with 0–2 $R^{4a}$, and
5–10 membered heterocyclic system comprising carbon atoms and from 1–4 heteroatoms selected from the group consisting of N, O, and S substituted 0–2 $R^{4a}$;

X is selected from $C_{1-4}$ alkylene, $—CR^2(CR^2R^{2b})(CH_2)_t—$, $—C(O)—$, $—C(=NR)—$, $—CR^2(NR^{1''}R^2)—$, $—CR^2(OR^2)—$, $—CR^2(SR^2)—$, $—C(O)CR^2R^{2a}—$, $—CR^{2a}C(O)$, $—S(O)_p—$, $—S(O)_pCR^2R^{2a}—$, $—CR^2R^{2a}S(O)_p—$, $—S(O)_2NR^2—$, $—NR^2S(O)_2—$, $—NR^2S(O)_2CR^2R^{2a}—$, $—CR^2R^{2a}S(O)_2NR^2—$, $—NR^2S(O)_2NR^2—$, $—C(O)NR^2—$, $—NR^2C(O)—$, $—C(O)NR^2CR^2R^{2a}—$, $—NR^2C(O)CR^2R^{2a}—$, $—CR^2R^{2a}C(O)NR^2—$, $—CR^2R^{2a}NR^2C(O)—$, $—NR^2C(O)O—$, $—OC(O)NR^2—$, $—NR^2C(O)NR^2—$, $—NR^2—$, $—NR^2CR^2R^{2a}—$, $—CR^2R^{2a}NR^2—$, O, $—CR^2R^{2a}O—$, and $OCR^2R^{2a}—$;

Y is selected from:
$(CH_2)_rNR^2R^{2a}$, provided that X—Y do not form a N—N, O—N, or S—N bond,
$C_{3-10}$ carbocyclic residue substituted 0–2 $R^{4a}$, and
5–10 membered heterocyclic system comprising carbon atoms and from 1–4 heteroatoms selected from the group consisting of N, O, and S substituted 0–2 $R^{4a}$;

$R^4$, at each occurrence, is selected from $=O$, $(CH_2)_rOR^2$, halo, $C_{1-4}$ alkyl, $—CN$, $NO_2$, $(CH_2)_rNR^2R^{2a}$, $(CH_2)_rC(O)R^{2b}$, $NR^2C(O)R^{2b}$, $C(O)NR^2R^{2a}$, $NR^2C(O)NR^2R^{2a}$, $CH(=NR^2)NR^2R^{2a}$, $NHC(=NR^2)NR^2R^{2a}$, $SO_2NR^2R^{2a}$, $NR^2SO_2NR^2R^{2a}$, $NR^2SO_2-C_{1-4}$ $NR^2SO_2R^5$, $S(O)_pR^5$, $(CF_2)_rCF_3$, $NCH_2R^{1''}$, $OCH_2R^{1''}$, SCH$_2$R$^{1"}$, N(CH$_2$)$_2$(CH$_2$)$_t$R$^{1'}$, O(CH$_2$)$_2$(CH$_2$)$_t$R$^{1'}$, and S(CH$_2$)$_2$(CH$_2$)$_t$R$^{1'}$, alternatively, one R$^4$ is a 5–6 membered aromatic heterocycle comprising carbon atoms and from 1–4 heteroatoms selected from the group consisting of N, O, and S;

R$^{4a}$, at each occurrence, is selected from =O, (CH$_2$)$_r$OR$^2$, halo, C$_{1-4}$ alkyl, —CN, NO$_2$, (CH$_2$)$_r$NR$^2$R$^{2a}$, (CH$_2$)$_r$C(O)R$^{2b}$, NR$^2$C(O)R$^{2b}$, C(O)NR$^2$R$^{2a}$, NR$^2$C(O)NR$^2$R$^{2a}$, CH(=NR$^2$)NR$^2$R$^{2a}$, NHC(=NR$^2$)NR$^2$R$^{2a}$, SO$_2$NR$^2$R$^{2a}$, NR$^2$SO$_2$NR$^2$R$^{2a}$, NR$^2$SO$_2$-C$_{1-4}$ alkyl, NR$^2$SO$_2$R$^5$, S(O)$_p$R$^5$, and (CF$_2$)$_r$CF$_3$;

alternatively, one R$^{4a}$ is a 5–6 membered aromatic heterocycle comprising carbon atoms and from 1–4 heteroatoms selected from the group consisting of N, O, and S substituted with 0–R$^5$;

R$^{4b}$, at each occurrence, is selected from =O, (CH$_2$)$_r$OR$^3$, halo, C$_{1-4}$ alkyl, —CN, NO$_2$, (CH$_2$)$_r$NR$^3$R$^{3a}$, (CH$_2$)$_r$C(O)R$^3$, NR$^3$C(O)R$^{3a}$, C(O)NR$^3$R$^{3a}$, NR$^3$C(O)NR$^3$R$^{3a}$, CH(=NR$^3$)NR$^3$R$^{3a}$, NH$^3$C(=NR$^3$)NR$^3$R$^{3a}$, SO$_2$NR$^3$R$^{3a}$, NR$^3$SO$_2$NR$^3$R$^{3a}$, NR$^3$SO$_2$-C$_{1-4}$ alkyl, NR$^3$SO$_2$CF$_3$, NR$^3$SO$_2$-phenyl, S(O)$_p$CF$_3$, S(O)$_p$-C$_{1-4}$ alkyl, S(O)$_p$-phenyl, and (CF$_2$)$_r$CF$_3$;

R$^5$, at each occurrence, is selected from CF$_3$, C$_{1-6}$ alkyl, phenyl substituted 0–2 R$^6$, and benzyl substituted 0–2 R$^6$;

R$^6$, at each occurrence, is selected from H, OH, (CH$_2$)$_r$OR$^2$, halo, C$_{1-4}$ alkyl, CN, NO$_2$, (CH$_2$)$_r$NR$^2$R$^{2a}$, (CH$_2$)$_r$ C(O)R$^{2b}$, NR$^2$C(O)R$^{2b}$, NR$^2$C(O)NR$^2$R$^{2a}$, CH(=NH)NH$_2$, NHC(=NH)NH$_2$, SO$_2$NR$^2$R$^{2a}$, NR$^2$SO$_2$NR$^2$R$^{2a}$, and NR$^2$SO$_2$C$_{1-4}$ alkyl;

R$^7$, at each occurrence, is selected from H, OH, C$_{1-6}$ alkyl, C$_{1-6}$ alkylcarbonyl, C$_{1-6}$ alkoxy, C$_{1-4}$ alkoxycarbonyl, (CH$_2$)$_n$-phenyl, C$_{6-10}$ aryloxy, C$_{6-10}$ aryloxycarbonyl, C$_{6-10}$ arylmethylcarbonyl, C$_{1-4}$ alkylcarbonyloxy C$_{1-4}$ alkoxycarbonyl, C$_{6-10}$ arylcarbonyloxy C$_{1-4}$ alkoxycarbonyl, C$_{1-6}$ alkylaminocarbonyl, phenylaminocarbonyl, and phenyl C$_{1-4}$ alkoxycarbonyl;

R$^8$, at each occurrence, is selected from H, C$_{1-6}$ alkyl and (CH$_2$)$_n$-phenyl;

alternatively, R$^7$ and R$^8$ combine to form a 5 or 6 membered saturated, ring which comprises from 0–1 additional heteroatoms selected from the group consisting of N, O, and S;

R$^9$, at each occurrence, is selected from H, C$_{1-6}$ alkyl and (CH$_2$)$_n$-phenyl;

n, at each occurrence, is selected from 0, 1, 2, and 3;

m, at each occurrence, is selected from 0, 1, and 2;

p, at each occurrence, is selected from 0, 1, and 2;

q, at each occurrence is selected from 1 and 2;

r, at each occurrence, is selected from 0, 1, 2, and 3;

s, at each occurrence, is selected from 0, 1, and 2; and, t, at each occurrence, is selected from 0 and 1 provided that when a heterocyclic group is present it is other than a morpholine, pyrazine, primidine, pyridazine, piperidine, pyridine or tetrazole.

2. A compound according to claim 1, wherein the compound is of formula Ia:

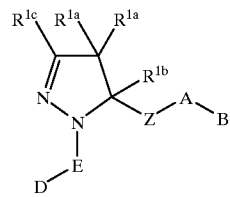

Ia wherein;

Z is selected from a CH$_2$O, OCH$_2$, CH$_2$NH, NHCH$_2$, C(O), CH$_2$C(O), C(O)CH$_2$, NHC(O), C(O)NH, CH$_2$S(O)$_2$, S(O)$_2$(CH$_2$), SO$_2$NH, and NHSO$_2$, provided that Z does not form a N—N, N—O, NCH$_2$N, or NCH$_2$O bond with group A;

A is selected from one of the following carbocyclic and heterocyclic systems which are substituted 0–2 R$^4$:
phenyl, piperidinyl, piperazinyl, pyridyl, pyrimidyl, furanyl, morpholinyl, thiophenyl, pyrrolyl, pyrrolidinyl, oxazolyl, isoxazolyl, thiazolyl, isothiazolyl, pyrazolyl, imidazolyl, oxadiazolyl, thiadiazolyl, triazolyl, 1,2,3-oxadiazolyl, 1,2,4-oxadiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, 1,2,3-triazolyl, 1,2,4-triazolyl, 1,2,5-triazolyl, 1,3,4-triazolyl, benzofuranyl, benzothiofuranyl, indolyl, benzimidazolyl, benzoxazolyl, benzthiazolyl, indazolyl, benzisoxazolyl, benzisothiazolyl, and isoindazolyl;

B is selected from: Y, X—Y, NR$^2$R$^{2a}$, C(=NR$^2$)NR$^2$R$^{2a}$, and NR$^2$C(=NR$^2$)NR$^2$R$^{2a}$;

X is selected from C$_{1-4}$ alkylene, —C(O)—, —C(=NR)—, —CR$^2$(NR$^2$R$^{2a}$)—, —C(O)CR$^2$R$^{2a}$—, —CR$^2$R$^{2a}$C(O), —C(O)NR$^2$—, —NR$^2$C(O)—, —C(O)NR$^2$CR$^2$R$^{2a}$—, —NR$^2$C(O)CR$^2$R$^{2a}$—, —CR$^2$R$^{2a}$C(O)NR$^2$—, —CR$^2$R$^{2a}$NR$^2$C(O)—, —NR$^2$C(O)NR$^2$—, —NR$^2$—, —NR$^2$CR$^2$R$^{2a}$—, —CR$^2$R$^{2a}$NR$^2$—, O, —CR$^2$R$^{2a}$O—, and —OCR$^2$R$^{2a}$—;

Y is NR$^2$R$^{2a}$, provided that X—Y do not form a N—N or O—N bond;

alternatively, Y is selected from one of the following carbocyclic and heterocyclic systems which are substituted 0–2 R$^{4a}$:
cylcopropyl, cyclopentyl, cyclohexyl, phenyl, piperidinyl, piperazinyl, pyridyl, pyrimidyl, furanyl, morpholinyl, thiophenyl, pyrrolyl, pyrrolidinyl, oxazolyl, isoxazolyl, isoxazolinyl, thiazolyl, isothiazolyl, pyrazolyl, imidazolyl, oxadiazolyl, thiadiazolyl, triazolyl, 1,2,3-oxadiazolyl, 1,2,4-oxadiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, 1,2,3-triazolyl, 1,2,4-triazolyl, 1,2,5-triazolyl, 1,3,4-triazolyl, benzofuranyl, benzothiofuranyl, indolyl, benzimidazolyl, benzoxazolyl, benzthiazolyl, indazolyl, benzisoxazolyl, benzisothiazolyl, and isoindazolyl;

alternatively, Y is selected from the following bicyclic heteroaryl ring systems:

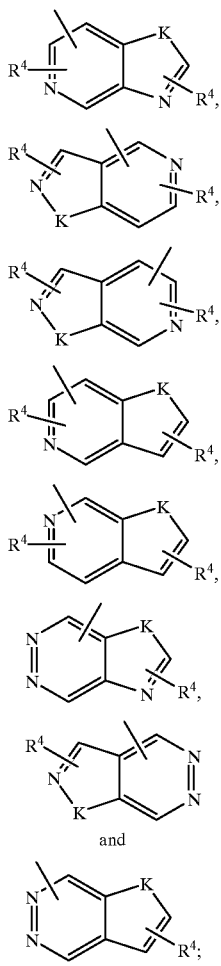

K is selected from O, S, NH, and N.

3. A compound according to claim 2, wherein;

Z is selected from a C(O), CH$_2$C(O), C(O)CH$_2$, NHC(O), C(O)NH, C(O)N(CH$_3$), CH$_2$S(O)$_2$, S(O)$_2$(CH$_2$), SO$_2$NH, and NHSO$_2$, provided that Z does not form a N—N or NCH$_2$N bond with group A.

4. A compound according to claim 3, wherein;

E is phenyl substituted with R or 2-pyridyl substituted with R;

D is selected from C(O)NH$_2$, C(=NH)NH$_2$, CH$_2$NH$_2$, CH$_2$NHCH$_3$, CH(CH$_3$)NH$_2$, and C(CH$_3$)$_2$NH$_2$; and, R is selected from H, OCH$_3$, Cl, and F.

5. A compound according to claim 4, wherein:

D—E is selected from 3-amidinophenyl, 3-aminomethylphenyl, 3-aminocarbonylphenyl, 3-(methylaminomethyl)phenyl, 3-(1-aminoethyl) phenyl, 3-(2-amino-2-propyl)phenyl, 4-chloro-3-amidinophenyl, 4-chloro-3-aminomethylphenyl, 4-chloro-3-(methylaminomethyl)phenyl, 4-fluoro-3-amidinophenyl, 4-fluoro-3-aminomethylphenyl, 4-fluoro-3 -(methylaminomethyl)phenyl, 6-amidinopyrid-2-yl, 6-aminomethylpyrid-2-yl, 6-aminocarbonylpyrid-2-yl, 6-(methylaminomethyl)pyrid-2-yl, 6-(1-aminoethyl)pyrid-2-yl, and 6-(2-amino-2-propyl)pyrid-2-yl.

6. A compound according to claim 3, wherein:

Z is C(O)CH$_2$ and CONH, provided that Z does not form a N—N bond with group A;

A is selected from phenyl, pyridyl, and pyrimidyl, and is substituted 0–2 R$^4$; and, B is selected from X—Y, phenyl, pyrrolidino, morpholino, 1,2,3-triazolyl, and imidazolyl, and is substituted with 0–1 R$^{4a}$;

R$^4$, at each occurrence, is selected from OH, (CH$_2$)$_r$OR$^2$, halo, C$_{1-4}$ alkyl, (CH$_2$)$_r$NR$^2$R$^{2a}$, and (CF$_2$)$_r$CF$_3$;

R$^{4a}$ is selected from C$_{1-4}$ alkyl, CF$_3$, S(O)$_p$R$^5$, SO$_2$NR$^2$R$^{2a}$, and 1-CF$_3$-tetrazol-2-yl;

R$^5$, at each occurrence, is selected from CF$_3$, C$_{1-6}$ alkyl, phenyl, and benzyl;

X is CH$_2$ or C(O); and,

Y is selected from pyrrolidino and morpholino.

7. A compound according to claim 6, wherein;

A is selected from the group: phenyl, 2-pyridyl, 3-pyridyl, 2-pyrimidyl, 2-Cl-phenyl, 3-Cl-phenyl, 2-F-phenyl, 3-F-phenyl, 2-methylphenyl, 2-aminophenyl, and 2-methoxyphenyl; and, B is selected from the group: 2-CF$_3$-phenyl, 2-(aminosulfonyl)phenyl, 2-(methylaminosulfonyl) phenyl, 2-(dimethylaminosulfonyl)phenyl, 1-pyrrolidinocarbonyl, 2-(methylsulfonyl)phenyl, 4-morpholino, 2-(1'-CF$_3$-tetrazol-2-yl)phenyl, 4-morpholinocarbonyl, 2-methyl-1-imidazolyl, 5-methyl-1-imidazolyl, 2-methylsulfonyl-1-imidazolyl and, 5-methyl-1,2,3-triazolyl.

8. A compound according to claim 3, wherein:

E is phenyl substituted with R or 2-pyridyl substituted with R;

D is selected from C(O)NH$_2$, C(=NH)NH$_2$, CH$_2$NH$_2$, CH$_2$NHCH$_3$, CH(CH$_3$)NH$_2$, and C(CH$_3$)$_2$NH$_2$; and, R is selected from H, OCH$_3$, Cl, and F;

Z is C(O)CH$_2$ and CONH, provided that Z does not form a N—N bond with group A;

A is selected from phenyl, pyridyl, and pyrimidyl, and is substituted 0–2 R$^4$; and, B is selected from X—Y, phenyl, pyrrolidino, morpholino, 1,2,3-triazolyl, and imidazolyl, and is substituted with 0–1 R$^{4a}$;

R$^4$, at each occurrence, is selected from OH, (CH$_2$)$_r$OR$^2$, halo, C$_{1-4}$ alkyl, (CH$_2$)$_r$NR$^2$R$^{2a}$, and (CF$_2$)$_r$CF$_3$;

R$^{4a}$ is selected from C$_{1-4}$ alkyl, CF$_3$, S(O)$_p$R$^5$, SO$_2$NR$^2$R$^{2a}$, and 1-CF$_3$-tetrazol-2-yl;

R$^5$, at each occurrence, is selected from CF$_3$, C$_{1-6}$ alkyl, phenyl, and benzyl;

X is CH$_2$ or C(O); and,

Y is selected from pyrrolidino and morpholino.

9. A compound according to claim 8 wherein:

D—E is selected from 3-amidinophenyl, 3-aminomethylphenyl, 3-aminocarbonylphenyl, 3-(methylaminomethyl)phenyl, 3-(1-aminoethyl) phenyl, 3-(2-amino-2-propyl)phenyl, 4-chloro-3-amidinophenyl, 4-chloro-3-aminomethylphenyl, 4-chloro-3-(methylaminomethyl)phenyl, 4-fluoro-3-amidinophenyl, 4-fluoro-3-aminomethylphenyl, 4-fluoro-3-(methylaminomethyl)phenyl, 6-amidinopyrid-2-yl, 6-aminomethylpyrid-2-yl, 6-aminocarbonylpyrid-2-yl, 6-(methylaminomethyl)pyrid-2-yl, 6-(1-aminoethyl)pyrid-2-yl, 6-(2-amino-2-propyl)pyrid-2-yl;

A is selected from the group: phenyl, 2-pyridyl, 3-pyridyl, 2-pyrimidyl, 2-Cl-phenyl, 3-Cl-phenyl, 2-F-phenyl, 3-F-phenyl, 2-methylphenyl, 2-aminophenyl, and 2-methoxyphenyl; and, B is selected from the group: 2-$CF_3$-phenyl, 2-(aminosulfonyl)phenyl, 2-(methylaminosulfonyl)phenyl, 2-(dimethylaminosulfonyl)phenyl, 1-pyrrolidinocarbonyl, 2-(methylsulfonyl)phenyl, 4-morpholino, 2-(1'-$CF_3$-tetrazol-2-yl)phenyl, 4-morpholinocarbonyl, 2-methyl-1-imidazolyl, 5-methyl-1-imidazolyl, 2-methylsulfonyl-1-imidazolyl and, 5-methyl-1,2,3-triazolyl.

10. A compound according to claim 9, wherein the compound is of formula Ia.

11. A compound according to claim 9, wherein the compound is of formula Ib.

12. A compound according to claim 3, wherein:

D is selected from C(=$NR^8$)$NR^7R^9$, C(O)$NR^7R^8$, $NR^7R^8$, and $CH_2NR^7R^8$;

E is phenyl substituted with R or pyridyl substituted with R;

R is selected from H, Cl, F, $OR^3$, $CH_3$, $CH_2CH_3$, $OCF_3$, and $CF_3$;

Z is selected from C(O), $CH_2$C(O), C(O)$CH_2$, NHC(O), and C(O)NH, provided that Z does not form a N—N bond with group A;

$R^{1a}$ and $R^{1b}$ are, at each occurrence, independently selected from H, —$(CH_2)_r$—$R^{1'}$, $NCH_2R^{1''}$, $OCH_2R^{1''}$, $SCH_2R^{1''}$, N$(CH_2)_2(CH_2)_rR^{1'}$, O$(CH_2)_2(CH_2)_rR^{1'}$, and S$(CH_2)_2(CH_2)_rR^{1'}$;

$R^{1c}$ is selected from H, —$(CH_2)_q$—$R^{1'}$, $C_{1-3}$ alkyl, C(O)$R^{2c}$, $(CF_2)_rCO_2R^{2c}$, and C(O)$NR^2R^{2a}$;

$R^{1'}$, at each occurrence, is selected from H, $C_{1-3}$ alkyl, halo, $(CF_2)_rCF_3$, $OR^2$, $NR^2R^{2a}$, C(O)$R^{2c}$, $(CF_2)_rCO_2R^{2c}$, S(O)$_pR^{2b}$, $NR^2(CH_2)_rOR^2$, $NR^2C(O)R^{2b}$, $NR^2C(O)_2R^{2b}$, C(O)$NR^2R^{2a}$, $SO_2NR^2R^{2a}$, and $NR^2SO_2R^{2b}$;

A is selected from one of the following carbocyclic and heterocyclic systems which are substituted with 0–2 $R^4$:
  phenyl, piperidinyl, piperazinyl, pyridyl, pyrimidyl, furanyl, morpholinyl, thiophenyl, pyrrolyl, pyrrolidinyl, oxazolyl, isoxazolyl, thiazolyl, isothiazolyl, pyrazolyl, and imidazolyl;

B is selected from: Y, X—Y, $NR^2R^{2a}$, C(=$NR^2$)$NR^2R^{2a}$, and $NR^2$C(=$NR^2$)$NR^2R^{2a}$;

X is selected from $CH_2$, —$CR^2(CR^2R^{2b})(CH_2)_t$—, —C(O)—, —C(=NR)—, —CH($NR^2R^{2a}$)—, —C(O)$NR_2$—, —$NR^2$C(O)—, —$NR^2$C(O)$NR^2$—, —$NR^2$—, and O;

Y is $NR^2R^{2a}$, provided that X—Y do not form a N—N or O—N bond;

alternatively, Y is selected from one of the following carbocyclic and heterocyclic systems which are substituted with 0–2 $R^{4a}$:
  phenyl, piperidinyl, piperazinyl, pyridyl, pyrimidyl, furanyl, morpholinyl, thiophenyl, pyrrolyl, pyrrolidinyl, oxazolyl, isoxazolyl, isoxazolinyl, thiazolyl, isothiazolyl, pyrazolyl, imidazolyl, oxadiazolyl, thiadiazolyl, triazolyl, 1,2,3-oxadiazolyl, 1,2,4-oxadiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, 1,2,3-triazolyl, 1,2,4-triazolyl, 1,2,5-triazolyl, and 1,3,4-triazolyl;

$R^4$, at each occurrence, is selected from =O, OH, Cl, F, $C_{1-4}$ alkyl, $(CH_2)_rNR^2R^{2a}$, $(CH_2)_rC(O)R^{2b}$, $NR^2C(O)R^{2b}$, C(O)$NR^2R^{2a}$, CH(=NH)$NH_2$, NHC(=NH)$NH_2$, $SO_2NR^2R^{2a}$, $NR^2SO_2$-$C_{1-4}$ alkyl, $NR^2SO_2R^5$, S(O)$_pR^5$, and $(CF_2)_rCF_3$;

$R^{4a}$, at each occurrence, is selected from =O, OH, Cl, F, $C_{1-4}$ alkyl, $(CH_2)_rNR^2R^{2a}$, $(CH_2)_rC(O)R^{2b}$, $NR^2C(O)R^{2b}$, C(O)$NR^2R^{2a}$, CH(=NH)$NH_2$, NHC(=NH)$NH_2$, $SO_2NR^2R^{2a}$, $NR^2SO_2$-$C_{1-4}$ alkyl, $NR^2SO_2R^5$, S(O)$_pR^5$, $(CF_2)_rCF_3$, and 1-$CF_3$-tetrazol-2-yl;

$R^5$, at each occurrence, is selected from $CF_3$, $C_{1-6}$ alkyl, phenyl substituted with 0–2 $R^6$, and benzyl substituted with 0–2 $R^6$;

$R^6$, at each occurrence, is selected from H, =O, OH, $OR^2$, Cl, F, $CH_3$, CN, $NO_2$, $(CH_2)_rNR^2R^{2a}$, $(CH_2)_rC(O)R^{2b}$, $NR^2C(O)R^{2b}$, CH(=NH)$NH_2$, NHC(=NH)$NH_2$, and $SO_2NR^2R^{2a}$;

$R^7$, at each occurrence, is selected from H, OH, $C_{1-6}$ alkyl, $C_{1-6}$ alkylcarbonyl, $C_{1-6}$ alkoxy, $C_{1-4}$ alkoxycarbonyl, benzyl, $C_{6-10}$ aryloxy, $C_{6-10}$ aryloxycarbonyl, $C_{6-10}$ arylmethylcarbonyl, $C_{1-4}$ alkylcarbonyloxy $C_{1-4}$ alkoxycarbonyl, $C_{6-10}$ arylcarbonyloxy $C_{1-4}$ alkoxycarbonyl, $C_{1-6}$ alkylaminocarbonyl, phenylaminocarbonyl, and phenyl $C_{1-4}$ alkoxycarbonyl;

$R^8$, at each occurrence, is selected from H, $C_{1-6}$ alkyl and benzyl; and alternatively, $R^7$ and $R^8$ combine to form a morpholino group; and, $R^9$, at each occurrence, is selected from H, $C_{1-6}$ alkyl and benzyl.

13. A compound according to claim 12, wherein;

E is phenyl substituted with R or 2-pyridyl substituted with R;

R is selected from H, Cl, F, $OCH_3$, $CH_3$, $OCF_3$, and $CF_3$;

Z is selected from a C(O)$CH_2$ and C(O)NH, provided that Z does not form a N—N bond with group A;

$R^{1a}$, at each occurrence, is selected from H, $CH_3$, $CH_2CH_3$, Cl, F, $CF_3$, $OCH_3$, $NR^2R^{2a}$, S(O)$_pR^{2b}$, $CH_2$S(O)$_pR^{2b}$, $CH_2NR^2$S(O)$_pR^{2b}$, C(O)$R^{2c}$, $CH_2$C(O)$R^{2c}$, C(O)$NR^2R^{2a}$, and $SO_2NR^2R^{2a}$;

$R^{1b}$ is selected from H, $CH_3$, $CH_2CH_3$, Cl, F, $CF_3$, $OCH_3$, $NR^2R^{2a}$, S(O)$_pR^{2b}$, $CH_2$S(O)$_pR^{2b}$, $CH_2NR^2$S(O)$_pR^{2b}$, C(O)$R^{2c}$, $CH_2$C(O)$R^{2c}$, C(O)$NR^2R^{2a}$, and $SO_2NR^2R^{2a}$;

$R^{1c}$ is selected from H, $CH_3$, $CH_2CH_3$, $CF_3$, $CH_2$S(O)$_pR^{2b}$, $CH_2NR^2$S(O)$_pR^{2b}$, C(O)$R^{2c}$, $CH_2$C(O)$R^{2c}$, and C(O)$NR^2R^{2a}$;

A is selected from one of the following carbocyclic and heterocyclic systems which are substituted with 0–2 $R^4$;
  phenyl, pyridyl, pyrimidyl, furanyl, thiophenyl, pyrrolyl, oxazolyl, isoxazolyl, thiazolyl, isothiazolyl, pyrazolyl, and imidazolyl;

B is selected from: Y and X—Y;

X is selected from $CH_2$, —$CR^2(CR^2R^{2b})$—, —C(O)—, —C(=NR)—, —CH($NR^2R^{2a}$)—, —C(O)$NR^2$—, —$NR^2$C(O)—, —$NR^2$C(O)$NR^2$—, —$NR^2$—, and O;

Y is $NR^2R^{2a}$, provided that X—Y do not form a N—N or O—N bond;

alternatively, Y is selected from one of the following carbocyclic and heterocyclic systems which are substituted with 0–2 $R^{4a}$;
  phenyl, piperidinyl, piperazinyl, pyridyl, pyrimidyl, furanyl, morpholinyl, thiophenyl, pyrrolyl, pyrrolidinyl, oxazolyl, isoxazolyl, isoxazolinyl, thiazolyl, isothiazolyl, pyrazolyl, imidazolyl, oxadiazolyl, thiadiazolyl, triazolyl, 1,2,3-oxadiazolyl, 1,2,4-oxadiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, 1,2,3-triazolyl, 1,2,4-triazolyl, 1,2,5-triazolyl, and 1,3,4-triazolyl;

$R^2$, at each occurrence, is selected from H, $CF_3$, $CH_3$, benzyl, and phenyl;

$R^{2a}$, at each occurrence, is selected from H, $CF_3$, $CH_3$, benzyl, and phenyl;

$R^{2b}$, at each occurrence, is selected from $CF_3$, $OCH_3$, $CH_3$, benzyl, and phenyl;

$R^{2c}$, at each occurrence, is selected from $CF_3$, OH, $OCH_3$, $CH_3$, benzyl, and phenyl;

alternatively, $R^2$ and $R^2a$ combine to form a 5 or 6 membered saturated, partially unsaturated, or unsaturated ring which comprises from 0–1 additional heteroatoms selected from the group consisting of N, O, and S;

$R^3$, at each occurrence, is selected from H, $CH_3$, $CH_2CH_3$, and phenyl;

$R^{3a}$, at each occurrence, is selected from H, $CH_3$, $CH_2CH_3$, and phenyl;

$R^4$, at each occurrence, is selected from OH, Cl, F, $CH_3$, $CH_2CH_3$, $NR^2R^{2a}$, $CH_2NR^2R^{2a}$, $C(O)R^{2b}$, $NR^2C(O)R^{2b}$, $C(O)NR^2R^{2a}$, and $CF_3$;

$R^{4a}$, at each occurrence, is selected from OH, Cl, F, $CH_3$, $CH_2CH_3$, $NR^2R^{2a}$, $CH_2NR^2R^{2a}$, $C(O)R^{2b}$, $C(O)NR^2R^{2a}$, $SO_2NR^2R^{2a}$, $S(O)_pR^5$, $CF_3$, and 1-$CF_3$-tetrazol-2-yl;

$R^5$, at each occurrence, is selected from $CF_3$, $C_{1-6}$ alkyl, phenyl substituted with 0–2 $R^6$, and benzyl substituted with 1 $R^6$;

$R^6$, at each occurrence, is selected from H, OH, $OCH_3$, Cl, F, $CH_3$, CN, $NO_2$, $NR^2R^{2a}$, $CH_2NR^2R^{2a}$, and $SO_2NR^2R^{2a}$;

$R^7$, at each occurrence, is selected from H, OH, $C_{1-3}$ alkyl, $C_{1-3}$ alkylcarbonyl, $C_{1-3}$ alkoxy, $C_{1-4}$ alkoxycarbonyl, benzyl, phenoxy, phenoxycarbonyl, benzylcarbonyl, $C_{1-4}$ alkylcarbonyloxy $C_{1-4}$ alkoxycarbonyl, phenylcarbonyloxy $C_{1-4}$ alkoxycarbonyl, $C_{1-6}$ alkylaminocarbonyl, phenylaminocarbonyl, and phenyl $C_{1-4}$ alkoxycarbonyl;

$R^8$, at each occurrence, is selected from H, $CH_3$, and benzyl; and, alternatively, $R^7$ and $R^8$ combine to form a morpholino group;

$R^9$, at each occurrence, is selected from H, $CH_3$, and benzyl.

14. A compound according to claim 13, wherein:

$R^{1a}$, at each occurrence, is selected from H, $CH_3$, $CH_2CH_3$, Cl, F, $CF_3$, $OCH_3$, $NR^2R^{2a}$, $S(O)_pR^{2b}$, $C(O)NR^2R^{2a}$, $CH_2S(O)_pR^{2b}$, $CH_2NR^2S(O)_pR^{2b}$, $C(O)R^{2c}$, $CH_2C(O)R^{2c}$, and $SO_2NR^2R^{2a}$;

$R^{1b}$ is selected from H, $CH_3$, $CH_2CH_3$, Cl, F, $CF_3$, $OCH_3$, $NR^2R^{2a}$, $S(O)_pR^{2b}$, $C(O)NR^2R^{2a}$, $CH_2S(O)_pR^{2b}$, $CH_2NR^2S(O)_pR^{2b}$, $C(O)R^{2b}$, $CH_2C(O)R^{2b}$, and $SO_2NR^2R^{2a}$;

$R^{1c}$ is selected from H, $CH_3$, $CH_2CH_3$, $CF_3$, $C(O)NR^2R^{2a}$, $CH_2S(O)_pR^{2b}$, $CH_2NR^2S(O)_pR^{2b}$, $C(O)R^{2b}$, and $CH_2C(O)R^{2b}$;

A is selected from one of the following carbocyclic and heterocyclic systems which are substituted with 0–2 $R^4$;
  phenyl, pyridyl, and pyrimidyl;

B is selected from: Y and X—Y;

X is selected from —C(O)— and O;

Y is $NR^2R^{2a}$, provided that X—Y do not form a O—N bond;

alternatively, Y is selected from one of the following carbocyclic and heterocyclic systems which are substituted with 0–2 $R^{4a}$:
  phenyl, piperazinyl, pyridyl, pyrimidyl, morpholinyl, pyrrolidinyl, imidazolyl, and 1,2,3-triazolyl;

$R^2$, at each occurrence, is selected from H, $CF_3$, $CH_3$, benzyl, and phenyl;

$R^{2a}$, at each occurrence, is selected from H, $CF_3$, $CH_3$, benzyl, and phenyl;

$R^{2b}$, at each occurrence, is selected from $CF_3$, $OCH_3$, $CH_3$, benzyl, and phenyl;

$R^{2c}$, at each occurrence, is selected from $CF_3$, OH, $OCH_3$, $CH_3$, benzyl, and phenyl;

alternatively, $R^2$ and $R^{2a}$ combine to form a ring system selected from pyrrolidinyl, piperazinyl and morpholino;

$R^4$, at each occurrence, is selected from Cl, F, $CH_3$, $NR^2R^{2a}$, and $CF_3$;

$R^{4a}$, at each occurrence, is selected from Cl, F, $CH_3$, $SO_2NR^2R^{2a}$, $S(O)_pR^5$, and $CF_3$; and, $R^5$, at each occurrence, is selected from $CF_3$ and $CH_3$.

15. A compound according to claim 1, wherein the compound is selected from the group:

1-(3-amidinophenyl)-5-[[(2'-methylsulfonyl-[1,1']-biphen-4-yl)-aminocarbonyl]-3-trifluoromethyl-pyrazoline; and, 1-(3-aminomethylphenyl)-5-[[(2'-methylsulfonyl-[1,1']-biphen-4-yl)-aminocarbonyl]-3-trifluoromethyl-pyrazoline;

and pharmaceutically acceptable salts thereof.

16. A pharmaceutical composition, comprising: a pharmaceutically acceptable carrier and a therapeutically effective amount of a compound according to claim 1 or a pharmaceutically acceptable salt thereof.

17. A method for treating a thromboembolic disorder, comprising: administering to a patient in need thereof a therapeutically effective amount of a compound according to claim 1 or a pharmaceutically acceptable salt thereof.

18. A pharmaceutical composition, comprising: a pharmaceutically acceptable carrier and a therapeutically effective amount of a compound according to claim 2 or a pharmaceutically acceptable salt thereof.

19. A pharmaceutical composition, comprising: a pharmaceutically acceptable carrier and a therapeutically effective amount of a compound according to claim 3 or a pharmaceutically acceptable salt thereof.

20. A pharmaceutical composition, comprising: a pharmaceutically acceptable carrier and a therapeutically effective amount of a compound according to claim 4 or a pharmaceutically acceptable salt thereof.

21. A pharmaceutical composition, comprising: a pharmaceutically acceptable carrier and a therapeutically effective amount of a compound according to claim 5 or a pharmaceutically acceptable salt thereof.

22. A pharmaceutical composition, comprising: a pharmaceutically acceptable carrier and a therapeutically effective amount of a compound according to claim 6 or a pharmaceutically acceptable salt thereof.

23. A pharmaceutical composition, comprising: a pharmaceutically acceptable carrier and a therapeutically effective amount of a compound according to claim 7 or a pharmaceutically acceptable salt thereof.

24. A pharmaceutical composition, comprising: a pharmaceutically acceptable carrier and a therapeutically effective amount of a compound according to claim 8 or a pharmaceutically acceptable salt thereof.

25. A pharmaceutical composition, comprising: a pharmaceutically acceptable carrier and a therapeutically effective amount of a compound according to claim 9 or a pharmaceutically acceptable salt thereof.

26. A pharmaceutical composition, comprising: a pharmaceutically acceptable carrier and a therapeutically effective amount of a compound according to claim 10 or a pharmaceutically acceptable salt thereof.

27. A pharmaceutical composition, comprising: a pharmaceutically acceptable carrier and a therapeutically effective amount of a compound according to claim 11 or a pharmaceutically acceptable salt thereof.

28. A pharmaceutical composition, comprising: a pharmaceutically acceptable carrier and a therapeutically effective amount of a compound according to claim 12 or a pharmaceutically acceptable salt thereof.

29. A pharmaceutical composition, comprising: a pharmaceutically acceptable carrier and a therapeutically effective amount of a compound according to claim 13 or a pharmaceutically acceptable salt thereof.

30. A pharmaceutical composition, comprising: a pharmaceutically acceptable carrier and a therapeutically effective amount of a compound according to claim 14 or a pharmaceutically acceptable salt thereof.

31. A pharmaceutical composition, comprising: a pharmaceutically acceptable carrier and a therapeutically effective amount of a compound according to claim 15 or a pharmaceutically acceptable salt thereof.

32. A method for treating a thromboembolic disorder, comprising: administering to a patient in need thereof a therapeutically effective amount of a compound according to claim 2 or a pharmaceutically acceptable salt thereof.

33. A method for treating a thromboembolic disorder, comprising: administering to a patient in need thereof a therapeutically effective amount of a compound according to claim 3 or a pharmaceutically acceptable salt thereof.

34. A method for treating a thromboembolic disorder, comprising: administering to a patient in need thereof a therapeutically effective amount of a compound according to claim 4 or a pharmaceutically acceptable salt thereof.

35. A method for treating a thromboembolic disorder, comprising: administering to a patient in need thereof a therapeutically effective amount of a compound according to claim 5 or a pharmaceutically acceptable salt thereof.

36. A method for treating a thromboembolic disorder, comprising: administering to a patient in need thereof a therapeutically effective amount of a compound according to claim 6 or a pharmaceutically acceptable salt thereof.

37. A method for treating a thromboembolic disorder, comprising: administering to a patient in need thereof a therapeutically effective amount of a compound according to claim 7 or a pharmaceutically acceptable salt thereof.

38. A method for treating a thromboembolic disorder, comprising: administering to a patient in need thereof a therapeutically effective amount of a compound according to claim 8 or a pharmaceutically acceptable salt thereof.

39. A method for treating a thromboembolic disorder, comprising: administering to a patient in need thereof a therapeutically effective amount of a compound according to claim 9 or a pharmaceutically acceptable salt thereof.

40. A method for treating a thromboembolic disorder, comprising: administering to a patient in need thereof a therapeutically effective amount of a compound according to claim 10 or a pharmaceutically acceptable salt thereof.

41. A method for treating a thromboembolic disorder, comprising: administering to a patient in need thereof a therapeutically effective amount of a compound according to claim 11 or a pharmaceutically acceptable salt thereof.

42. A method for treating a thromboembolic disorder, comprising: administering to a patient in need thereof a therapeutically effective amount of a compound according to claim 12 or a pharmaceutically acceptable salt thereof.

43. A method for treating a thromboembolic disorder, comprising: administering to a patient in need thereof a therapeutically effective amount of a compound according to claim 13 or a pharmaceutically acceptable salt thereof.

44. A method for treating a thromboembolic disorder, comprising: administering to a patient in need thereof a therapeutically effective amount of a compound according to claim 14 or a pharmaceutically acceptable salt thereof.

45. A method for treating a thromboembolic disorder, comprising: administering to a patient in need thereof a therapeutically effective amount of a compound according to claim 15 or a pharmaceutically acceptable salt thereof.

* * * * *

UNITED STATES PATENT AND TRADEMARK OFFICE
CERTIFICATE OF CORRECTION

PATENT NO. : 6,191,159 B1
APPLICATION NO. : 09/276960
DATED : February 20, 2001
INVENTOR(S) : Donald J. P. Pinto It is certified that error appears in the above-identified patent and that said Letters Patent is hereby corrected as shown below:

At column 5, line 20, delete the "$CH(=NR^2)NR^2R^{2a}$" and insert -- $C(=NR^2)NR^2R^{2a}$ --;
at column 5, line 31, delete the "$CH(=NR^2)NR^2R^{2a}$" and insert -- $C(=NR^2)NR^2R^{2a}$ --;
at column 5, line 42, delete the "$CH(=NR^3)NR^3R^{3a}$" and insert -- $C(=NR^3)NR^3R^{3a}$ --;
at column 5, line 51, delete the "$CH(=NH)NH_2$" and insert -- $C(=NH)NH_2$ --;
at column 10, line 13, delete the "$CH(=NH)NH_2$" and insert -- $C(=NH)NH_2$ --;
at column 10, line 18, delete the "$CH(=NH)NH_2$" and insert -- $C(=NH)NH_2$ --;
at column 10, line 26, delete the "$CH(=NH)NH_2$" and insert -- $C(=NH)NH_2$ --;
at column 89, line 45, delete the "comprising" and insert -- having --;
at column 89, line 55, delete the "comprising" and insert -- having --;
at column 89, lines 62-63, delete the "comprising" and insert -- having --;
at column 90, lines 1-2, delete the "comprising" and insert -- having --;
at column 90, line 8, delete the "comprising" and insert -- having --;
at column 90, line 14, delete the "comprising" and insert--having--;
at column 90, line 19, delete the "which comprises" and insert -- having --;
at column 90, line 29, delete the "comprising" and insert -- having --;
at column 90, line 37, delete the "comprising" and insert -- having --;
at column 90, line 58, delete the "comprising" and insert -- having --;
at column 90, line 65, delete the "$CH(=NR^2)NR^2R^{2a}$" and insert -- $C(=NR^2)NR^2R^{2a}$ --;
at column 91, line 10, delete the "$CH(=NR^2)NR^2R^{2a}$" and insert -- $C(=NR^2)NR^2R^{2a}$ --;
at column 91, line 21, delete the "$CH(=NR^3)NR^3R^{3a}$" and insert -- $C(=NR^3)NR^3R^{3a}$ --;
at column 91, line 33, delete the "$CH(=NH)NH_2$" and insert -- $C(=NH)NH_2$ --;
at column 91, line 4, delete the "comprising" and insert -- having --;
at column 91, line 15, delete the "comprising" and insert -- having --;
at column 91, line 47, delete the "which comprises" and insert -- having --;
at column 91, line 62, insert -- . -- after "from 0 and 1";
at column 91, lines 62-65, delete the "provided that when a heterocyclic group is present it is other than a morpholine, pyrazine, primidine, pyidazine, piperidine, pyridine or tetrazole.";
at column 95, line 67, delete the "$CH(=NH)NH_2$" and insert -- $C(=NH)NH_2$ --;
at column 96, line 5, delete the "$CH(=NH)NH_2$" and insert -- $C(=NH)NH_2$ --;
at column 96, line 13, delete the "$CH(=NH)NH_2$" and insert -- $C(=NH)NH_2$ --;
at column 97, line 17, delete the "$R^2a$" and insert -- $R^{2a}$ --;

UNITED STATES PATENT AND TRADEMARK OFFICE
CERTIFICATE OF CORRECTION

PATENT NO. : 6,191,159 B1
APPLICATION NO. : 09/276960
DATED : February 20, 2001
INVENTOR(S) : Donald J. P. Pinto It is certified that error appears in the above-identified patent and that said Letters Patent is hereby corrected as shown below:

at column 97, line 19, delete the "which comprises" and insert -- having --.

Signed and Sealed this

Twenty-fourth Day of July, 2007

JON W. DUDAS
*Director of the United States Patent and Trademark Office*